US008940535B2

(12) United States Patent
Trisler et al.

(10) Patent No.: US 8,940,535 B2
(45) Date of Patent: Jan. 27, 2015

(54) STEM CELL CULTURE MEDIUM AND METHOD OF USING SAID MEDIUM AND THE CELLS

(75) Inventors: G. David Trisler, Chevy Chase, MD (US); Christopher T. Bever, Jr., Glen Arm, MD (US); James E. Goolsby, Baltimore, MD (US); Bernard M. Pessac, Paris (FR)

(73) Assignees: University of Maryland, Baltimore, Baltimore, MD (US); The United States of America as Represented by the Dept of Veterans Affairs, Washington, DC (US)

( * ) Notice: Subject to any disclaimer, the term of this patent is extended or adjusted under 35 U.S.C. 154(b) by 1128 days.

(21) Appl. No.: 10/982,381

(22) Filed: Nov. 4, 2004

(65) Prior Publication Data
US 2005/0164380 A1 Jul. 28, 2005

Related U.S. Application Data

(60) Provisional application No. 60/517,210, filed on Nov. 4, 2003.

(51) Int. Cl.
C12N 5/00 (2006.01)
(52) U.S. Cl.
USPC .......... 435/375; 435/325; 435/383; 435/384; 435/386; 424/93.7
(58) Field of Classification Search
CPC .. C12N 5/0647; C12N 5/0695; C12N 5/0696; C12N 2501/603; C12N 2502/1388; C12N 5/0662; C12N 5/0667; C12N 5/0668
See application file for complete search history.

(56) References Cited

U.S. PATENT DOCUMENTS

| 5,459,069 | A | * | 10/1995 | Palsson et al. ............. 435/289.1 |
| 5,486,359 | A | | 1/1996 | Caplan et al. |
| 5,580,724 | A | * | 12/1996 | Alter .................................. 435/6 |
| 5,827,742 | A | * | 10/1998 | Scadden ....................... 435/377 |
| 5,830,651 | A | | 11/1998 | Cauley et al. |
| 6,077,987 | A | | 6/2000 | Breitbart et al. |
| 6,082,364 | A | * | 7/2000 | Balian et al. ................... 128/898 |
| 6,387,367 | B1 | | 5/2002 | Davis-Sproul et al. |

FOREIGN PATENT DOCUMENTS

| EP | 0455482 B1 | 8/1997 |
| WO | WO-94/02593 | 2/1994 |
| WO | WO-9623872 A | 8/1996 |
| WO | WO 01/53461 | 7/2001 |
| WO | WO-0212452 A | 2/2002 |
| WO | WO 03/089631 | 10/2003 |

OTHER PUBLICATIONS

Bhattacharya. B et al. 2004. Gene expression in human embryonic stem cell lines: unique molecular signature. Blood 103: 2956-2964.*
Griffiths, B. "Scaling-up of animal cell cultures." in: Masters, JRW, ed., Animal Cell Culture: A Practical Approach, 3rd ed. (Oxford UK, Oxford University Press, 2000), pp. 48-50.*
Bhattacharya, B., et al., "Gene expression in human embryonic stem cell lines: unique molecular signature," Blood (Apr. 2004) vol. 103, No. 8, pp. 2956-2964.
Breems, D. A., et. al., "Stroma-contact prevents loss of hematopoietic stem cells quality during ex vivo expansion of CD34+ mobilized peripheral blood stem cells," Blood (Jan. 1998), vol. 91, No. 1, pp. 111-117.
Cai, J., et al., In search of "stemness", Experimental Hematology, (2004) vol. 32, pp. 585-598.
Dexter, T.M., et al., "Conditions controlling the proliferation of haemopoietic stems cells in vitro," J. Cell. Physiol., (Jun. 1976) vol. 91, pp. 335-344.
Drouet, X., et al., "Human liquid bone marrow culture in serum-free medium", Brit. J. of Haematology (1989), vol. 73, pp. 143-147.
Fibach, E., et al., "Proliferation and Maturation of Human Erythroid Progenitors in Liquid Culture", Blood (Jan. 1989) vol. 73, No. 1, pp. 100-103.
Goolsby, J., et al., "Hematopoietic progenitors express neural genes", PNAS (Dec. 2003), vol. 100, No. 25, pp. 14926-14931.
Jiang, Y., et al., "Pluripotency of mesenchymal stem cells derived from adult marrow," Nature, (Jul. 2002), vol. 418, pp. 41-49.
Makar, T.K., et. al., "Brain-derived neurotrophic factor (BDNF) gene delivery into the CNS using bone marrow cells as vehicles in mice," Neuroscience Letters, (2004), vol. 356, pp. 215-219.
Miyamoto, T., et. al., "An adherent condition is required for formation of multinuclear osteoclasts in the presence of macrophase colony-stimulating factor and receptor activator of nuclear factor kB ligand," Blood (Dec. 2000), vol. 96, No. 13, pp. 4335-4343.
Nichol, J. L., et al., "Enrichment and characterization of peripheral blood-derived megakaryocyte progenitors that mature in short-term liquid culture," Stem Cells (1994), vol. 12, pp. 494-505.
Shaw, Peter H., et al.,"Ex Vivo expansion of megakaryocyte precursors from umbilical cord blood CD34+ cells in a closed liquid culture system," Bio. of Blood and Marrow Transp. (2003) vol. 9, pp. 151-156.
Song, Z. X., et al.,"Hematopoietic factor production by a cell line (TC-1) derived from adherent murine marrow cells," Blood, (Aug. 1985), vol. 66, No. 2, pp. 273-281.
Steidl, U., et al., "Primary human CD34+ hematopoietic stem and progenitor cells express functionally active receptors of neuromediators," Blood (Jul. 2004), vol. 104, No. 1, pp. 81-88.

(Continued)

Primary Examiner — Lora E Barnhart Driscoll
(74) Attorney, Agent, or Firm — Fulbright & Jaworski LLP

(57) ABSTRACT

Methods and compositions are provided for isolation of proliferating cells. In particular, the methods enrich stem cells in a mixture of stem cells and non-stem cells, and in some cases the non-stem cells may be differentiated cells. The methods exploit the non-adherent property of stem cells, as opposed to the adherent property of differentiating cells, by serially passaging the suspended cells in liquid media.

8 Claims, 21 Drawing Sheets

(56) References Cited

OTHER PUBLICATIONS

Terstappen, L.W.M.M., et al., "Analysis of bone marrow stem cell," Blood Cells, (1994) vol. 20, pp. 45-63.

Wen-Hong, C., et. al, "Myeloid and erythroid hemopoiesis supported by human bone marrow fibroblasts in vitro", Chinese Med. J., (1992), vol. 105, No. 7, pp. 544-548.

Young, H. E., et al., "Adult stem cells," The Anat. Rec. Part A., (2004) vol. 276A, pp. 75-102.

Hohlfeld et al., "The neuroprotective effect of inflammation: implications for the therapy of multiple sclerosis"; Journal of Neuroimmunolocy; Jul. 24, 2000; pp. 161-166(6); vol. 107(2).

Soria et al., "From stem cells to beta cells: new strategies in cell therapy of diabetes mellitus"; Diabetologial; Apr. 2001; 407-15; vol. 44(4).

Goolsby et al., "Hematopoietic progenitors express neural genes," Proc Natl Acad Sci U S A. Dec. 9, 2003;100(25):14926-31.

Diduch, D.R., et al, "Two Cell Lines from Bone Marrow That Differ in Terms of Collagen Synthesis, Osteogenic Characteristics, and Matrix Mineralization", (Jan. 1993), *The Journal of Bone and Joint Surgery*, vol. 75-A, No. 1, pp. 92-105.

Cohen et al., "In vitro quantitation of engraftment between purified populations of bone marrow hemopoietic stem cells and stromal cells," *Proc. Keystone ICN-UCLA Symposia on Biology of Bone Marrow*, pp. 491-505, 1980.

Office Action issued in Japanese Application No. 2006-539694 (and English language translation thereof), mailed Aug. 31, 2010.

First Substantive Examination Report, issued Mar. 8, 2010 (published Mar. 8, 2010) during the prosecution of European Application No. 04 800 864.3-2406.

First Substantive Examination Report, issued May 19, 2010 (published May 19, 2010) during the prosecution of Australian Application No. 2004288722.

Article 94(3) EPC Communication issued in European Patent Application No. 04800864.3, mailed Apr. 14, 2014.

\* cited by examiner

| Marker | % Diploid CD34 ± SD | % Trisomic CD34 ± SD |
|---|---|---|
| cKit | 87.87 ± 15.21 | 97.62 ± 4.76 |
| Sca1 | 96.5 ± 6.1 | 96.4 ± 5.94 |
| CD38 | 86.39 ± 3.31 | 91.30 ± 12.13 |
| Ki67+ | 89.2 ± 12.51 | 28.20 ± 7.6 |
| Caspase3 | 29.21 ± 6.73 | 87.05 ± 10.25 |
| Tunel | 17.63 ± 7.41 | 70.0 ± 8.18 |

SEQUENCE LISTING

```
<160> NUMBER OF SEQ ID NOS: 22

<210> SEQ ID NO 1
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 1
atggaggtgg cgcctgagca gcct                                          24

<210> SEQ ID NO 2
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 2
ctgccgcctt ccatcttcat gctc                                          24

<210> SEQ ID NO 3
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 3
atgtcctcgg ccatcgaaag gaag                                          24
```

```
<210> SEQ ID NO 4
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 4
gatgatccca ttgatcttgg tcca                                              24

<210> SEQ ID NO 5
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 5
caccatccgg gatgaaagtg agat                                              24

<210> SEQ ID NO 6
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 6
accagaaaat gtcgctttag tttc                                              24

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 7
ccgtgaagtt ggagaaggtg                                                   20

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 8
tgattggcga tgtgatgtat                                                   20

<210> SEQ ID NO 9
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 9
cgtaccgaat ggtgcgagga tccc                                              24

<210> SEQ ID NO 10
<211> LENGTH: 24
<212> TYPE: DNA
<213> ORGANISM: ARTIFICIAL SEQUENCE
<220> FEATURE:
```

```
<223> OTHER INFORMATION: Primer

<400> SEQUENCE: 10
catggttcac atggatggcc ttac                                          24

<210> SEQ ID NO 11
<211> LENGTH: 28
<212> TYPE: DNA
<213> ORGANISM: ARTIFICIAL SEQUENCE
<220> FEATURE:
<223> OTHER INFORMATION: Primer

<400> SEQUENCE: 11
gatgacggag cggccgccga gcgaggcg                                      28

<210> SEQ ID NO 12
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 12
cgcactactt tggtgtgagg acca                                          24

<210> SEQ ID NO 13
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 13
cagtatttcc acttcagaga tgac                                          24

<210> SEQ ID NO 14
<211> LENGTH: 24
<212> TYPE: DNA
<213> ORGANISM: ARTIFICIAL SEQUENCE
<220> FEATURE:
<223> OTHER INFORMATION: Primer

<400> SEQUENCE: 14
gtgtaataag ggtcttcacc cagc                                          24

<210> SEQ ID NO 15
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 15
attggctttg gtccgagtcc                                               20

<210> SEQ ID NO 16
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 16
gggggttctt tggcttttac                                               20
```

```
<210> SEQ ID NO 17
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 17
ctttcctgcg gcgatatcac                                                 20

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 18
tcctcaacct ttccctcaat                                                 20

<210> SEQ ID NO 19
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 19
gcagaacgcc gaagagtggt                                                 20

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 20
cgagcagaca tcaagtagga                                                 20

<210> SEQ ID NO 21
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 21
aacccaccca ggcttttgtc                                                 20

<210> SEQ ID NO 22
<211> LENGTH: 20
<212> TYPE: DNA
<213> ORGANISM: ARTIFICIAL SEQUENCE
<220> FEATURE:
<223> OTHER INFORMATION: Primer

<400> SEQUENCE: 22
tccacaatgc cacgcttctg                                                 20
```

STEM CELL CULTURE MEDIUM AND METHOD OF USING SAID MEDIUM AND THE CELLS

The present invention claims priority to U.S. Provisional Application Ser. No. 60/517,210, filed Nov. 4, 2003, which is incorporated by reference herein in its entirety.

STATEMENT REGARDING FEDERALLY SPONSORED RESEARCH OR DEVELOPMENT

The present invention utilized funds from the Veterans Administration Merit Review accorded to inventors G. David Trisler and Christopher T. Bever.

FIELD OF THE INVENTION

The present invention generally concerns at least the fields of cell biology, molecular biology, and medicine. More particularly, the present invention regards novel methods and compositions directed to cell culture media and applications for the cells.

BACKGROUND OF THE INVENTION

The production and application of stem cells useful in basic research, clinical research, and for cell-based therapies, such as for the generation of differentiated cells and/or tissues. Today, donated organs and tissues are often used to replace ailing or destroyed tissue, but the need for transplantable tissues and organs far outweighs the available supply. Stem cells, directed to differentiate into specific cell types, provide a renewable source of replacement cells and tissues to treat diseases including, for example, Parkinson's and Alzheimer's diseases, spinal cord injury, stroke, burns, heart disease, diabetes, osteoarthritis, rheumatoid arthritis, amyotrophic lateral sclerosis, and so forth.

A variety of stem cells are known in different tissues of the body, and in many embodiments the tissue source of the stem cell does not limit the target application to which it will be applied. However, in other embodiments the stem cells are employed for a consonant tissue purpose. For example, adult bone marrow contains stem cells that replenish the haematopoietic system at a high turnover rate by generating cells of the myeloid and lymphoid lineages. Since bone marrow cells are accessible and readily available, the hypothesis arose that bone marrow may be a source of stem cells for tissues other than the haematopoietic system. The consequence of this rationale is that several laboratories are attempting to develop strategies to use bone marrow cells for brain cell replacement therapy. They have used ex vivo bone marrow cells, either unselected (Brazelton et al., 2000; Mezey et al., 2000; Makar et al., 2002; Hess et al., 2002) or a selected subpopulation (Bonilla et al., 2002; Caastro et al., 2002) or cells cultured from bone marrow (Azizi et al., 1998; Kpen et al., 1999; Woodbury et al., 2000; Kabos et al., 2002). When injected into recipient animals, bone marrow cells were found in the brain expressing neural markers in most cases. Previously, the neural myelin basic protein (MBP) gene was found to be expressed in bone marrow in vivo (Marty et al., 2002). This raised the possibility that some in vivo bone marrow cells express other neural genes.

WO 94/02593 concerns multipotent neural stem cells that are cultured in the absence of feeder cell layers. In specific embodiments liquid culture media is employed. In particular embodiments, however, the cells are cultured by contacting a substrate with an embryonic neural tube followed by contacting the cells with a second culture medium that permits self-regeneration and differentiation.

U.S. Pat. No. 5,830,651 is directed to methods of producing pre-oligodendroglial stem cells by culturing a neural cell in a vessel in a serum-containing basal media wherein a surface in the vessel allows attachment of the neural cell. In specific embodiments, the surface of the vessel is coated with a polybasic amino acid or an extracellular matrix molecule.

EP0455482 relates to human progenitor cells that are $CD34+/CD38^-$ and their use in bone marrow transplantation and gene therapy. Their isolation is accomplished by flow cytometry or magnetic bead cell separation, such as with using monoclonal antibodies.

The present invention satisfies a need in the art for culturing stem cells, including methods and compositions related thereto, such as application of the uniquely derived cells in a cell replacement therapy.

SUMMARY OF THE INVENTION

The present invention is directed to a system and method concerning stem cells, cell culture media, and applications for the cells obtained therefrom.

In particular, the present invention employs passaging suspended cells in liquid media to enrich the cells for non-differentiated cells as opposed to differentiated cells. The term "enrich" as used herein refers to increasing the quantity of non-differentiated cells, and in particular embodiments it refers to increasing the ratio of non-differentiated cells to differentiated cells. This may be further described as successively isolating stem cells from undesired differentiated cells. This may be even further defined as generating increasingly pure stem cell cultures with each successive passage.

The term "suspended" as used herein refers to those cells in a liquid media that are not adherent to the container holding the liquid media. The suspended cells may be considered as having as its majority continuously dividing cells. The present inventors have exploited the distinguishing growth characteristics between stem cells and non-stem cells (which may be referred to as differentiated cells) by utilizing the adherent properties of differentiated cells. That is, whereas differentiated cells will adhere to other cells and/or substrates by nature, stem cells generally do not. Therefore, the present invention takes advantage of this property by providing an initial mixture of cells comprising one or more stem cells and continually passaging the suspended cells and excluding the adherent cells, such as exchanging the cells adhering to the culturing container. In the event that there are differentiated cells that remain in suspension, such as differentiating cells that do not adhere to a container or substrate, for example, these cells would by nature stop dividing and be diluted out upon passaging. Exemplary cells of these type include erythroblasts and white blood cells.

The initial mixture of cells may be a group of cells or tissue fragments comprising multiple cells, although it is beneficial to have singular cells rather than tissue fragments. The continual passaging of the suspended cells may employ any suitable method, such as pipetting, pouring, or automated liquid transfer device for cell culture, and so forth, so long as it facilitates excluding at least the majority of adherent cells. In specific embodiments, the suspended cells may be centrifuged prior to delivery to a subsequent culturing container, which may comprise fresh media, conditioned media, or a mixture thereof. Such centrifugation may occur upon one passage, upon more than one passage, or at every passage, but in specific embodiments it does not occur in at least the first passaging.

As used herein, the term "passaging" refers to the transfer of at least some cells in a first container having liquid media to a second container having liquid media. The transfer may include at least some media from the first container. The passaging may be to facilitate continued proliferation and provide sufficient nutrients to the cells, such that an acceptable density threshold is not surpassed in a given container.

The suspended cells may be passaged once or more than once. The timing of passaging of the cells may occur at any suitable time such that the suspended cells remain in a healthy state, such as a state wherein the cell maintains the ability to proliferate. In particular, the timing of the passaging may occur dependent upon the density of the cells. For example, in specific embodiments cells are passaged when the density reaches about $8 \times 10^5$ to about $2 \times 10^6$ cells/ml medium. In a particular embodiment, the suspended cells are not passaged unless the fraction of stem cells to initial mixture of cells is about $8 \times 10^5$. In specific embodiments, earlier cultures in the passaging series are passaged less frequently than later cultures, given that the density of the cells in the media is lower. In further specific embodiments, the cultures are passaged at a frequency of less than once a week, about once a week, or more than once a week. In specific embodiments, cells are resuspended after passage at no less than $10^5$ cells/ml medium. In specific embodiments, if the cells are not maintained above a certain density, they slow their division rate and the culture dies.

The culturing container may be of any suitable shape or material such that it distinguishes cells that adhere to each other and/or substrates from cells that do not adhere to teach other or to a substrate. In a particular embodiment, the substrate is a container. In specific embodiments, the container shape is a conical, rectangular, spherical, or semi-circular flask or a tissue culture Petri dish, for example. In other embodiments, the container material is glass or plastic. In particular embodiments, the container material is untreated and comprises no specific agent placed thereon to facilitate adherence of the non-proliferating cells. In further specific embodiments, the container material is biologically inert.

In specific embodiments, culture media from one container is transferred in addition to the suspended cells into a subsequent container. In specific embodiments, the media from the prior container comprises one or more beneficial components, such as growth factors, cytokines, autocrine molecules, paracrine molecules, or a mixture thereof. This media may be referred to as "conditioned" media. The ratio of transferred media ("conditioned" media) to fresh media in a subsequent flask may be of any suitable amount such that there is continued survival and proliferation of the stem cells of the suspension media.

In particular embodiments, the culture media does not comprise antibiotics, although in alternative embodiments, the culture media does comprise antibiotics, such as penicillin or streptomycin, for example. In the embodiments wherein antibiotics are employed in the media, they may be removed (such as by replacing the media with antibiotic-minus media) following elimination of the pathogen(s). The media may comprise serum, such as bovine serum (including fetal bovine serum) or horse serum, for example. In the embodiments wherein serum is employed in the media, the amount may be from about 5% to about 15% serum, for example. A skilled artisan recognizes that too high amounts of serum in the media are toxic to at least some cells. In other embodiments, a skilled artisan recognizes that the media does not contain matrix or feeder cells.

Although stem cells may be derived from any tissue harboring stem cells, in particular embodiments they are from bone marrow, embryos, mesenchyme, neural tissue, pancreatic tissue, muscle tissue (such as cardiac muscle), liver, skin, intestine, nasal epithelium, bone, pancreas, or germ cells, for example. A skilled artisan recognizes that the culture media may be supplemented with growth factors to facilitate culturing or expansion, appropriate to the cells/tissue from which the stem cells originally derive or appropriate to the cells/tissue to which the stem cells will differentiate. For example, for embryonic stem cells, expansion factors ex vivo may include one or more of the following: FGF-β, Wnt-3a, collagen, fibronectin, and laminin. For mesenchymal stem cells, for example, expansion factors ex vivo may include one or more FGF-β, EGF, PDGF, and fibronectin. For haematopoietic stem cells, expansion factors ex vivo may include one or more of IL-3, IL-6, stem cell factor (SCF), β-mercaptoethanol, Flt-3/Flk-2, Tpo, Shh, Wnt-3a, and Kirre. For neural stem cells, ex vivo expansion factors may include one or more of FGF-β, EGF, fibronectin, and cystatin C. For liver stem cells, expansion factors ex vivo may include one or more of leukemia inhibitory factor, LIF, IL-3, SCF, and Flt-3 ligand. For cardiac muscle stem cells, expansion factors ex vivo may include fibronectin. For intestinal stem cells, expansion factors ex vivo may include macrophage colony-stimulating factor and granulocyte-macrophage colong-stimulating factor. For pancreatic stem cells, expansion factors ex vivo may include FGF. A skilled artisan recognizes that analogous suitable reagents may be applied for any particular type of stem cells.

The cell culture method may be used to generate substantially pure populations of bone marrow (haematopoietic) stem cell in large numbers in mice as models for cell replacement therapy in the haematopoietic system, central nervous system (CNS), pancreatic islet system for insulin production, and in all systems where cell replacement is required for disease and degeneration recovery. In humans, the cell culture method can be employed to generate pure populations of bone marrow stem cells from a patient for therapeutic cell replacement in the haematopoietic system, CNS, pancreatic islet insulin producing system and other tissues where cell replacement is required.

In particular embodiments, the cell culture system yields pure populations of bone marrow stem cells, such as CD34+ or CD34− cells, in large numbers that have been grown in continuous cultures for at least ten months and can be expanded from microliters of cells to thousands of liters of cells. The cells are grown in the absence of serum, matrix, or feeder cells, unlike the requirements of growth for human embryonic stem cells and mouse embryonic stem cells; however, in alternative embodiments the cells are grown in the presence of serum. There is no possibility of pathogen transfer from simian feeder cells to the stem cells as there is in embryonic stem cell culture. This culture system allows adult (or any age) patients to use their own stem cells, such as bone marrow stem cells, for therapeutic cell replacement. The inventors have demonstrated that haematopoietic stem cells obtained, for example, by this culture method have a potential to develop into mature cells other than their normal lymphoid and myeloid products. They can become neurons, astroglia and oligodendroglia when implanted into adult brain. This method solves the problem of immune rejection of transplated cells, pathogen transfer (e.g. hepatitis, HIV) from donor to host, limited availability of embryonic and fetal stem cells and the ethical issues of human embryonic and fetal stem cells.

In one embodiment of the invention, there is a method of enriching proliferating cells in a plurality of cells, comprising the steps of providing a container having liquid cell culture medium comprising proliferating and non-proliferating cells; and passaging the suspended cells in liquid media, thereby excluding a plurality of the non-proliferating cells.

In another embodiment of the invention, there is a method of enriching stem cells in a plurality of cells, comprising the steps of adding a sample of cells to a first liquid cell culture medium under conditions wherein stem cells are in suspension in the first medium and non-proliferating cells adhere to a substrate; and passaging suspended cells into a second liquid cell culture medium. The stem cells may be further defined as pluripotent stem cells. In specific embodiments, the suspended cells are passaged more than once. The passaging of the suspended cells may be further defined as successively passaging the cells in liquid media in consecutive containers. Passaging of the cells may occur at any suitable frequency, although in specific embodiments it occurs at a frequency of about once a week, less than once a week, or more than once a week. In further specific embodiments, the passaging of the suspended cells thereby excludes at least a majority of the non-proliferating cells.

In additional embodiments of the invention, a plurality of the non-proliferating cells adhere to a substrate, such as the container housing the liquid cell culture medium. In a particular embodiment, the passaging of the suspended cells comprises transferring at least some of the medium from a prior container into a subsequent container. The transferred medium may comprise growth factors, cytokines, or a mixture thereof. In one specific embodiment, the cell culture medium comprises serum, although in an alternative embodiment the cell culture medium does not comprise serum. In specific embodiments, the medium lacks feeder cells, matrix, or both.

In particular embodiments, the plurality of cells comprise bone marrow cells, liver cells, neural cells, pancreatic islet cells, embryonic cells, mesenchymal cells, and/or muscle cells. In embodiments wherein the plurality of cells comprises bone marrow cells, the media comprises interleukin-3, interleukin-6, stem cell factor, Flt-3/Flk-2, Tpo, Shh, Wnt-3a, Kirre, or a mixture thereof. In other embodiments wherein the plurality of cells comprises neural cells, the media comprises FGF-β, EGF, fibronectin, cystatin C, or a mixture thereof. In still other embodiments wherein the plurality of cells comprises embryonic cells, the media comprises FGF-β, Wnt-3a, collagen, fibronectin, laminin, or a mixture thereof. In additional embodiments wherein the plurality of cells comprises mesenchymal stem cells, the media comprises FGF-β, EGF, PDGF, fibronectin, or a mixture thereof.

In another embodiment of the invention, the methods further comprise the step of delivering one or more of the stem cells to an individual.

In an additional embodiment of the invention, there is a method of providing therapy to an individual in need thereof, comprising the steps of obtaining one or more stem cells as produced by a method of enriching stem cells in a plurality of cells by adding a sample of cells to a first liquid cell culture medium under conditions wherein stem cells are substantially in suspension and wherein non-proliferating cells substantially adhere to a substrate; and passaging suspended cells from the first medium into a second liquid cell culture medium, thereby enriching the stem cells; and delivering the one or more stem cells to the individual. The stem cells may be capable of differentiating into bone marrow cells, neural cells, pancreatic cells, skin cells, hair follicle cells, bone cells, intestinal cells, or cardiac muscle cells, for example. The stem cells may be delivered by injection or implantation. In specific embodiments, the individual has multiple sclerosis, diabetes, Parkinson's disease, amyotrophic lateral sclerosis, Down Syndrome, Alzheimer's disease, heart disease, Huntington's Disease, stroke, spinal cord injury, leukemia, aplasia, requires skin replacement, or requires hair follicle replacement.

In some embodiments, the method is further defined as the cells comprising one or more therapeutic agents. The therapeutic agent may comprise an expression vector comprising a nucleic acid encoding the therapeutic agent. In a specific embodiment, the therapeutic agent is a neuroprotective factor, such as interferon-beta or brain derived growth factor.

In one embodiment of the invention, there is a method of enriching stem cells in a plurality of cells, comprising the steps of adding a sample of cells to a first liquid cell culture medium under conditions wherein stem cells are substantially in suspension and wherein non-proliferating cells substantially adhere to a substrate; and passaging suspended cells from the first medium into a second liquid cell culture medium, thereby enriching the stem cells. In a specific embodiment, the stem cells are further defined as pluripotent stem cells.

As used herein, the term "substantially in suspension" refers to a plurality of stem cells being in suspension in a liquid culture. Although in specific embodiments a small amount of stem cells may adhere to a substrate, in particular embodiments, at least about 10%, 20%, 30%, 40%, 50%, 60%, 70%, 80%, 90%, 95%, 97%, 99%, or 100% of the stem cells are in suspension in a liquid culture. In further embodiments, "substantially in suspension" refers to the majority of stem cells being in suspension in a liquid culture. As used herein, the term "substantially adhere to a substrate" refers to a plurality of non-stem cells adhering to a substrate. Although in specific embodiments a small amount of non-stem cells may be in suspension in a liquid culture, in particular embodiments, at least about 10%, 20%, 30%, 40%, 50%, 60%, 70%, 80%, 90%, 95%, 97%, 99%, or 100% of the non-stem cells are adherent to a substrate. In further embodiments, "substantially adhere to a substrate" refers to the majority of non-stem cells adhering to a substrate. In a specific embodiment, the substrate is the container that houses the first liquid cell culture medium.

In a particular embodiment of the invention, the suspended cells are passaged more than once. The passaging of the suspended cells may be further defined as successively passaging the cells in liquid media in consecutive containers. In particular embodiments, the passaging occurs at a frequency of about once a week, less than once a week, or more than once a week. In a specific embodiment, the first cell culture medium, the second cell culture medium, or both do not comprise serum. In particular, the culture medium lacks feeder cells, matrix, or both.

In a specific embodiment, the plurality of cells is further defined as comprising bone marrow cells, liver cells, neural cells, pancreatic islet cells, embryonic cells, mesenchymal cells, muscle cells, skin cells, hair follicle cells, intestinal cells, cardiac cells, or bone cells. In specific embodiments, when the plurality of cells comprises bone marrow cells the media comprises interleukin-3, interleukin-6, stem cell factor, Flt-3/Flk-2, Tpo, Shh, Wnt-3a, Kirre, or a mixture thereof. In specific embodiments, when the plurality of cells comprises neural cells the media comprises FGF-β, EGF, fibronectin, cystatin C, or a mixture thereof. In another specific embodiment, when the plurality of cells comprises embryonic cells, the media comprises FGF-β, Wnt-3a, collagen, fibronectin, laminin, or a mixture thereof. In an additional specific embodiment, when the plurality of cells comprises mesenchymal stem cells, the media comprises FGF-β, EGF, PDGF, fibronectin, or a mixture thereof. In a particular embodiment, one or more of the stem cells to an individual.

In another embodiment of the present invention, there is a method of treating an individual for a medical condition, comprising the steps of adding a stem cell-comprising sample of cells to a first liquid cell culture medium under conditions wherein the stem cells are substantially in suspension and wherein non-proliferating cells substantially adhere to a substrate; passaging the suspended cells from the first medium into a second liquid cell culture medium; and delivering one or more stem cells to the individual. In specific embodiments, the medical condition is multiple sclerosis, Parkinson's disease, diabetes, amyotrophic lateral sclerosis, Alzheimer's disease, Down Syndrome, cardiac disease, Huntington's Disease, stroke, spinal cord injury, leukemia, aplasia, skin replacement, or hair follicle replacement.

In particular embodiments, the passaging of the suspended cells is further defined as successively passaging the cells in liquid media in consecutive containers. In other embodiments, the delivering step of the one or more cells to the individual comprises injection or implantation, for example. In specific embodiments, the methods described herein further comprising the step of delivering one or more therapeutic agents to a stem cell prior to delivery of the one or more cells to the individual. The therapeutic agent may be any suitable therapeutic agent for the medical condition being treated, and in specific embodiments the agent comprises a nucleic acid, a peptide, a polypeptide, a small molecule, or a mixture thereof. In a specific embodiment of the invention, the individual has multiple sclerosis and the therapeutic agent comprises BDNF, GDNV, or IFN-β. In other specific embodiments, the individual has Parkinson's disease and the therapeutic agent comprises BDNF or GDNF. In another specific embodiment, the individual has diabetes and the therapeutic agent comprises insulin.

In another embodiment of the invention, there is a method of isolating one or more mammalian stem cells, comprising the steps of providing a plurality of cells, said plurality comprising one or more stem cells; subjecting the plurality of cells to a culturing step in a container comprising a liquid cell medium, said culturing producing suspended cells and container-adherent cells; transferring a plurality of suspended cells to another container comprising a liquid cell medium; and repeating the subjecting and tranferring steps at least once.

In particular embodiments of the invention, the ratio of suspended cells to adherent cells in a culturing step is greater than the ratio of suspended cells to adherent cells in a previous culturing step. In specific embodiments, the mammalian stem cells are further defined as pluripotent cells. In other specific embodiments, the adherent cells are further defined as differentiated cells. In particular embodiments, the transferring step further includes transferring at least some of the medium. The medium may lack serum, feeder cells, matrix, or combinations thereof.

In an additional embodiment of the invention, there are one or more isolated stem cells produced by the steps of adding a sample of cells to a first liquid cell culture medium under conditions wherein stem cells are substantially in suspension in the first medium and wherein non-proliferating cells substantially adhere to a substrate; and passaging suspended cells into a second liquid cell culture medium.

In another embodiment of the invention, there is a method of treating an individual for a medical condition, comprising the steps of adding a stem cell-comprising sample of cells to a first liquid cell culture medium under conditions wherein the stem cells are substantially in suspension and wherein non-proliferating cells substantially adhere to a substrate; passaging the suspended cells, said suspended cells comprising one or more stem cells, from the first medium into at least a second liquid cell culture medium; delivering one or more therapeutic agents to one or more of the stem cells, wherein the therapeutic agent is suitable for the condition; and delivering one or more therapeutic agent-comprising stem cells to the individual. In a particular embodiment, the therapeutic agent comprises a therapeutic polynucleotide.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

In FIG. 19A, there is a graph representing the percentage of cleaved caspase 3 cells in cultures of HSC from diploid and Ts65Dn mice (MEAN±SEM). In Ts65Dn, the number of apoptotic cells is higher than in diploid. In FIG. 19B, western blots showed presence of p53 protein in Ts65Dn mice and uncleaved caspase 3 protein in diploids and trisomic HSC cultured 6 weeks. TA, TC, TB1, TB2—individual trisomic mice. DA, DE, DF—individual diploid mice. In FIG. 19c, there are color images showing Dapi nuclear staining and immunostaining for anti-caspase3 and anti-p53.

FIG. 21 shows mitotic and apoptotic markers in diploid and Ts65Dn hematopoietic bone marrow cells in vivo. Double labeling for CD34+ and TUNEL, cleaved caspase 3 showed higher death in trisomic HSCs than in diploid. Staining for CD34+ and Ki67 showed higher proliferation in diploid HSCs.

DETAILED DESCRIPTION OF THE INVENTION

Figure 1:
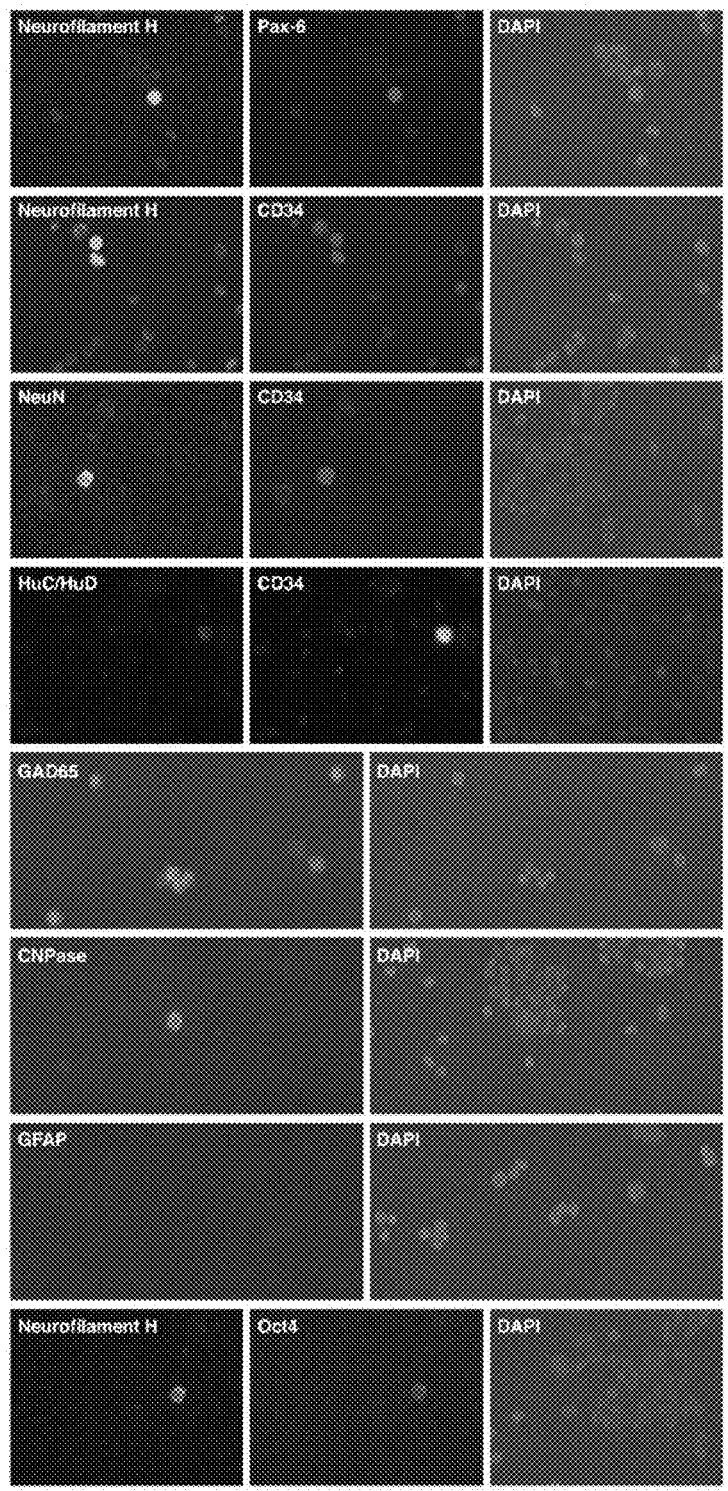
FIG. 1 shows expression of neural genes in a subset of adult mouse whole ex vivo bone marrow. Double immunocytochemical detection of neurofilament H and Pax-6 in the same subset of bone marrow cells. Expression of neuronal neurofilament H, NeuN and HuC/HuD in a subset of CD34+ bone marrow cells. GAD65, an enzyme responsible for synthesis of a major neurotransmitter, also was present in a subset of bone marrow cells. Oligodendroglial CNPase was detected in a subset of bone marrow cells whereas no astroglial marker, GFAP, was detected on ex vivo bone marrow. Neurofilament H and Oct-4 were detected in the same subset of ex vivo bone marrow cells. DAPI stains the nuclei of all cells.

The term "a" or "an" as used herein in the specification may mean one or more. As used herein in the claim(s), when used in conjunction with the word "comprising", the words "a" or "an" may mean one or more than one. As used herein "another" may mean at least a second or more.

I. The Present Invention

The present invention concerns the enrichment, isolation, or culturing of proliferating cells to the exclusion of non-proliferating cells. In more specific terms, it concerns the enrichment, isolation, or culturing of stem cells, which may be further defined as pluripotent cells, to the exclusion of non-stem cells. The invention exploits the property of most differentiated cells to adhere to a substrate and/or another cell. In particular embodiments, the stem cells are obtained from bone marrow cells, although any suitable tissue comprising stem cells may provide the original plurality of cells from which the stem cells are isolated.

Existing methods for obtaining human stem cells for therapeutic cell replacement include, for example, purifying cells by flow cytometry and by growing them in growth medium containing serum on a feeder layer of primate cells. In specific existing methods, the existing methods purify CD34+ cells from bone marrow or from peripheral circulating blood by flow cytometry and grow human embryonic stem cells in growth medium containing fetal bovine serum on a feeder layer of primate cells. Because stem cells are grown in the presence of non-human cells and foreign serum they are not suitable for re-implanting into patients. Furthermore, double sorting CD34+ cells by flow cytometry is tedious, gives yields of low abundance and presents sterility problems. The culture method of the present invention solves these problems and, thereby, provides stem cells that can be re-implanted into the donor.

Pure cultures of stem cells, such as the exemplary haematopoietic stem cells, are derived by continuous growth in liquid culture medium in the absence of methyl cellulose, matrigel, blood clot, or other matrix. Only suspension cells are passaged by removing suspended cells and conditioned medium from stromal cells, macrophages, endothelial cells and other cells that attach to the wall of the culture flask. Suspension cells are passaged with cell-conditioned medium into fresh culture flasks containing fresh culture medium. Alternatively, the exemplary haematopoietic stem cells are grown in defined serum-free medium.

The present invention provides a wealth of advantages over other methods for cell culture and cell application. Patients may use their own bone marrow to generate stem cells for therapeutic cell replacement. A patient's bone marrow can be expanded to provide a pure population of haematopoietic stem cells, and clonal stem cells can be derived. Culturing a patient's stem cells in the conditions of the invention for cell replacement therapy avoids immune rejection, HIV, hepatitis or other pathogen transfer and other animal virus contamination from fetal bovine serum or primate feeder cell exposure. Also, generating the exemplary haematopoietic stem cells in the manner of the invention avoids purifying very low abundance CD34+ cells by flow cytometry from bone marrow or peripheral blood. To date, flow cytometry is the only technology to obtain pure populations of CD34+ stem cells and the yield is low, whereas the present invention yields high abundanct ($10^9$) stem cells. Flow cytometry is tedious, slow, expensive and cells are easily contaminated. Finally, obtaining abundant populations of pure CD34+ (for example) stem cells from mice provides a rodent model to study the differentiation of haematopoietic stem cells into neurons, glia, oligodendrocytes, insulin-producing pancreatic islet cells, etc. In addition, these cells can be used in the mouse model to investigate cell transplantation for therapeutic cell replacement.

Exemplary applications for therapeutic cell replacement with CD34+ haematopoietic stem cells include immune diseases, such as, for example, arthritis, lupus, type I diabetes, etc.; cancer, such as leukemia; multiple sclerosis; Parkinson's disease; Alzheimer's disease; other degenerative neurological diseases; spinal cord injury; pancreatic islet cell replacement; and so forth.

Bone marrow, or cells selected from bone marrow, recently were reported to give rise to cells with a neural phenotype, after in vitro treatment with neural inducing factors or after delivery into the brain. However, the present inventors previously showed that untreated bone marrow cells express products of the neural myelin basic protein gene and herein demonstrate that a subset of ex vivo bone marrow cells expresses the neurogenic transcription factor, Pax-6, as well as, neuronal genes: neurofilament H, NeuN, HuC/HuD and GAD65 and the oligodendroglial gene, CNPase. In contrast, astroglial GFAP was not detected. These cells also were CD34+, a marker of haematopoietic stem cells. Cultures of these highly proliferative CD34+ cells, derived from adult mouse bone marrow, uniformly displayed a phenotype compatible to that of haematopoietic progenitor cells (CD45+, CD34+, Sca-1+, AA4.1+, cKit+, GATA-2+ and LMO-2+). The neuronal and oligodendroglial genes expressed in ex vivo bone marrow, also were expressed in all cultured CD34+ cells, and again GFAP was not observed. After CD34+ cell transplantation into adult brain, neuronal or oligodendroglial markers segregated into distinct non-overlapping cell populations, while astroglial GFAP appeared, in the absence of other neural markers, in a separate set of implanted cells. Thus, neuronal and oligodendroglial gene products are present in a subset of bone marrow cells and the expression of these genes can be regulated in brain. The fact that these CD34+ cells also express transcription factors (Rex-1 and Oct-4) found in early development indicates, in specific embodiments, that they are pluripotent embryonic-like stem cells.

In addition, bone marrow comprises both CD 34+ stem cells as well as CD 34+ non-stem cells, which are cells that are determined to differentiate into a particular progeny. Therefore, bone marrow stem cells may be derived by flow cytometry by repeated sorting with a panel of antibodies to markers of stem cells vs. differentiated cells. Nevertheless, it is known that flow cytometry-sorted stem cells are a mixed population with contaminating cells. The present invention avoids the contamination of non-stem cells by providing a substantially pure culture of stem cells. This may be defined as having 100% homogenous population of stem/progenitor cells with no contaminating cells, although in alternative embodiments there are miniscule amounts of non-stem cells.

II. Stem Cells

Stem cells are cells that have the capacity to become at least all differentiated cell types of their lineage in that tissue. Stem cells have two important characteristics that distinguish them from other types of cells. First, they are unspecialized cells that renew themselves for long periods through cell division. Secondly, under suitable conditions they can be induced to become cells with special functions, which may be considered differentiated.

Stem cells may be further defined as those cells that are self-renewing that undergo symmetric and asymmetric divisions to self-renew or differentiate into multiple kinds of differentiated progeny (Lin et al., 1997; Morrison et al., 1997; Burns and Zon, 2002).

In specific aspects of the invention, stem cells are cells that are not terminally differentiated and as a result are able to produce cells of other types. In particular aspects of the invention, they are used to repair specific tissues or to grow organs de novo, for example. There are at least three types of stem cells: totipotent, pluripotent, and multipotent. A single totipotent stem cell can grow into an entire organism. Pluripotent stem cells cannot grow into a whole organism, but they can become any other cell of a particular germ layer, such as ectoderm, mesoderm, or endoderm. Multipotent (also referred to as unipotent) stem cells can become all cells of a given tissue derived from one of the germ layers; however, multipotent in alternative embodiments refers to stem cells having the potential to become only two differentiated cell types.

Stem cells have been identified in a variety of tissues. They can be distinguished in a variety of means, such as by the tissue from which they were harvested, their bias in differentiation ability, the stage of development at which they exist, and their gene expression profile. In particular, stem cells may be from ectoderm (epidermal, neural, neural crest, and hair follicle); mesoderm (cardiac muscle, skeletal muscle, umbilical cord blood, mesenchymal, hematopoietic, umbilical cord matrix, and multipotent adult precursor); endoderm (pancreatic islet and hepatic oval); and germ (primordial germ) stem cells. More than one stem cell may be present in a particular tissue. For example, in the hematopoietic system alone, there are stem cells from the yolk sac, fetal cord blood, liver, and adult bone marrow.

III. Culture Medium

A skilled artisan recognizes that suitable culture media is used in the present invention such that stem cells may proliferate and preferably such that stem cells may be distinguished from non-stem cells, such as differentiated cells. Many suitable media are available commercially, such as from Invitrogen-GIBCO BRL (Carlsbad, Calif.) or Sigma (St. Louis, Mo.), for example. The media utilized may be serum-free or serum-comprising, although a skilled artisan recognizes that it may be advantageous to use serum-free media so that the cells are not exposed to one or more pathogens.

In specific embodiments, culture media is utilized for culturing stem cells wherein the media is conventionally used for the culturing of progeny of stem cells, although alternatively it is media that is not conventionally used for the culturing of progeny of stem cells. In further specific embodiments, media considered suitable for culturing progeny of bone marrow stem cells is employed, such as, for example, hybridoma serum-free media. In particular embodiments hybridoma serum-free media may comprise low amounts of protein (such as about 20 µg/ml or less of protein, such as the exemplary insulin, transferrin, and/or albumin). The media of the invention, such as the serum-free hybridoma media, may lack L-glutamine, antibiotics, antimycotics, and phenol red, for example.

For embodiments concerning hematopoietic stem cell expansion or umbilical cord blood stem cell expansion, for example, Stemline™ Hematopoietic Stem Cell Expansion Medium (Sigma; St. Louis, Mo.) may be employed. In other embodiments, Hybridoma Medium Animal Component-Free Medium (Sigma; St. Louis, Mo.) is utilized. As such, the media may comprise inorganic salts, essential and non-essential amino acids, vitamins, sodium bicarbonate, HEPES, trace elements, fatty acids, and other organics. Recombinant human insulin may be present as the only source of protein. The medium may lack L-glutamine, antibiotics, and phenol red, for example.

More specifically, exemplary culture media includes one or more of the following, such as inorganic salts (including, for example, $CaCl_2$; $Fe(NO_3)_3.9H_2O$; KCl; $MgSO_4$ (anhydr.); NaCl; $NaHCO_3$; $NaH_2PO_4.H_2O$); amino acids (essential and/or non-essential) (including, for example, L-arginine-HCl, L-cystine; L-cystine.2HCl; L-glutamine; L-alanyl-L-glutamine; glycine; L-histidine $HCl.H_2O$; L-isoleucine; L-leucine; L-Lysine-HCl; L-methionine; L-phenylalanine; L-serine; L-threonine; L-tryptophan; L-tyrosine; L-tyrosine-$2Na.2H_2O$; L-valine); vitamins (including, for example, D-Ca pantothenate; choline chloride; folic acid; i-Inositol; niacinamide; riboflavin; thiamine HCl; Pyridoxine HCl, for example); trace elements (including ammonium metavanadate; cupric sulfate; manganous chloride; sodium selenite, for example); proteins (including AlbuMAX®II (bovine serum albumin; Life Technologies, Inc.; Gaithersburg, Md.), insulin (preferably recombinant), and human transferrin (Holo), for example); and other components (including D-glucose; phenol red; HEPES; and sodium pyruvate, for example).

A skilled artisan recognizes that the culture media may be supplemented with growth factors to facilitate culturing or expansion, appropriate to the tissue from which the stem cells originally derive or to the tissue for which they will differentiate into. For example, for embryonic stem cells, expansion factors ex vivo may include one or more of the following: FGF-β Wnt-3a, collagen, fibronectin, and laminin. For mesenchymal stem cells, for example, expansion factors ex vivo may include one or more FGF-β EGF, PDGF, and fibronectin. For haematopoietic stem cells, expansion factors ex vivo may include one or more of IL-3, IL-6, SCF, Flt-3/Flk-2, Tpo, Shh, Wnt-3a, and Kirre. For neural stem cells, ex vivo expansion factors may include FGF-β, EGF, fibronectin, and cystatin C.

In some embodiments, the media includes at least some media transferred from a previous culture media, which may be considered to be "conditioned," wherein cells have previously secreted useful agents such as growth factors and cytokines into the media. Any agents that facilitate growth of the stem cells in the media and/or any agents that enhance the ability to distinguish the suspended cells from the adherent cells are useful in the invention. Specific examples of conditioning agents may be dependent upon the tissue from which the original plurality of cells were derived for the isolation of the stem cells. Exemplary growth factors and cytokines include leukotrienes; second messengers (e.g. cAMP, cGMP); growth factor EGF, FGF, PDGF, BMP, GDNF; or interleukins other than IL-3 an IL-6 provided by the medium (e.g. IL-1, IL-2, IL-4, IL-5, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29); and vitamins. In alternative embodiments, these growth factors and cytokines are not obtained from the conditioned media but are added exogenously, although they may also be used to supplement conditioned media having the same or different agents.

In particular embodiments, defined serum-free medium (Hybridoma SFM medium, GIBCO BRL, Rockville, Md., USA) comprising interleukin 3, interleukin 6, stem cell factor and β-mercaptoethanol is employed. Other medium include Dulbecco's Modified Eagle's Medium containing 10% fetal bovine serum and interleukin 3, interleukin 6, stem cell factor, and β-mercaptoethanol.

IV. Cell Markers

Cell markers are useful identification tools for particular desired stem cells. As used herein, the term "cell marker" refers to a gene or gene product commonly associated with a stem cell of interest. The gene product may be expressed on the cell surface.

Cell markers may be lineage markers, metabolic markers, communication markers, growth factors, transcription factors, and so forth, for example. In specific embodiments, specific cell markers are associated with particular desired stem cells. For example, one or more cell markers may be indicative of one kind of stem cell, whereas other one or more cell markers are indicative of another kind of stem cell. In alternative embodiments, there are one or more cell markers that are indicative of more than one kind of stem cell. Examples of cell markers for more than one stem cell may include ALDH activity, Hoescht 33342/SP, ABCG-2 expression, rhoda-mine 123 exclusion, connexin expression, and/or lack of lineage markers (Lin−) (Cai et al., 2004, incorporated by reference herein in its entirety).

Identification of one or more cell markers may be of any suitable method, so long as the marker is detectable if present. In particular embodiments, cell markers are identified by immunocytochemistry, in situ hybridization, polymerase chain reaction, protein polyacrylamide gel electrophoresis, western blot analysis, or a combination thereof.

A skilled artisan recognizes how to determine a particular suitable one or more cell markers prior to isolation based on the above-mentioned procedures. In specific embodiments, for human embryonic stem cells suitable markers include Nanog, GTCM-1, connexin 43 (GJA1), oct-4, and TDGF1 (cripto), for example (Bhattacharya et al., 2004). In other embodiments, skilled artisans recognize that a set of particular tissue cell markers from one mammalian species may not be identical to the same tissue's cell markers in another mammalian species.

Exemplary cell markers for hematopoietic stem cells include CD34+, Sca-1+, AA4.1+ and cKit+, and in specific embodiments these markers denote murine hematopoietic stem cells. In alternative embodiments, human hematopoietic stem cells may be CD34+ or CD34−, CD38+, CD38(−), ckit+, Thy $1^{10}$, ClFR+, or a combination thereof. Exemplary markers for neural stem cells include epidermal growth factor, fibroblast growth factor, and so forth, for example. Exemplary markers for cardiac stem cells include stem cell antigen-1, CD45(−), CD34(−), Sca1+, or a combination thereof, for example. Intestinal stem merkers include A33+, cFMS+, c-myb+, CD45(−), or a combination thereof, for example. Skin stem cell markers include keratin 19, for example.

V. Applications of Cells of the Invention

The present invention concerns stem cells and their uses, such as for research or for therapeutic uses for an animal in need thereof, such as with cell replacement therapy. The cells may be therapeutic as they were collected, or they may be manipulated prior to their application. Such manipulations may be of any kind to enhance their therapeutic activity for the individual(s) to which they are applied. In particular embodiments, the stem cells further include a therapeutic agent, such as a small molecule, therapeutic polypeptide, a nucleic acid encoding a therapeutic polypeptide, siRNA, antisense RNA, RNAi, lipids, including phospholipids, proteolipids and glycolypids, or a mixture thereof. In a specific embodiment, the therapeutic agent provides amelioration of at least one symptom of a medical condition, and/or prevents at least one symptom of a medical condition. The particular stem cells utilized in this aspect of the invention are suitable for their intended purpose. Example applications such as those that follow may be employed, although a skilled artisan recognizes other suitable applications may be utilized.

A. Haematopoietic System

Stem cells from the haematopoietic system may be employed for a variety of applications. The stem cells may be utilized in preventing and/or treating Down syndrome, for example by applying one or more cells of the invention to an individual (including a fetus) suffering therefrom or to an individual susceptible to Down syndrome, such as a fetus. In other embodiments, the haematopoietic system benefits from cell replacement therapy, such as when the individual suffers from a blood disorder, including leukemia.

Indeed, herein the present inventors report that neural and oligodendroglial genes are expressed in a subset of ex vivo bone marrow cells that are CD34 positive. A culture system was developed to generate pure populations of highly proliferative cells from adult bone marrow that express both neural and haematopoietic stem cell markers, in addition to CD34. Upon transplantation into adult mouse brain, the cultured CD34+ cells survive for fourteen months, the longest time tested, and differentiate morphologically into cells that resemble neurons, astrocytes and oligodendrocytes and express distinct markers specific for each of these cell types. However, in alternative embodiments, the cells are CD34−.

Monitoring of the applied stem cells may be by any suitable means, such as by monitoring particular cell markers and/or characterizing morphology, for example. For example, the cells may be monitored for Neurofilament H, M, L, MAP2, β-tubulin, NeuN, tyrosine hydroxylase, acetylcholine transferase, glutamic acid decarboxylase, dopamine, β-hydroxylase, synatin, synaptobrevin, GFAP, CNPase, MOSP, myelin basic protein, MOG, MAG, PLP, or a combination thereof.

B. Central Nervous System (CNS)

The stem cells of the present invention may also be applied to individuals suffering from a disorder of the central nervous system, including those having neurodegenerative disorders, such as Parkinson's disease, multiple sclerosis, Alzheimer's disease, and amyotrophic lateral sclerosis (ALS), stroke, spinal cord injury, Huntington's disease for example. In particular embodiments, an individual's own bone marrow provides stem cells for therapeutic cell replacement for that patient's neurodegenerative disorder.

In particular embodiments, the stem cells are applied to a neurogenic region of the brain, such as the hippocampus, or a non-neurogenic region of the brain, such as the striatum. In particular embodiments, the cells develop into neurons, astrocytes, glia, and oligodendrocytes, such as those that produce myelin and form myelin sheaths around CNS axons, for example.

In further embodiments, stem cells employed for a CNS application comprise a nucleic acid a therapeutic agent, such as encoding interferon-beta or brain derived neurotrophic factor, which is known to be neuroprotective; alternatively, the stem cells harbor a therapeutic polypeptide or small molecule, for example. Other neuroprotective agents include, glial derived neurotrophic factor (GDNF), NGF, FGF, EGF, BMP, TNF-α, for example, which may also be provided in the form of a polypeptide or a nucleic acid encoding the polypeptide, for example. In specific embodiments, the nucleic acid is RNAi, siRNA, or antisense RNA.

Monitoring of the applied stem cells prior to and/or following a CNS application may be by any suitable means, such as by monitoring particular cell markers and/or characterizing morphology, for example. For example, the cells may be monitored for tyrosine hydroxylase, HuC/HuD, neurofilament H, NeuN, M2 muscarinic acetylocholine receptor, Pax6, and/or GAD65. Astrocytes may be monitored for GFAP, for example. Oligodendrocytes may be monitored for CNPase, MOSP, NG2, galactocerebroside, or O4, for example.

A specialized CNS embodiment for the invention includes use of the cells for retinopathies (see below).

C. Pancreatic Islet System

In an additional embodiment, stem cells of the present invention are employed in a pancreatic islet system, such as for cell replacement therapy for diabetes. In particular, the cells for utilization in such an embodiment regulate insulin synthesis naturally, although in some embodiments insulin synthesis is not detected until following in vivo differentiation into pancreatic islet Beta-cells. In further embodiments, the cells are genetically engineered, for example, to regulate expression of insulin. This may be accomplished by any suitable means, such as harboring a nucleic acid that encodes insulin, for example.

Monitoring of the applied stem cells prior to and/or following a pancreatic application may be by any suitable means, such as by monitoring particular cell markers and/or characterizing morphology, for example. For example, the cells may be monitored for production of insulin and/or pancreatic islet beta cell glucose-sensing molecules.

D. Retinopathies

As described elsewhere herein, the stem cells and methods of the present invention are useful for application to individuals with retinopathies. Retinopathies include deficiencies of the retina, a part of the CNS, and particular classes of neural cells may be lost; for example, photoreceptors are defective in macular degeneration, such as age-related macular degeneration; retinitis pigmentosa, Leber's congenital amaurosis, rod monochromomacy and X-linked progressive cone dystrophy; ganglion cells are defective in multiple sclerosis and methanol toxicity; M class ganlion cells are defective in glaucoma, Alzheimer's disease and hydrocephalus; and Muller cells are defective in adult retinoschisis.

Monitoring of the applied stem cells prior to and/or following retinopathy application may be by any suitable means, such as by monitoring particular cell markers and/or characterizing morphology, for example. For example, the cells may be monitored for the retinal stratum of implant and molecular markers of cell class, e.g. opsin, Thy 1, glutamine synthetase and an array of neurotransmitters and neuropeptides.

E. Other Systems

In other embodiments, stem cells encompassed by the present invention are utilized in another exemplary embodiment. For example, stem cells for muscle may be utilized for a suitable muscular application, whether it is smooth muscle or skeletal muscle. In one example, stem cells from muscles are employed to apply to a cardiac application, such as for the prevention and/or treatment of heart disease, including heart failure. The cells may be applied upon diagnosis of a heart ailment, following diagnosis of a heart ailment, or to an individual susceptible to contracting heart disease.

In specific embodiments, the stem cells of the present invention are applied to an individual in need thereof for a cardiac purpose, wherein the stem cells comprise a therapeutic agent. The therapeutic agent may comprise a small molecule, a nucleic acid encoding a therapeutic polypeptide, a therapeutic nucleic acid, such as an RNAi molecule, an siRNA, or antisense RNA, or a therapeutic polypeptide. The therapeutic agent may be secreted upon application to the individual, such as to provide therapeutic benefit to endogenous cells of the individual. Exemplary embodiments of therapeutic agents for stem cells in cardiac applications include VEGF+.

Hematopoietic system in leukemias after therapeutic irradiation, aplasia, genetic blood diseases (matched donor stem cells), myelodysplasia, dermis replacement (such as for burn), and bone replacement (such as for osteoporosis and other bone loss/degenerative conditions) are other systems/diseases that would benefit from stem cells of the invention.

VI. Gene Therapy Administration

In some embodiments of the present invention, the stem cells are utilized themselves as being therapeutic, although in other embodiments the stem cells are employed as a vehicle for delivery of a therapeutic agent. In further embodiments, the stem cells are both therapeutic and provide a therapeutic agent.

In particular, the method of cell therapy of the invention provides a cell comprising a copy of a nucleic acid sequence or amino acid sequence for therapy of a disease.

In an embodiment of the present invention the cells and methods of the present invention are utilized for gene therapy. For gene therapy, a skilled artisan would be cognizant that the cell contains a vector wherein the gene of interest is operatively limited to a promoter, and in particular embodiments the promoter is specific for the tissue to which the cell will be associated with upon differentiation. For example, in neural-specific applications, a neurofilament promoter may be utilized. For astroglia, a GFAP promoter may be employed. For oligodendroglia, MGP, MOG, or MAG promoters may be used.

The promoter may be consitutive, inducible or tissue-specific. One skilled in the art recognizes that in certain instances other sequences such as a 3' UTR regulatory sequence is useful in expressing the gene of interest. Means known in the art can be utilized to prevent release and absorption of the composition until it reaches the target organ or to ensure timed release of the composition. A sufficient amount of vector comprising the therapeutic nucleic acid sequence is administered to provide a pharmacologically effective dose of the gene product.

In specific embodiments, the expression construct further comprises a therapeutic nucleic acid having a nuclear localization signal and/or the therapeutic gene product comprises a protein transduction domain.

One skilled in the art recognizes that different methods of delivery may be utilized to administer a vector into a cell of the present invention. Examples include: (1) methods utilizing physical means, such as electroporation (electricity), a gene gun (physical force) or applying large volumes of a liquid (pressure); and/or (2) methods wherein said vector is complexed to another entity, such as a liposome or transporter molecule.

Accordingly, the present invention provides a method of transferring a therapeutic gene to a host, which comprises administering the vector inside a cell of the present invention. Effective gene transfer of a vector to a host cell in accordance with the present invention can be monitored in terms of a therapeutic effect (e.g. alleviation of at least one symptom associated with the particular medical condition being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody mediated detection, mRNA or protein half life studies, or particularized assays to detect protein or polypeptide encoded by the transferred nucleic acid, or impacted in level or function due to such transfer, or combinations thereof). In other embodiments, the presence of particular cell markers are assayed, such as by immunocytochemistry.

These methods described herein are by no means all inclusive, and further methods to suit the specific application will be apparent to the ordinary skilled artisan. Moreover, the effective amount of the compositions can be further approximated through analogy to compounds known to exert the desired effect and/or upon empirical observations, for example.

Furthermore, the actual dose and schedule can vary depending on whether the cells are administered in combination with other pharmaceutical compositions, or depending on interindividual differences in pharmacokinetics, drug disposition, and metabolism. Similarly, amounts can vary in in vitro applications depending on the particular cells utilized. Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

In a specific embodiment the nucleic acid for therapy is a DNA or a RNA, and it is within the scope of the present invention to include any nucleic acid for a therapeutic purpose within the cells. Specific examples include but are not limited to interferon-beta or brain derived growth factor, such as for neurological applications, as well as GDNF, NGF, FGF, and BMP. The dystrophin nucleic acid, such as for the treatment of muscular dystrophy; or the beta-globin gene, such as for the treatment of sickle cell anemia may also be employed.

In a specific embodiment the nucleic acid for therapy is p53, which is often mutated in cancer. Alternatively, as is taught by Foster et al. (1999), herein incorporated by reference, a compound to stabilize the DNA binding domain of p53 in an active conformation is furthermore delivered via cells or methods of the present invention to enable a mutant p53 in a tumor cell to activate transcription and slow tumor growth. In a specific embodiment the compound for stabilization comprises a hydrophobic group containing at least one cyclic group joined by a linker to an ionizable group, such as an amine.

Thus, a potential advantage of stem cells in addition to cell replacement therapy is that they can be genetically engineered in vitro to produce beneficial proteins. The present inventors have delivered two neuroprotective genes, Interferon-beta (IFN-β) and Brain Derived Neurotrophic Factor (BDNF), to mouse brain with genetically engineered bone marrow stem cells. BDNF is a pleiotrophic cytokine of the neurotrophin family, which plays an important role in regulating the survival and differentiation of various neuronal populations including dopaminergic, sensory, cerebellar and motor neurons. BDNF is thought to exert its biological activity by binding to the membrane-transversing tyrosine kinase TrkB receptor and activating several signal transduction pathways. In addition to regulating neuronal survival, proliferation, differentiation and neurite outgrowth, BDNF modulates oligodendrocyte proliferation and myelination of regenerating axons in experimental spinal cord injury. The phenotypes of BDNF knock out mice include balance problems associated with vestibular defects and feeding difficulties.

Based on these salutary effects of BDNF, its efficacy in preventing neuronal cell death after various forms of neuronal injuries and in animal models of neurodegenerative disease have been demonstrated (10,11). However, the major limitation of BDNF therapy is its short plasma half-life and inaccessibility to the CNS due to the blood-brain barrier. To circumvent this problem, gene therapy approaches can provide the potential for long-term delivery to the target tissue. BDNF expressed from a transgene and released in the extracellular milieu can diffuse locally and be taken up by neighboring nerve terminals for retrograde axonal transport.

Furthermore, the neuroprotective genes can be engineered to be under the control of gene promoters that allow expression of the BDNF gene product to be produced at a specific time and place. The present inventors have engineered the BDNF gene to be under the control of the TET-On promotor so the gene is expressed by transplanted stem cells carrying the gene when the recipient mouse is given tetracycline, such as in the drinking water, and stops producing BDNF when tetracycline is removed. Furthermore, the present inventors have separate BDNF-TET-On constructs with three different cell-type promoters: neurofilament for neurons, GFAP for astrocytes and MBP for oligodendrocytes. This allows control of the time of BDNF production in transplanted animals, and the cell-type promoters can express BDNF only by the stem cells that become neurons or astrocytes or oligodendrocytes. Thus, the stem cells offer two therapeutic tools, cells for cell replacement therapy and vehicles for tightly controlled gene therapy.

In other embodiments, the engineered stem cells are employed to deliver genes to three mouse models of neurodegeneration: two models of multiple sclerosis, EAE and Shiverer mice, and one Parkinson's Disease model of MPTP-treated mice.

VII. Kits of the Invention

In specific embodiments of the present invention, there are one or more kits for making and/or using the stem cells of the invention. The components of the kit are housed in a suitable container and may be sterile, where appropriate. Kit housing may include boxes, vials, or bottles, for example.

The kit may include the suitable media or ingredients thereof, and in some embodiments the media is serum-free, whereas in other embodiments the media comprises serum. The kit may include one or more containers for culturing of the stem cells, and it may further include a transfer means, such as pipets, for transferring the suspended cells. In other embodiments, there are components for application of the stem cells to an individual, such as a syringe, a filter for concentrating the cells, an aqueous solution for suspension of the cells, a needle, a syringe, and so forth.

In further embodiments, there are components in the kit for extracting cells from a tissue of interest for culturing of the stem cells, such as an apparatus for obtaining bone marrow. Examples include syringes, scalpels, and standard bone marrow aspiration kit of needle and syringe, with trocar containing heparin (commercially available). In embodiments wherein heparin is found to kill a subset of bone marrow stem cells, there may be a kit with the standard sterile syringe, aspirating needle, stylet, luer-lock adaptor and cleaning rod, etc., without heparin, and so forth.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

Bone Marrow CD34+ Stem Cell Cultures

Bone marrow was aseptically collected from the femurs of sixteen C57B1/6J, four SJL/J, four C3H and two 129FVB adult mice. Cells from one adult mouse femur were suspended in 10 ml of Dulbecco's Modified Eagle's Medium (DMEM) (GIBCO) containing 10% fetal bovine serum and in 10 ml of Hybridoma Cell Defined Serum-Free Medium (GIBCO) and distributed into two T75 tissue culture flasks. Both media were supplemented with mouse interleukin 3 (IL-3) (R&D Systems), mouse interleukin 6 (IL-6) (R&D Systems), mouse stem cell factor (SCF) (R&D Systems) and β-mercaptoethanol to a final concentration of 5 ng/ml IL-3, 10 ng/ml IL-6, 10 ng/ml SCF and a 1:1000 dilution of 10 μl β-mercaptoethanol in 2.9 ml HOH. No matrix, substrate or feeder cells were added to the liquid medium in the tissue culture flasks. Cells were grown at 37° C. in humidified 10% $CO_2$/90% air. Cells were observed and fed or passaged, as needed, two times per week. Cells were fed by addition of 5 ml of fresh medium to each flask. When the cell culture was dense enough to subculture, only the floating cells were collected, leaving behind the cells attached to the culture flask. These attached cells are bone marrow stromal cells, endothelial cells, macrophages, etc. Floating cells were subcultured in 50% conditioned medium from the previous culture and 50% fresh medium at $2 \times 10^6$ cells/10 ml. After 3-4 weeks, the cultures contain only dividing floating cells and the cells no longer differentiate into macrophages and other cells that attach to the flask.

RT-PCR

RNA was obtained from adult mouse bone marrow, from CD34+ cells cultured from 6 weeks to 4 months and from postnatal day 2 (P2) mouse brain and RT-PCR was performed by standard methodology using the following DNA primers: GATA-2 forward 5'ATGGAGGTGGCGCCTGAGCAGCCT3' (SEQ ID NO: 1), reverse CTGCCGCCTTCCATCTTCATGCTC3' (SEQ ID NO:2); LMO-2 forward 5'ATGTCCTCGGCCATCGAAAGGAAG3' (SEQ ID NO:3), reverse 5'GATGATCCCATTGATCTTGGTCCA3' (SEQ ID NO:4); Rex-1 forward 5'CACCATCCGGGATGAAAGTGAGAT3' (SEQ ID NO:5), reverse 5'ACCAGAAAATGTCGCTTTAGTTTC3' (SEQ ID NO:6); Oct-4 forward 5'CCGTGAAGTTGGAGAAGGTG3' (SEQ ID NO:7), reverse 5'TGATTGGCGATGTGATGTAT3' (SEQ ID NO:8); Flk-2 forward 5'CGTACCGAATGGTGCGAGGATCCC3' (SEQ ID NO:9), reverse 5'CATGGTTCACATGGATGGCCTTAC3' (SEQ ID NO:10); TAL-1 forward 5'GATGACGGAGCGGCCGCCGAGCGAGGCG3' (SEQ ID NO:11), reverse 5'CGCACTACTTTGGTGTGAGGACCA3' (SEQ ID NO:12); CD34 forward 5'CAGTATTTCCACTTCAGAGATGAC3' (SEQ ID NO:13), reverse 5'GTGTAATAAGGGTCTTCACCCAGC3' (SEQ ID NO:14), neurofilament H forward 5'ATTGGCTTTGGTCCGAGTCC3' (SEQ ID NO:15), reverse 5'GGGGGTTCTTTGGCTTTTAC3' (SEQ ID NO:16), neurofilament M forward 5'CTTTCCTGCGGCGATATCAC3' (SEQ ID NO: 17), reverse 5'TCCTCAACCTTTCCCTCAAT3' (SEQ ID NO: 18), and neurofilament L forward 5'GCAGAACGCCGAAGAGTGGT3' (SEQ ID NO:19), reverse 5'CGAGCAGACATCAAGTAGGA3' (SEQ ID NO:20). PCR products were separated by base pair size on gels by standard protocols.

Immunocytochemistry

Noncultured ex vivo adult mouse bone marrow cells and in vitro bone marrow cells from 6 day, 21 day, 28 day, 48 day, 56 day and 110 day cultures were incubated in 4% paraformaldehyde at 4° C. for 15 min., washed 3 times in Dulbecco's Phosphate Buffered Saline (PBS), applied to microscope slides by cytocentrifuge and used immediately or stored at −80° C. until use. Cells then were treated with 0.25% Tween-20 for 3 min at 21° C., washed 3 time in PBS and analyzed by standard immunocytochemistry methodology using the following antibodies: Primary antibodies CD34 (PharMingen 553731), Sca-1 (PharMingen 557403), AA4.1 (PharMingen 559158), cKit (Cymbus CBL1359), H-2K (PharMingen 553567), CD45 (PharMingen 553076), F4/80 (Serotec MCAP497), Pax-6 (Santa Cruz sc-11357), Oct-4 (Santa Cruz sc-9081), HuC/HuD (Molecular Probes A-21275), neurofilament H (Stemberger Monoclonals SMI 312, Chemicon AB1989), NeuN (Chemicon MAB377), GAD65 (Chemicon AB5082), M2 muscarinic acetylcholine receptor (Chemicon AB166-50UL), GFAP (Chemicon MAB3402, AB5040, AB5804), CNPase (Chemicon MAB326), MOSP (Chemicon MAB328), NG2 chondroitin sulfate proteoglycan (Chemicon AB5320), galactocerebroside (Chemicon AB142), oligodendrocyte marker O4 (Chemicon MAB345), MAG (Chemicon MAB1567), PLP (Chemicon MAB388). Secondary antibodies were FITC-F(ab')$_2$ donkey anti-rabbit (JacksonImmuno 711-096-152), TRITC-F(ab')$_2$ donkey anti-rat (JacksonImmuno 712-026-150), TRITC-F(ab')$_2$ goat anti-mouse IgG+IgM (JacksonImmuno 115-026-044), TRITC-F(ab')$_2$ rabbit anti-mouse (JacksonImmuno 315-026-045), FITC-goat anti-mouse IgG1 Fcγ fragment-specific (JacksonImmuno 115-095-008), Cy5-F(ab')$_2$ donkey anti-rabbit (JacksonImmuno 711-176-152), horseradish peroxidase-goat F(ab')$_2$ anti-rabbit IgG (H+L) (Caltag L4300-7), Fab fragment goat anti mouse IgG (JacksonImmuno 115-007-003). In the cases of mouse monoclonal IgG1 antibody binding to ex vivo mouse bone marrow cells the standard protocol was modified to expose fixed permeablized cells for 1 hr at room temperature to 5% normal goat serum in PBS, followed by six washes with PBS, then cells were exposed for 1 hr to 20 μg/ml Affinipure Fab fragment goat anti-mouse IgG1 (JacksonImmuno 115-007-003), then for 1 hr to primary mouse monoclonal antibody IgG1 to the antigens of interest, washed six times in PBS and finally exposed 1 hr to secondary FITC-goat anti-mouse IgG1 Fcγ fragment-specific, washed six times with PBS. Two controls were used: both no primary antibody and primary mouse monoclonal IgG1 anti-GFAP.

Western Blot Analysis

Proteins from cultured CD34+ cells were separated by 10%, 12% and 4-20% gradient polyacrylamide gel electrophoresis and transferred to nitrocellulose membranes as reported (Marty et al., 2002) and analyzed for specific proteins using the antibodies listed above.

Vital Dye Labeling of CD34+ Cells

CD34+ cells were labeled by fluorescent dye 5-(and 6)-(((4-chloromethyl)benzoyl)amino)tetramethylrhodamine (Cell Tracker Orange CMTMF) (Molecular Probes) as follows. CD34+ cells ($2 \times 10^8$) were incubated in a final concentration of 25 μM Cell Tracker Orange from a 400× stock of 10 mM dye in dimethylsulfoxide (DMSO). Cells were incubated in 5 ml of dye containing DMEM10 at 37° C. for 15 min., pelleted by centrifugation, washed in 15 ml $DMEM_{10}$, incubated 30 min. at 37° C., pelleted, washed again in 15 ml $DMEM_{10}$ at 37° C. for 15 min., pelleted and resuspended in DMEM10 at $10^4$ cells/μl.

Stereotactic Injection of CD34+ Cells Into Adult Mouse Brain

Thirty-four anesthetized adult C57B1/6J mice were stereotactically injected with 104 C57B1/6J Cell Tracker Orange labeled CD34+ cells in 1 μl DMEM10 into the hippocampus and striatum of each brain. Injected animals were grown for 1 to 14 months, then sacrificed, perfused with PBS followed by 4% paraformaldehyde. Brains were removed, equilibrated in 30% sucrose, embedded in cryo-embedding compound, frozen, cut into 30 μm thick cross-sections, prepared for immunohistochemistry using standard methods and counterstained with 25 ng/ml 4'-diamidino-2-phenylindole (DAPI). Implanted CD34+ cells were observed and images were captured by conventional fluorescence and laser confocal microscopy with rhodamine, fluorescein, Cy5 and DAPI optics.

Example 2

Neural Antigens Present in a Subset of Ex Vivo Bone Marrow Cells

Prior studies observed that different bone marrow cell preparations can express neural molecules after transplantation into brain. However, it has not been established whether the neural molecules are the consequence of transplantation or are already present in the bone marrow, as formerly shown for products of the MBP gene (Marty et al., 2002). The expression of neural markers in noncultured ex vivo bone marrow therefore was investigated (FIG. 1). The neurogenic transcription factor, Pax-6, and the four neuronal proteins that were examined, neurofilament H, NeuN, HuC/HuD, GAD65, were present in a small percentage of adult bone marrow cells. Double immunocytochemistry labeling demonstrated that Pax-6 and neurofilament H were present in the same cells. In addition, while the oligodendroglial protein, CNPase, also was discovered in some bone marrow cells, no labeling was detected with antibody to astroglial glial fibrillary acidic protein (GFAP).

In order to determine whether the bone marrow cells, which express neural antigens, represent haematopoietic stem cells, double immunocytochemistry was carried out with neural markers and CD34, a marker of bone marrow stem cells. Strong labeling with antibodies to neurofilament H, NeuN, GAD65, HuC/HuD, Pax-6 and CNPase was present in only a subset of ex vivo CD34+ cells (FIG. 1).

Example 3

Generation of Highly Proliferating Haematopoietic Progenitors

Figure 2:
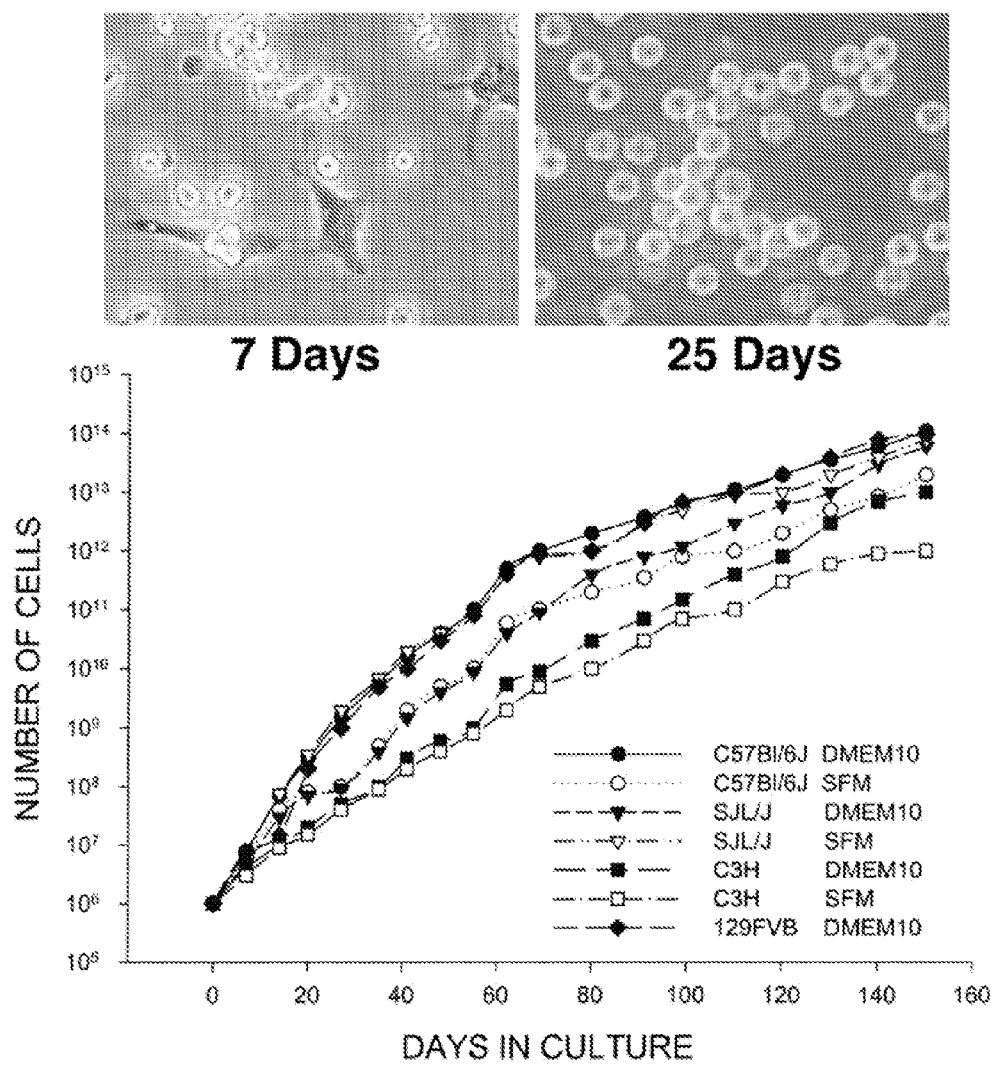
FIG. 2 demonstrates long-term cultures of CD34+, Sca-1+, AA4.1+, cKit+ cells from adult mouse bone marrow. Photomicrographs of bone marrow cells at 7 and 25 days. Growth curves of cells from adult bone marrow of C57B1/6J, C3H, SJL/J and 129FVB mice in serum-containing and serum-free medium.
Figure 4:
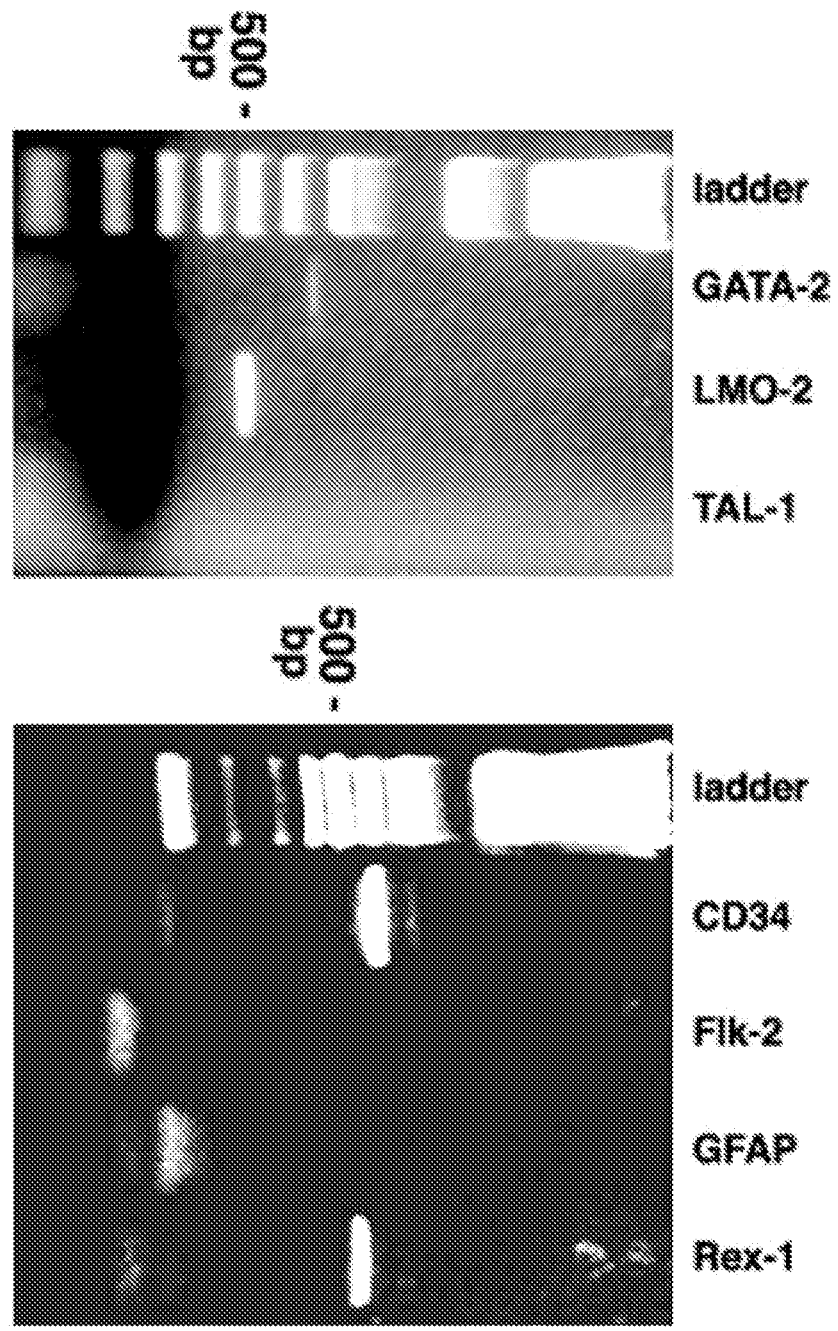
FIG. 4 shows detection of RT-PCR products of GATA-2, LMO-2, Rex-1, Flk-2, TAL-1, CD34 and GFAP mRNA from cells in 6 week cultures of adult C57B1/6J bone marrow.
Figure 5:
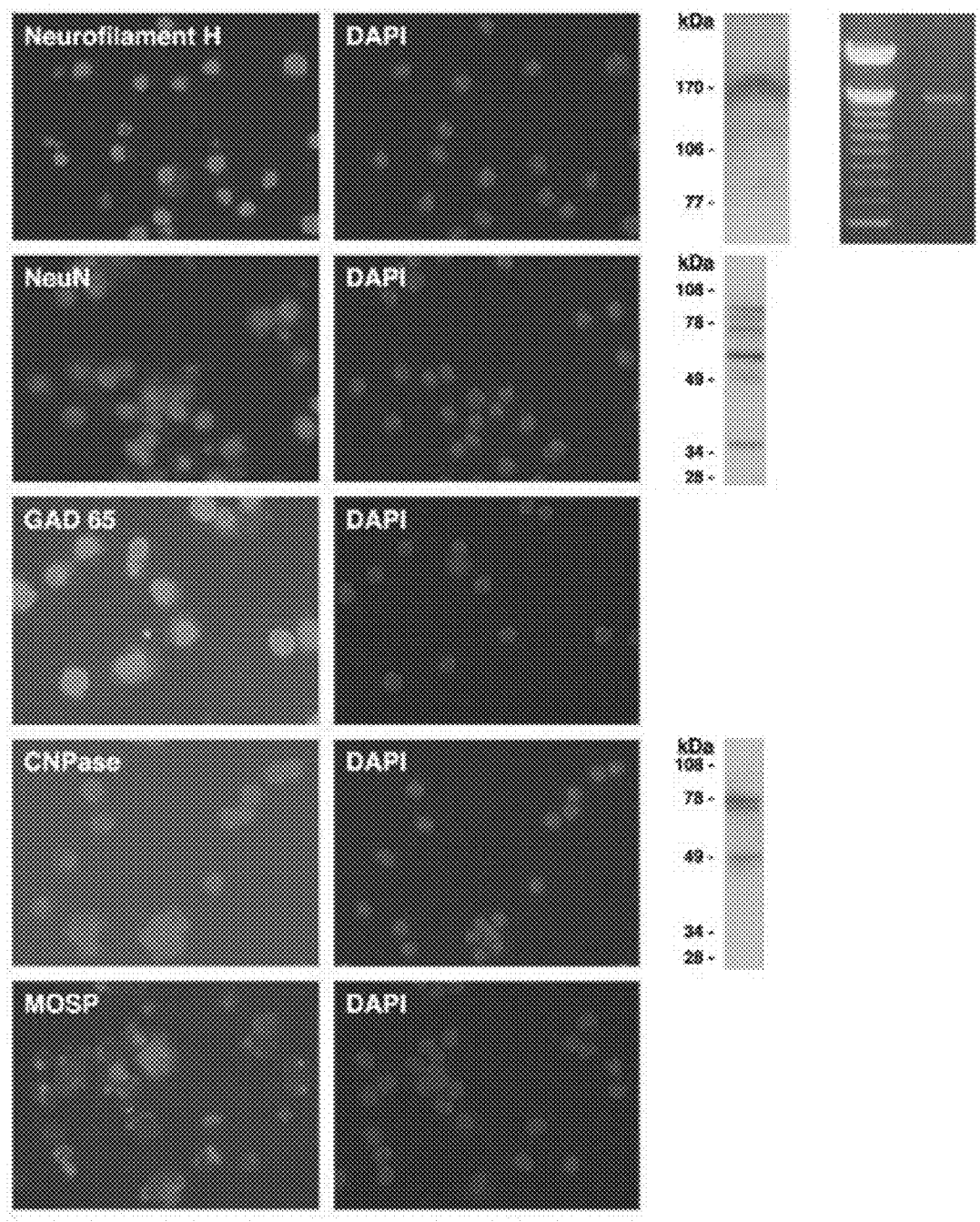
FIG. 5 demonstrates detection of neural gene expression in adult mouse bone marrow cells cultured for 6-10 weeks. Three neuronal genes were detected: Neurofilament H detected by immunocytochemistry, Western blot analysis and RT-PCR; NeuN detected by immunocytochemistry and Western blot; GAD65 detected by immunocytochemistry. Two oligodendroglial genes: CNPase detected by immunocytochemistry and Western blot and MOSP detected by immunocytochemistry.

Because neural antigens were present in a subset of bone marrow cells bearing CD34, an antigen which can be found on haematopoietic progenitors, a method was developed to generate cultures of highly proliferative CD34+ cells. Bone marrow of four strains of mice was harvested from 26 adult femurs and individually cultured in liquid medium containing the haematopoietic stem cell growth factors: interleukins IL3 and IL6, Stem Cell Factor and β-mercaptoethanol. Only non-adhering floating cells were continuously subcultured over four months as described above. With time in culture, the percentage of adherent cells decreased to zero by 3-4 weeks (FIG. 2). These floating cells, that grow over 30 generations, show a high proliferative capacity. Indeed, over a four-month period of culture, $10^{14}$ cells were generated from 106 bone marrow cells obtained from one mouse femur. A 3 µl pellet of bone marrow cells can be expanded into a 300 liter pellet of pure CD34+ cells as evidenced by PCR (FIG. 4B) and immunocytochemistry (FIG. 5). Similar proliferation rates were observed in all cultures whether in serum-containing or serum-free medium (FIG. 2).

The cells were assayed for haematopoietic markers at various time-points in culture. After 4-5 weeks all cells were highly CD34+ as well as CD45+, a general marker of all haematopoietic cells; in contrast, macrophage F4/80, endothelial cell Factor 8, erythroblast TER119, and B and T lymphocyte markers, CD19, CD4 and CD8, as well as B and T lymphocyte transcription factor TAL-1 were not detected (Table 1).

TABLE 1

Haematopoietic Markers in C57Bl/6J Mouse
Bone Marrow Cells cultured in IL-3, IL-6, SCF

| | Percent Positive Cells | | |
|---|---|---|---|
| Marker | 3 weeks | 4 weeks | 16 weeks |
| Haematopoietic Stem Cells | | | |
| CD34 | 95-99 | 100* | 100 |
| Sca-1 | 95-99 | 100 | 100 |
| AA4.1 | 95-99 | 100 | 100 |
| cKit | 95-99 | 100 | 100 |
| All Haematopoietic Cells | | | |
| CD45 | 100 | 100 | 100 |
| HMBP | 100 | 100 | 100 |
| Macrophages | | | |
| F4/80 | 1-3 | 0** | 0 |
| Endothelial Cells | | | |
| Factor 8 | 0 | 0 | ND |
| B Cells | | | |
| CD19 | 0 | 0 | ND |
| T - Cells | | | |
| CD 4 | 0 | 0 | ND |
| CD 8 | 0 | 0 | ND |

*All or ** none of the cells analyzed were positive

Figure 3:
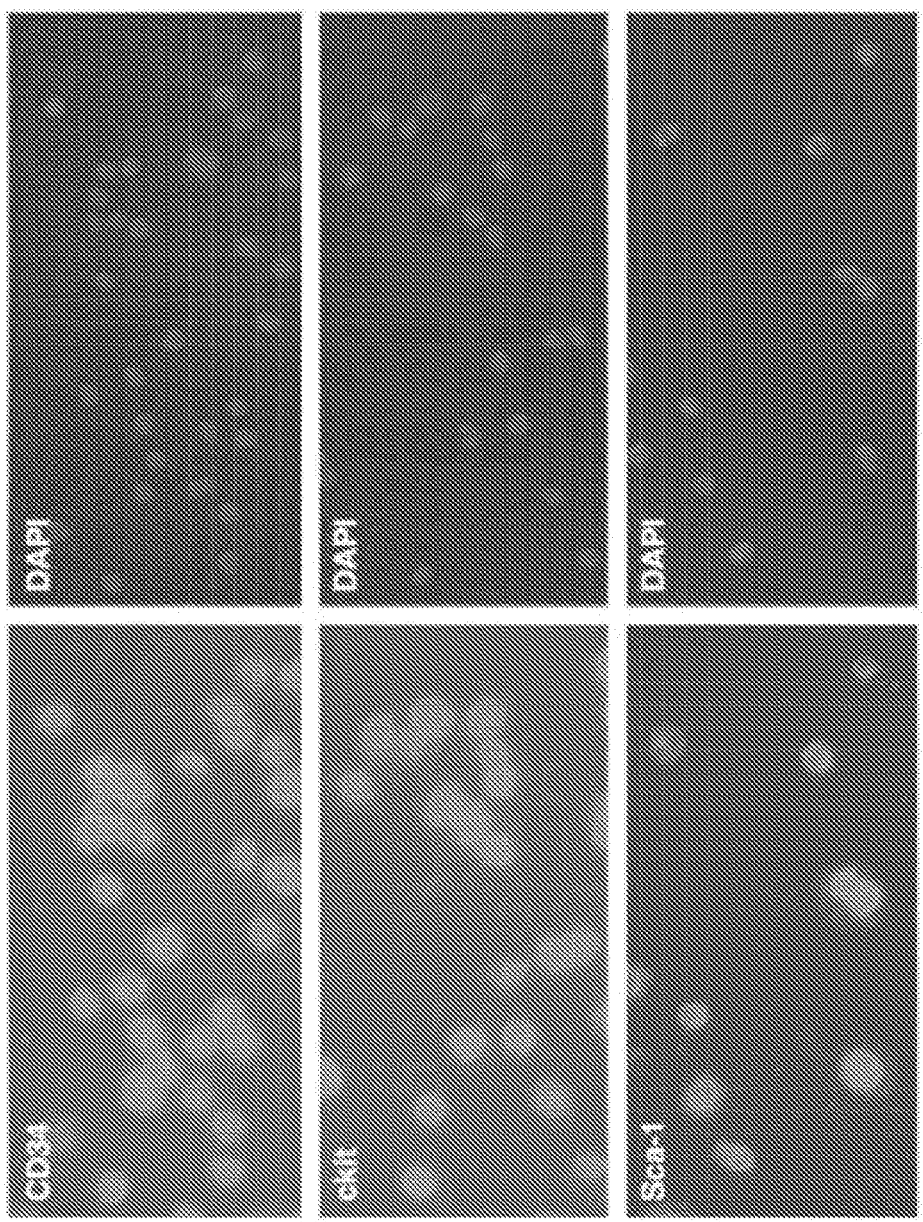
FIG. 3 shows immunocytochemical detection of CD34, cKit and Sca-1 on all cells in 6 week cultures of adult C57B1/6J bone marrow.

These results indicate that the CD34+ cells were not expressing haematopoietic differentiation markers and, therefore, suggested that they might correspond to stem cells. They then were analyzed for additional haematopoietic stem cell markers and found to be Sca 1+, AA4.1+ and cKit+ (Table 1 and FIG. 3). Thus, these cells had a cell surface phenotype which is comparable to that found in haematopoietic stem cells. Furthermore, they expressed transcriptional factors, GATA-2 and LMO-2, known to be present in haematopoietic progenitors (FIG. 4A).

Example 4

Neural Markers in Haematopoitic Progenitors Cultured from Bone Marrow

Neural genes were found to be expressed in a minor subset of CD34+ bone marrow cells. Therefore, their presence was examined in the highly proliferative cultures of haematopoietic progenitors at three weeks and at later times when all cells were CD34+. Both neural transcription factors and markers of differentiated neurons, astroglia and oligodendrocytes were investigated. When all cells were CD34+, all cells also were positive for the neurogenic transcription factor, Pax-6, and neuronal RNA-binding protein, HuC/HuD. Then the pure population of CD34+ cells was assessed for expression of general neuronal markers and neurotransmitters (FIG. 5). Cells probed for neurofilaments H, M and L by RT-PCR were found to express only neurofilament H but not M and L, whereas the same primers used to probe the CD34+ cells gave the expected products in postnatal d2 mouse brain (not shown). Immunocytochemistry also revealed that all cultured CD34+ cells expressed neurofilament H, but not neurofilament M and L. Additionally, Western blot analysis showed neurofilament H at 170 kDa but not bands for neurofilaments M and L. Immunocytochemistry and Western blot analyses of cultured CD34+ cells showed that NeuN was abundant in all cells and expressed at the expected molecular weights of 66, 48 and 46 kDa. Because general markers of neurons were present in the CD34+ cultures, markers of neuronal function were also investigated. Indeed, glutamic acid decarboxylase (GAD 65), the enzyme responsible for GABA synthesis, was detected in all cells examined, whereas tyrosine hydroxylase and M2 muscarinic acetylcholine receptor were not (Table 2).

TABLE 2

Neural Cell Markers on Cultured CD34+ Cells

| | Percent positive cells | | |
|---|---|---|---|
| | 0 day | 21 day | 56/110 day |
| Neural Transcription Factors | | | |
| Pax-6 | 1.5 | 92 | 100 |
| Oct-4 | 1.5 | 92 | 100 |
| Neurons | | | |
| HuC/HuD | 1.5 | 92 | 100 |
| Neurofilament H | 1.5 | 92 | 100*† |
| NeuN | 1.5 | 91 | 100* |
| Glutamic acid decarboxylase GAD 65 | 1.5 | ND | 100 |
| Tyrosine hydroxylase | ND | ND | 0 |
| M2 muscarinic acetylcholine receptor | ND | ND | 0 |
| Glial Astrocytes | | | |
| GFAP | 0 | 0 | 0*† |
| Oligodendrocytes | | | |
| CNPase | 1.5 | 92 | 100*† |
| MOSP | ND | ND | 100* |
| HMBP/MBP2 | 100 | ND | 100*† |
| Galactocerebroside | ND | ND | 100* |
| NG2 chondroitin sulfate proteoglycan | ND | ND | 100* |
| O4 | 0 | 0 | 0 |

*Western blot and †PCR analyses

The next step was to determine the presence of molecules considered to be markers of glial cells, i.e., astrocytes and oligodendrocytes. The intermediate filament of astrocytes, glial fibrillary acidic protein (GFAP), was not detected at the mRNA or protein level at any stage in the culture of CD34+ cells (FIG. 4B). In contrast, oligodendrocyte markers: CNPase, MOSP (FIG. 5), galactocerebroside and NG2 chondroitin sulfate proteoglycan were present (Table 2) while O4 was not detected (not shown). These data indicate that early transcription factors, as well as markers of differentiated cells of the nervous system, are present in the bone marrow derived CD34+ cell cultures.

Example 5

Early Embryonic Cell Markers CD34+ Cell Cultures

The most plausible origin of the CD34+ cell cultures that express neural genes is the amplification of a small percentage of CD34+ cells present in ex vivo bone marrow, which also express neural genes. It may be that these CD34+ cells derive from pluripotent bone marrow cells, somewhat similar to embryonic stem cells. Therefore, the cultured CD34+ cells were screened for markers of early general transcription factors, Rex-1 and Oct-4, by PCR and found to be positive (Rex-1, FIG. 4; Oct-4, not shown). Immunocytochemistry indicated that a small subset of ex vivo bone marrow cells were positive for Oct-4 (FIG. 1) as were one hundred percent of the cultured CD34+ cells (not shown). This suggests that, indeed, the cultured CD34+ cells may be stem cells with a greater potential than merely haematopoietic stem cells.

Example 6

Transplantation of Cultured CD34+ Cells into Brain

Figure 6:
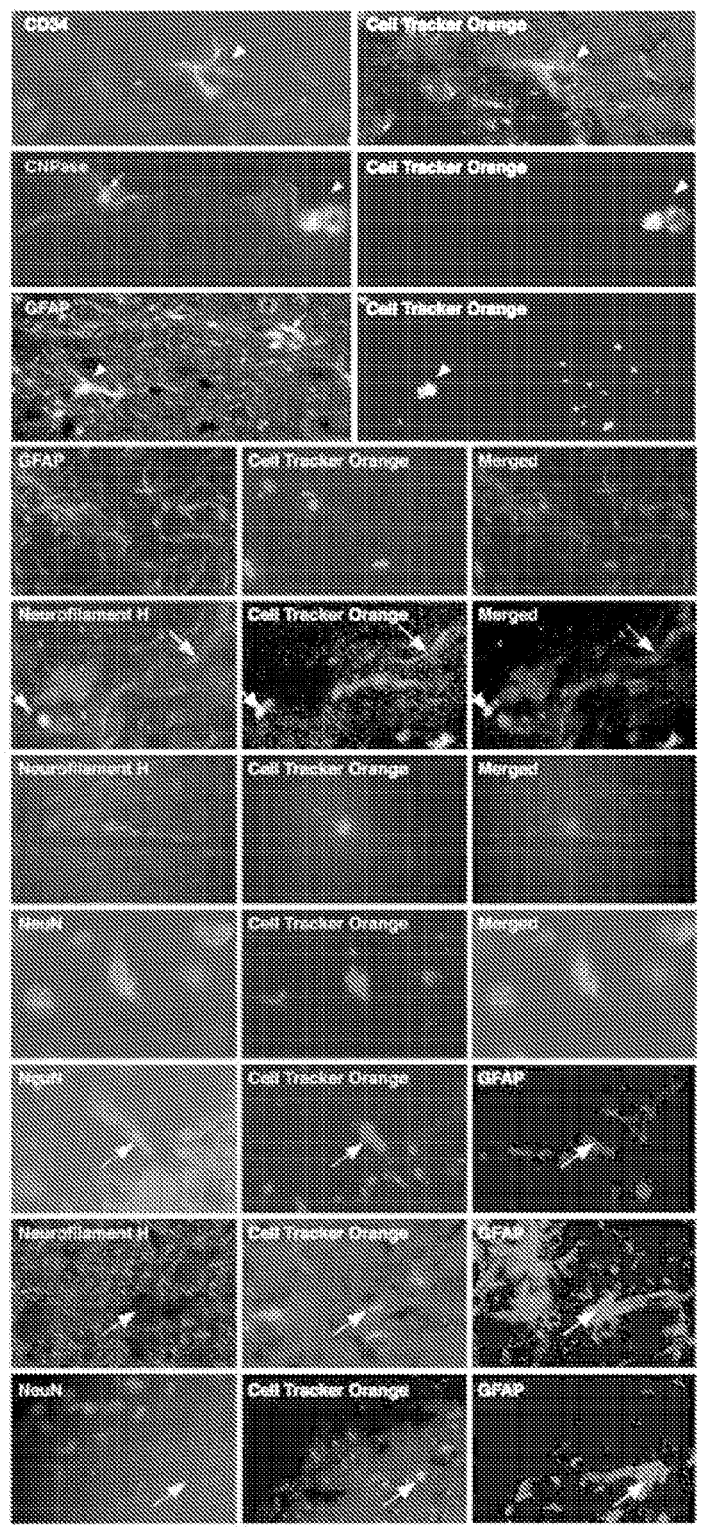
FIG. 6 shows immunohistochemical analysis by laser confocal microscopy of gene expression by Cell Tracker Orange (CTO)-labeled, cultured CD34+, Sca-1+, AA4.1+, cKit+ adult C57B1/6J mouse bone marrow cells transplanted into adult C57B1/6J mouse brain hippocampus and striatum. CD34 expressed in CTO-labeled cells 6 weeks after implantation into adult brain—host brain cells fail to express CD34. Oligodendroglial CNPase (transplanted cell, arrowhead; host cell, arrow), astroglial GFAP (transplanted cell, arrowhead; host cell, arrow), and neuronal neurofilament H and NeuN expression in CTO-labeled adult mouse bone marrow cells one year after implantation into adult mouse brain. Last three rows: analysis by double-labeling for NeuN and GFAP and for neurofilament H and GFAP in CTO-labeled adult CD34+ bone marrow cells in adult mouse brain one year after implantation.

Since these cells express molecules compatible with a neural phenotype, we thought it reasonable to transplant them into adult mouse brain without any further treatment. CD34+ cells, cultured for from 6 weeks to 3 months, were labeled with Cell Tracker Orange and injected stereotactically into brain striatum and hippocampus of thirty-four adult mice. From one month to fourteen months after transplantation, brains were processed for immunohistochemistry and fluorescence microscopy. The transplanted Cell Tracker Orange-labeled cells were found to survive in high numbers in both striatum and hippocampus (approximately 40% of injected cells) for 14 months, the longest time tested, without any obvious alteration in the behavior of the animals. This high percentage of survival of implanted cells in brain is in contrast to other laboratories that injected cells into circulating blood of sublethally or lethally irradiated mice and into the peritoneum of newborn PU.1 mice (Brazelton et al., 2000; Mezey et al., 2000; Makar et al., 2002). In addition, the CD34+ cells injected into the brain migrated from the injection site throughout the striatum and hippocampus and beyond. From 1 to 2 months after implantation, some remained spherical in shape, while others extended short processes and continued to express CD34 (FIG. 6, top row); at 6 months they exhibited morphologies reminiscent of neurons, astroglia and oligodendrocytes. The implanted brain sections were immunolabeled for markers of neurons: neurofilament H and NeuN, astroglia: GFAP and oligodendrocytes: CNPase. A striking finding was that while at the time of injection into brain, all CD34+ cells expressed neurofilament H, NeuN and CNPase, at six months and 1 year after transplantation, only 40% of implanted cells express neurofilament H and/or NeuN, and 30% express CNPase (FIG. 6 and Table 3).

TABLE 3

CD34+ Stem Cells Implanted in Adult Mouse
Brain Selectively Express Neural Markers

| Protein | Number of Positive Cells | Percentage positive |
|---|---|---|
| Neurofilament | 815 | 42 |
| NeuN | 795 | 42 |
| GFAP | 490 | 25 |
| CNPase | 580 | 30 |

In addition, whereas no CD34+ cells in culture expressed GFAP, after implantation into the brain 30% of them did express GFAP. Double labeling demonstrated that cells expressing neurofilament H or NeuN did not express CNPase or GFAP (FIG. 6). Similarly, GFAP was not detected in cells that expressed CNPase (not shown). Thus, neurofilament, NeuN and CNPase immunoactivity is lost in 60-70% of the implanted CD34+ cells, whereas, GFAP appeared in 30% of implanted CD34+ cells. Therefore, these data indicate that there are two stages of expression of neural markers in the CD34+ cells reported here. While all cells in the CD34+ cultures express neurofilament H, NeuN and CNPase in vitro, in sharp contrast, in transplanted cells, neuronal and oligodendrocyte markers segregated into distinct populations by suppressing either the neuronal gene expression or oligodendrocyte gene expression or both in cells that became GFAP+ after transplantation. These data indicate that GFAP, neurofilament and CNPase expression are regulated under the environmental control of the brain. The plasticity of these CD34+ cells in brain to become neurons or glia is reminiscent of earlier reports of the capacity of glial cells to become neurons in vivo (Laywell et al., 2000; Fischer et al., 2001; Fischer et al., 2002; Malatesta et al., 2003).

The demonstration that a minor population of ex vivo bone marrow cells expresses neural antigens as well as an haematopoietic stem cell marker leads to a new interpretation of data from other laboratories who reported expression of neural antigens in bone marrow cells transplanted into brain; indeed, they have suggested that it is the environment of the brain that leads to the transdifferentiation of bone marrow cells for the acquisition of neural antigens (Brazelton et al., 2000; Mezey et al., 2000). In contrast, it has been reported that selected bone marrow cells, which are CD34-negative, transplanted into brain, failed to express neural antigens (Castro et al., 2002). Since cells expressing neural antigens are only a minor population of the bone marrow, these diverging findings may be accounted for by the fact that different laboratories may be implanting distinct populations of bone marrow cells, which may or may not include the minor population expressing neural antigens.

Thus, an embodiment of this Example is that ex vivo bone marrow cells with a haematopoietic stem/progenitor cell phenotype do express molecules associated with the nervous system, indicating that adult haematopoietic stem cells, which classically are thought to be of mesodermal origin, express neural genes, which are regarded as restricted to cells derived from ectoderm. The presence of neural transcription factors and neural differentiation antigens in ex vivo CD34+ bone marrow cells indicates that these cells are permissive or predisposed to differentiate into neural cells when placed in the milieu of the brain.

This work has focused on the neural aspects of these CD34+ haematopoietic progenitor cells, yet in specific embodiments they are multipotent beyond the nervous system or indeed totipotent, as the presence of Rex-1 and Oct-4 indicates. Stem cells from bone marrow are the only known source of stem cells that circulate in the blood and have access to all tissues of the body, with the exception of the brain unless the blood-brain barrier is compromised. In an embodiment wherein these cells are multipotent, they provide a source for seeding stem cells in other tissues of the body.

Example 7

Sorting of Bone Marrow Stem Cells

Figure 7:
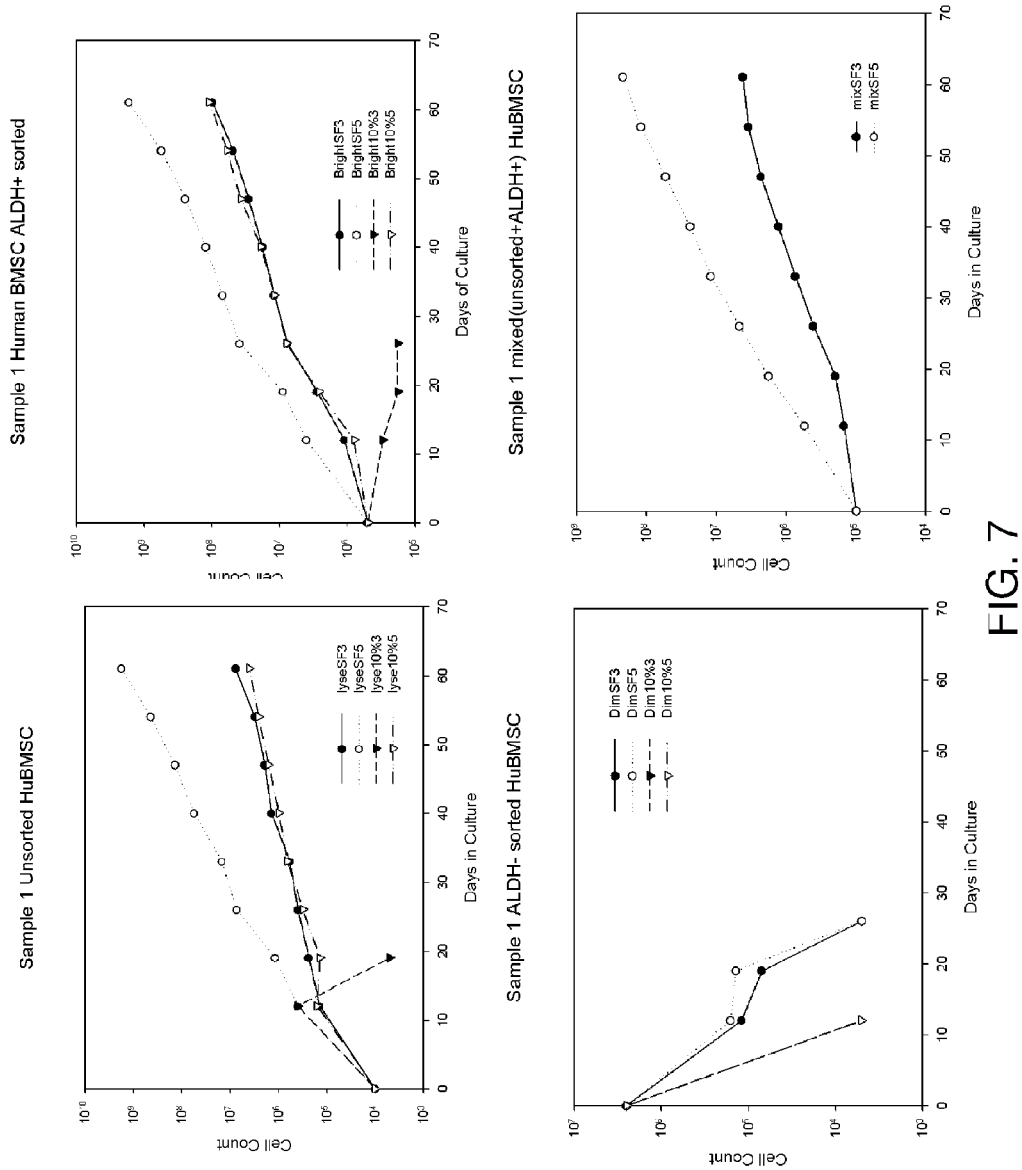
FIG. 7 illustrates growth curves for a sample comprising unsorted human bone marrow stem cells (HuBMCS). The cells were cultured under varying conditions. The following notation was utilized: aldehyde dehydrogenase (ALDH+); ALDH+ Bright-sorted bone marrow stem cells; ALDH-Dim-sorted non-stem cells; SF-serum-free; 3-refers to 3 exemplary growth factors being interleukin-3, interleukin-6, and stem cell factor; 5-refers to 5 exemplary growth factors being interleukin-3, interleukin-6, stem cell factor, flt3/fflk2, and TPO; 10%-10% fetal bovine serum-containing medium.
Figure 8:
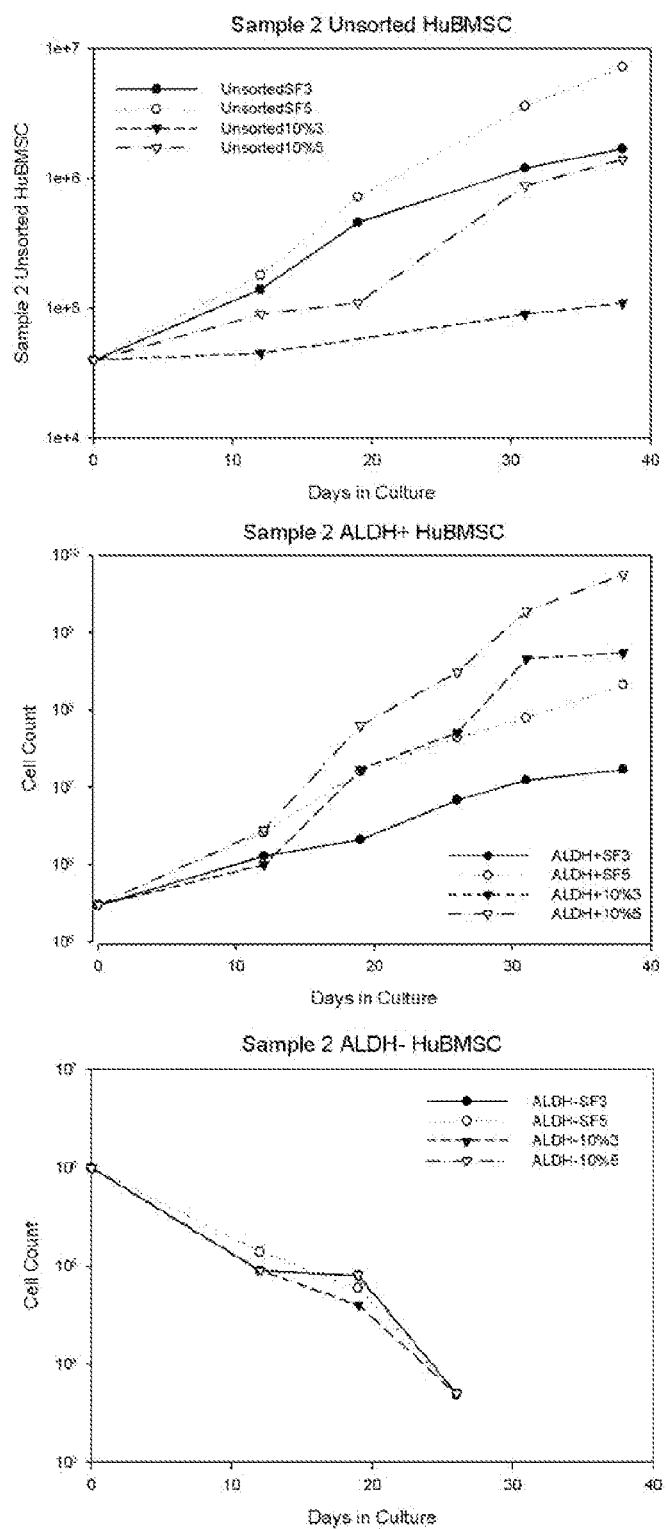
FIG. 8 illustrates growth curves for another sample comprising unsorted human bone marrow stem cells (HuBMCS). The cells were cultured under varying conditions. The following notation was utilized: aldehyde dehydrogenase (ALDH+); ALDH+ Bright-sorted bone marrow stem cells; ALDH-Dim-sorted non-stem cells; SF-serum-free; 3-interleukin-3; 5-interleukin-5; 10%-10% fetal bovine serum-containing medium.
Figure 9:
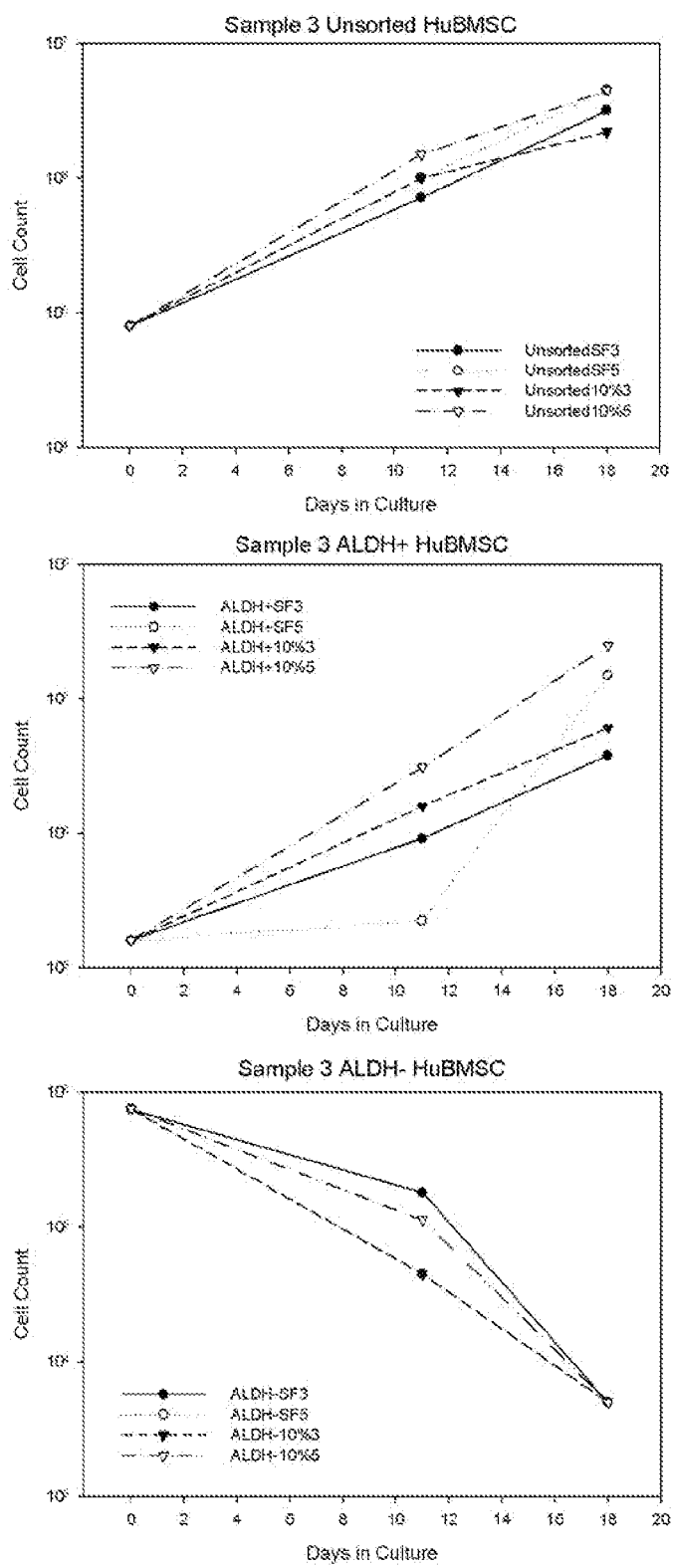
FIG. 9 illustrates growth curves for an additional sample comprising unsorted human bone marrow stem cells (HuBMCS). The cells were cultured under varying conditions. The following notation was utilized: aldehyde dehydrogenase (ALDH+); ALDH+ Bright-sorted bone marrow stem cells; ALDH-Dim-sorted non-stem cells; SF-serum-free; 3-interleukin-3; 5-interleukin-5; 10%-10% fetal bovine serum-containing medium.

Sorting of the exemplary bone marrow stem cells is described. For example, FIGS. 7, 8 and 9 illustrate sorting of the exemplary bone marrow stem cell in serum-free (SF) medium containing 3 (IL-3, IL-6, SCF) and 5 (IL-3, IL-6, SCF, flt3/fflk2, TPO) growth factors and medium containing ten percent fetal bovine serum plus the factors. Three samples were utilized. The cell fractions were as follows: unsorted adult human whole bone marrow; alcohol dehydrogenase (ALDH+) Bright sorted bone marrow "stem cell" fraction; ALDH-Dim refers to sorted "non-stem cell" fraction; and a mixture of unsorted plus ALDH+ Bright stem cells.
ALDH+ Bright Cell Fraction Stem cells were previously shown to express high levels of aldehyde dehydrogenase (ALDH). When bone marrow cells were exposed to this fluorescent substrate, those cells containing ALDH fluoresce brightly. Those with no or low levels of ALDH fluoresce dimly. Therefore, ALDH+ Bright fraction is enriched for hematopoietic stem cells; ALDH(−). Dim cells are the remaining bone marrow cells depleted of stem cells. The third fraction is unsorted whole bone marrow cells containing both stem cells and all other cells of bone marrow.

Cultures of both ALDH+ Bright sorted cells and unsorted grow and expand in number over time due to continued growth of stem cells in the cultures. ALDH(−) are dim cultures that are depleted of stem cells do not grow and expand, but eventually die.

In a particular embodiment, it was determined if stem cells in early cultures needed the support of non-stem cells present in bone marrow cultures to get started growing. Therefore, unsorted and ALDH+ Bright stem cells were mixed in different ratios and growth rates of the combinations of cells were measured. ALDH+ Bright cell cultures and unsorted whole bone marrow cell cultures, as well as combinations of the two fractions, grew at similar rates. Therefore, support by ALDH (−) Dim cells was not required for growth of stem cells from bone marrow, in some embodiments. However, sorting of stem cells from whole bone marrow, in order to start with enriched cultures of stem cells, offers no known advantage over growing stem cells from whole bone marrow.

Example 8

Mouse Bone Marrow Progenitor Cells

I. Cell Replacement Therapy and Gene Delivery in Mouse Neurodegeneration
A. Experimental Allergic Encephalomyelitis (EAE)

Figure 10:
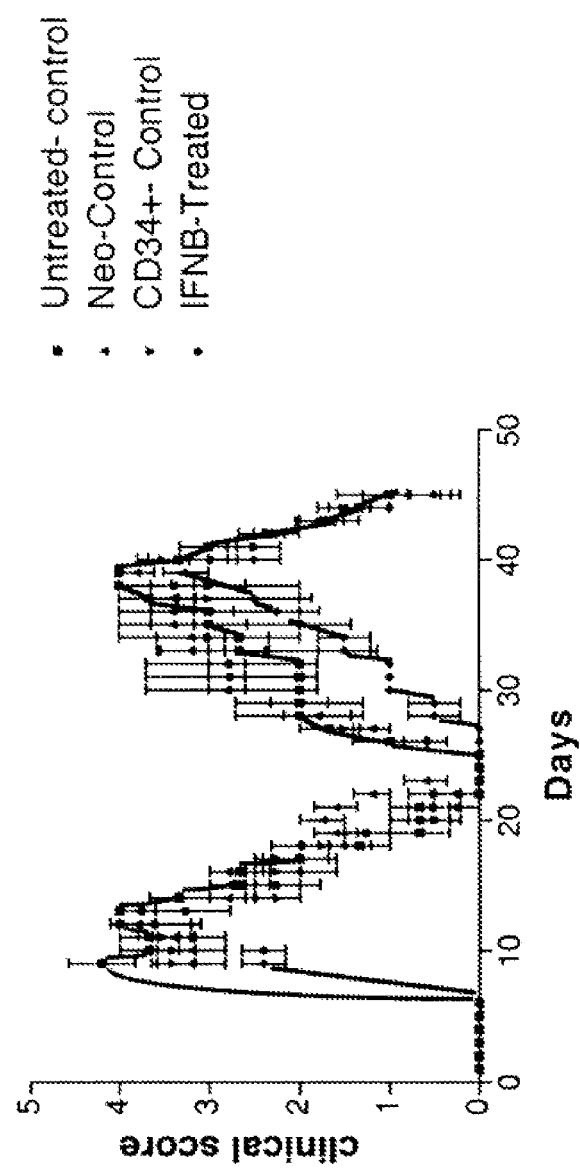
FIG. 10 demonstrates clinical effects of CD34+ cells engineered to express Interferon-β in EAE mice. The onset of the relapsing phase is delayed and the severity is reduced (diamonds). Each point is the mean of five animals in each group: CD34+/IFN-β and controls: CD34+/neo, CD34+ only and Untreated.
Figure 11:
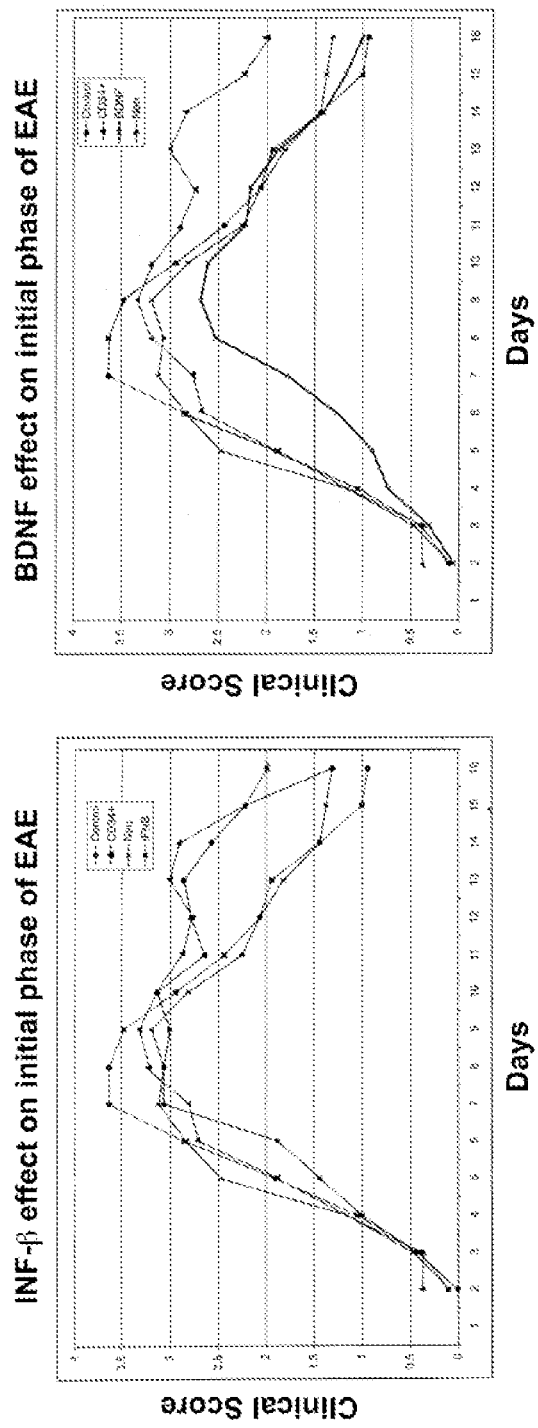
FIG. 11 shows clinical effects of CD34+ cells engineered to express Interferon-β or Brain Derived Neurotrophic Factor (BDNF) transplanted into Experimental Allergic Encephalomylitis (EAE) mice. The onset of the initial phase is delayed and the severity is reduced (diamonds) as measured by the art-recognized five-point scale of paralysis. Each point is the mean of twenty animals in each group: CD34+/IFN-β, CD34+/BDNF and controls: CD34+/neo, CD34+ only.

Interferon-β expressing CD34+ cells and Brain Derived Neurotrophic Factor (BDNF) expressing CD34+ cells ameliorate the relapsing phase of Experimental Allergic Encephalomyelitis. In a pilot study of twenty mice (five per group), CD34+ cells transfected with the mouse neuroprotective Interferon-beta (IFN-β) gene were transplanted into Experimental Allergic Encephalomylitis (EAE) mice. Mice transplanted with CD34+ cells expressing IFN-β show a delayed onset and reduced severity of the relapsing phase of EAE, as measured by the five-point scale of paralysis (FIG. 10). In specific embodiments, the neuroanatomical basis of this neuroprotection is demonstrated. However, at the least, these results indicate that CD34+ cells are useful vehicles for neuroprotective gene delivery to adult mouse brain.
B. Shiverer Mouse, a Myelin Basic Protein-Deficient Mutant Mouse In a larger 120 mouse experiment, with 20 mice per group, the protective effect is examined of CD34+ cells alone and CD34+ cells that express IFN-β and CD34+ cells that express BDNF on EAE symptoms. CD34+ cells alone as well as CD34+ cells expressing IFN-β or BDNF were protective at least in the initial phase of EAE (FIGS. 10 and 11). BDNF showed the most robust effect; IFN-β was second and CD34+ cells alone were the least effective. This protection by CD34+ cells alone in a specific embodiment is a beneficial paracrine effect of the cells because the time frame post-injection of the cells is too short for cell replacement and differentiation to be the protective cause.

Additionally, CD34+ cells were transplanted into Shiverer mouse brain, another model of MS. Specifically, normal adult C3H mouse bone marrow stem cells were injected into C3H Shiverer mouse brain, the genetic mutant mouse that does not express myelin basic protein. The mice virtually stopped shivering at six weeks after transplant (ten of ten mice). Video and still photos document the cessation in shivering. The mice have shivered progressively less over time since transplant. In some embodiments, brains are taken for immunohistochemistry and microscopy characterization. The studies on additional Shiverer mice are repeated and monitored on a daily basis to quantitate changes with time by counting shivers/min/mouse, for example. Although most Shiverers die between three and six months and the Shiverer mice are about 12 weeks old at the time of filing, the implanted mice appear healthy. The mice are maintained to see how long they survive and to see if they revert to shivering.

Figure 12:
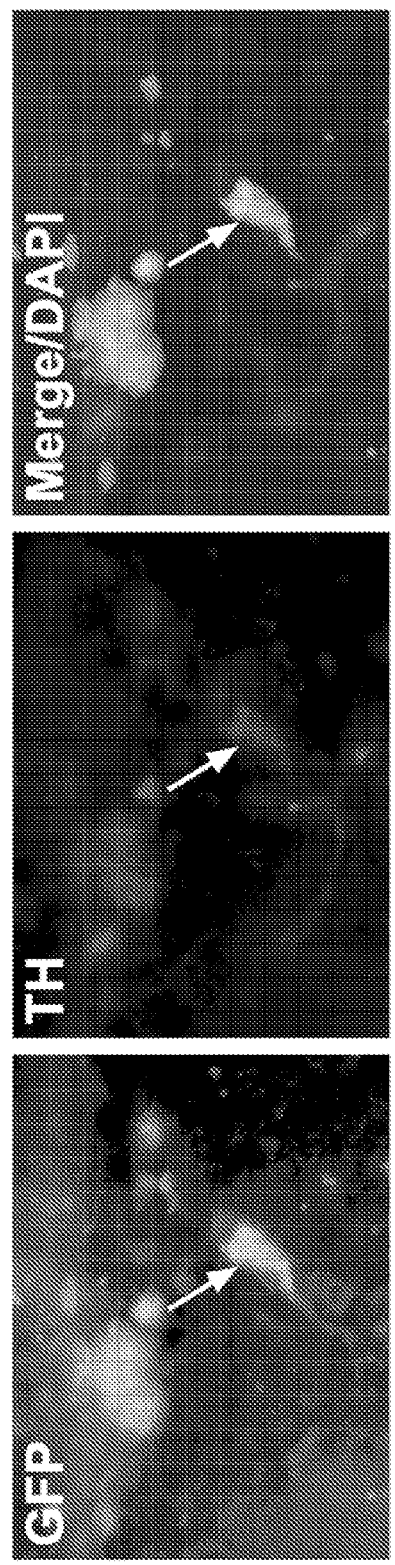
FIG. 12 demonstrates some CD34+ cells from a transgenic mouse that expresses Green Fluorescent Protein (GFP) in all cells, transplanted into normal adult mouse brain that express a neuronal morphology also express tyrosine hydroxylase (TH), detected by antibody to TH, 8 weeks (a 20 μm-thick section of mouse brain). The brain section was counterstained with DAPI that labels all cell nuclei.

II. Bone Marrow Cell Culture of Transgenic Green Fluorescent Protein (GFP) Mouse C. Transplanted GFP-CD34+ Cells Express Tyrosine Hydroxylase (TH) in Mouse Brain CD34+ cells were transplanted into normal adult mouse brain express tyrosine hydroxylase. CD34+ cells are cultured that express Green Fluorescent Protein (GFP) from the GFP-transgenic mouse, C57Bl/6-Tg(UBC-GFP)30Scha. These cells are used for transplantion into MPTP-treated C57Bl/6J mouse brain. They have been transplanted into normal C57Bl/6J brain and found that after eight weeks, for example, the implanted cells are extending processes. A subset of these implanted cells also express tyrosine hydroxylase (FIG. 12). After this finding, the cultured CD34+/GFP cells were assayed for TH expression in vitro with five antibodies to dopaminergic neurons: TH (Chemicon AB151 and AB152, Sigma T2928), TH transcription factor PITX3 (Chemicon AB5722) and dopamine β-hydroxylase (DiaSorin 22806) and found them to be negative before transplantation.

D. TH, PITX3 and Dopamine b-Hydroxylase are not Expressed by Cultured CD34+ Cells Because some CD34+/GFP cells, transplanted into normal adult mouse brain, were found to express a neuronal morphology and to express tyrosine hydroxylase, they and CD34+/GFP cells engineered to express BDNF are transplanted into MPTP-treated mouse brain. MPTP specifically destroys TH-expressing dopaminergic neurons of the substantia nigra that are lost in Parkinson's disease. The MPTP mouse model is used to evaluate the efficacy of stem cells from bone marrow for therapeutic cell replacement and neuroprotective gene therapy in neurodegeneration where a specific lesion site exists.

Example 9

Rat Bone Marrow Progenitor Cells

III. Rat Bone Marrow Stem Cell Culture
A. Growth Curve

Bone marrow stem cells from adult Sprague Dawley rat femurs were successfully using the culture methods developed for mouse bone marrow stem cell culture but by using rat IL-3, IL-6 and SCF. The rat cells grow logarithmically (FIG. 13) as do mouse and human bone marrow stem cells. The cultured bone marrow stem cells expressed embryonic stem cell, haematopoietic stem cell and neural stem cell as well as differentiated neural cell genes (Table 4).

B. CD34+ Cell Gene Expression

The gene expression in CD34+ cells is characterized at least in part to monitor the presence and/or differentiation of the cells. The expression of one or more particular genes is chosen based in the desired differentiation. The methods to identify gene expression includes those that monitor the nucleic acid products of gene expression (such as mRNAs) or the gene product produced (such as proteins). In specific embodiments, the gene expression is identified by any suitable means, although in particular embodiments immunocytochemistry is employed, including by immunofluorescence. Exemplary gene expression is provided in Table 4.

TABLE 4

Exemplary Gene Expression by Bone Marrow Stem Cells cultured from Adult Rat

| Gene Product | Percent Positive |
|---|---|
| Embryonic stem cell | |
| Oct 4 | 100 |
| Haematopoietic stem cell | |
| CD34 | 100 |
| Sca-1 | 100 |
| CD45 | 100 |
| Neural stem cell | |
| Pax-6 | 100 |
| Neuronal | |
| HuC/HuD | 100 |
| Neurofilament H | 100 |
| NeuN | 100 |
| M2 muscarinic acetylcholine receptor | 0 |
| Tyrosine hydroxylase | 0 |
| Astrocyte | |
| GFAP | 0 |
| Oligodendrocyte | |
| CNPase | 100 |
| MOSP | 100 |
| NG2 | 100 |
| Galactocerebroside | 100 |
| O4 | 0 |

Example 10

Human Bone Marrow Progenitor Cells

IV. Growth of ALDH+ Sorted Cells and Unsorted Cells

Figure 13:
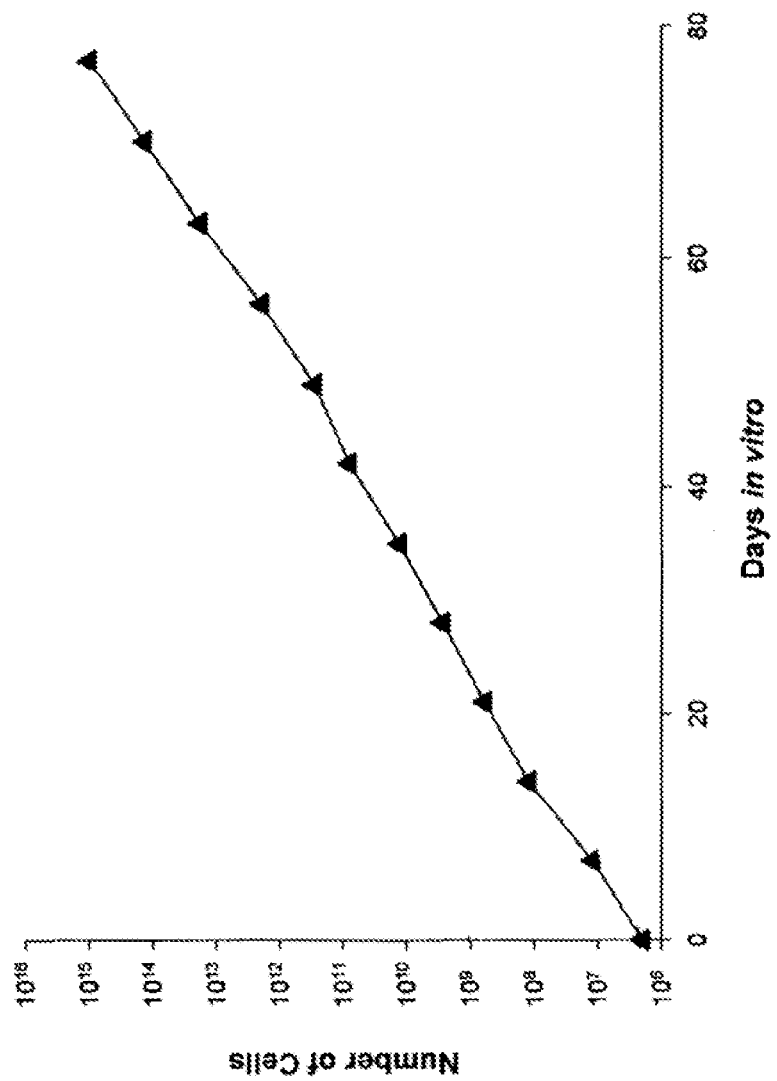
FIG. 13 shows adult rat bone marrow stem cell growth in $DMEM_{10}$ containing 10 ng/ml rat IL-3, 10 ng/ml rat IL-6, 10 ng/ml SCF and β-mercaptoethanol ($10^{15}$ cells were grown from $10^6$ cells in 80 days).

Adult Human ex vivo bone marrow expresses Haematopoietic stem cell, Embryonic stem cell, Neural stem cell and differentiated neural genes. Ex vivo adult human bone marrow was examined and found that four percent of bone marrow cells express CD34, a marker of haematopoietic stem cells (FIG. 13 and Table 5). Double labeling revealed that a subset of these CD34+ stem cells also express embryonic stem cell genes, neural stem cell genes as well as genes of differentiated neurons, astroglia and oligodendroglia. This gene expression is similar to that found in adult mouse bone marrow with the exception that GFAP was not detected in mouse bone marrow.

TABLE 5

Gene expression by adult human ex vivo bone marrow cells

| MARKER | POSITIVE CELLS/ TOTAL CELLS | PERCENTAGE |
|---|---|---|
| Haematopoietic Stem Cell Markers | | |
| CD34 | 31/747 | 4 |
| CD45 | 289/324 | 90 |
| Embryonic Stem Cell Marker | | |
| Oct-4 | 13/562 | 2 |
| Neural Stem Cell Marker | | |
| Pax-6 | 9/281 | 3 |

TABLE 5-continued

Gene expression by adult human ex vivo bone marrow cells

| MARKER | POSITIVE CELLS/ TOTAL CELLS | PERCENTAGE |
|---|---|---|
| Neuronal Markers | | |
| HuC/HuD | 25/923 | 3 |
| Neurofilament H | 10/609 | 2 |
| NeuN | 6/197 | 3 |
| M2 acetylcholine receptor | 11/514 | 2 |
| Astrocyte Marker | | |
| GFAP | 11/407 | 2 |
| Oligodendrocyte Markers | | |
| CNPase | 17/800 | 2 |
| MOSP | 8/414 | 2 |
| O4 | 10/441 | 2 |
| MAG | 6/305 | 2 |
| NG2 | 12/373 | 3 |

Four percent of nucleated cells of bone marrow express the haematopoietic stem cell marker, CD34. Double labeling showed that a subset of these CD34+ cells expresses embryonic and neural stem cell genes and differentiated neural genes.

Figure 14:
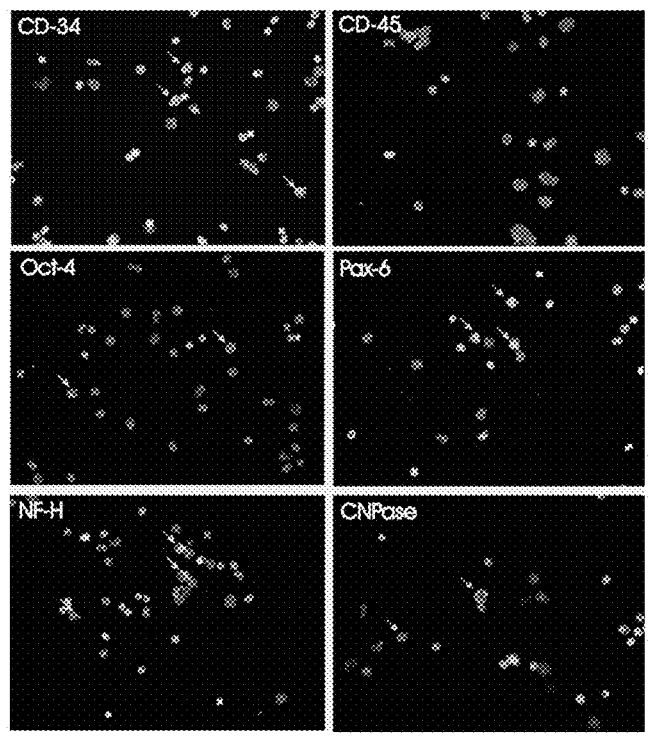
FIG. 14 demonstrates immunocytochemical analysis of gene expression in adult human ex vivo bone marrow. A subpopulation of cells expresses haematopoietic, embryonic and neural stem cell genes as well as differentiated neuronal and oligodendrocyte genes. Arrows indicate cells immunopositive for haematopoietic stem cell CD34 and CD45; embryonic stem cell Oct-4; neural stem cell Pax-6; neuronal neurofilament H; oligodendrocyte CNPase. DAPI marks all cell nuclei in the field.
Figure 15:
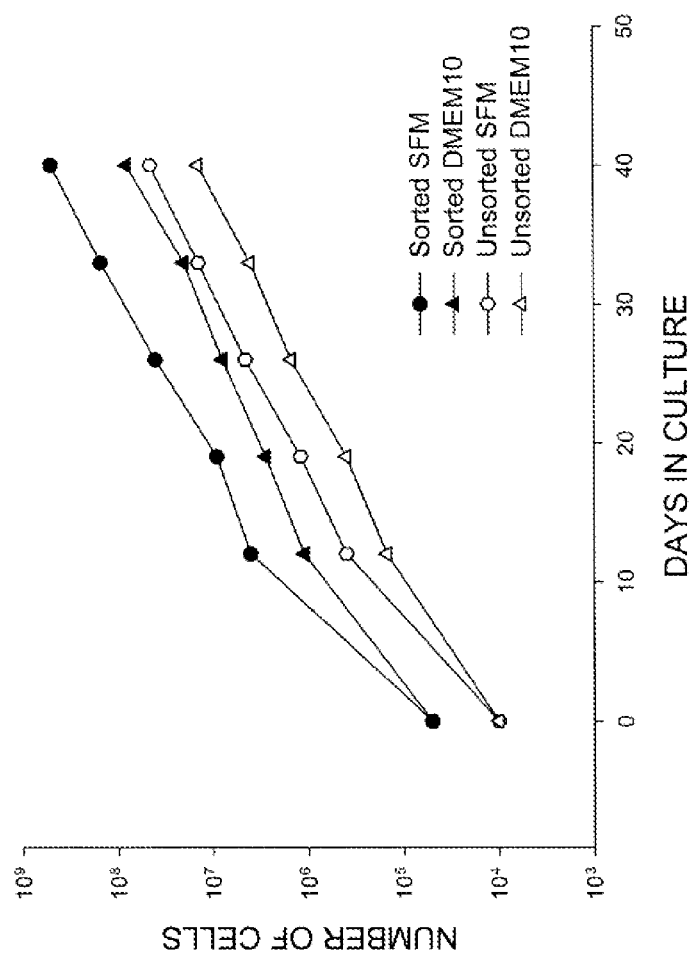
FIG. 15 shows that adult human bone marrow stem cells grow logarithmically in serum-free (SFM) and serum-containing ($DMEM_{10}$) media. Both flow cytometry-sorted ALDH+ stem cells and stem cells from unsorted whole bone marrow grow somewhat better in SFM than in DMEM with 10% fetal bovine serum.

Adult Human bone marrow cells grow in culture by the methods developed to grow mouse bone marrow cells. Bone marrow stem cells were grown from two normal adult humans using serum-free and serum-containing media supplemented with human Interleukin-3, Interleukin-6 and Stem Cell Factor (FIGS. 14 and 15). Unsorted, whole bone marrow and flow cytometry-sorted aldehyde dehydrogenase-positive stem cells grew at similar rates, but in both cases grew somewhat better in serum-free medium than in serum-containing medium. The stem cell population expanded three to four orders of magnitude over forty days in culture.

V. Growth of Cells in Culture Medium With Two Sets of Growth Factors

Human bone marrow cells were cultured in four media: serum-free medium (SFM) containing human IL-3, IL-6 and SCF and SFM containing IL-3, IL-6, SCF, Flt3/Flk2 and Thrombopoietin (Tpo) and in serum-containing medium with the two sets of growth factors. Additionally, human cells were cultured in various combinations of cells: 1) ALDH+ Bright sorted cells only, 2) ALDH Dim sorted cells only, 3) unsorted cells only, and 4) ALDH+ Bright cells co-cultured with unsorted cells. The ALDH+ Bright cells were co-cultured with unsorted cells from the first human sample to test whether the unsorted cells were necessary to condition the growth medium to allow the ALDH+ Bright cells to survive and grow. It was determined that this is not necessary, given that the ALDH+ Bright cells grow well by themselves.

Example 11

Retinal Engineering: Engrafted Neural Cells Establish Proper Circuitry

In one embodiment of this aspect of the invention, it is advantageous to determine the parameters by which postmitotic embryonic neural retina cells and embryonic retinal stem cells, transplanted into adult eyes, are able to 1) implant in the retina; 2) migrate to the correct retinal stratum location; 3) differentiate into the proper neuronal and glial morphologies; and 4) establish proper functional circuits, for example. Given that the present inventors have found that embryonic chick retinal cells are able to implant in adult mouse retina, in this study embryonic mouse retinal cells are transplanted into normal C57B1/6J adult mouse eyes into one mouse strain with retinal deficits: retinitis pigmentosa model mouse, C57B1/6J-Peb rd1 le. This work is important for therapeutic cell replacement in retinopathies in which specific classes of neural cells are lost, for example: photoreceptors are lost in age-related macular degeneration, retinitis pigmentosa, Leber's congenital amaurosis, rod monochromomacy and X-linked progressive cone dystrophy; ganglion cells are lost in multiple sclerosis and methanol toxicity; M class ganglion cells are lost in glaucoma, Alzheimer's disease and hydrocephalus; and Muller cells are lost in adult retinoschisis. Additionally, the retina, a part of the CNS, may be used as a model for cell transplantation and therapeutic cell replacement in the brain for the treatment of neuropathies in Parkinson's disease and Alzheimer's disease, for example.

In another aspect of this embodiment of the invention, it is determined if cultured adult mouse CD34+ bone marrow stem cells can implant in adult mouse brain and differentiate into neural cells for therapeutic neural cell replacement. Bone marrow stem cells are implanted in normal adult mouse brain and in two mouse models of neurodegeneration. Cultured CD34+ cells are stereotactically injected into the hippocampus and striatum of normal adult mouse brain and into those regions of MPTP-treated Parkinsonian model adult mouse brains.

In an additional aspect of this embodiment of the invention, CD34+ cells are injected into the hippocampus and cerebellum of the exemplary dysmyelination Shiverer mouse brain model of multiple sclerosis. Implantation and differentiation of bone marrow cells are compared between normal mouse brain and the two models of neurodegeneration: Shiverer and MPTP-treated.

In another aspect of this embodiment of the invention, it is determined if adult human stem cells cultured from bone marrow have the capacity to differentiate into neural cells when transplanted into Nude mouse brain.

Retinal Stem Cell Transplantation into Adult Mouse Eyes

In order to determine if neural cells are able to implant in the CNS and migrate to form proper circuits for cell replacement after neuropathy, adult CNS tissue in the intact animal is required to simulate human patient therapy, in one embodiment. Cell penetration, cell migration, cell integration and cell differentiation in organotypic cultures do not completely reiterate these processes in retina in the intact eye. Therefore, mice are used because more than fifteen strains of mice have retinal dystrophies that are the models for retinitis pigmentosa and retinal degeneration. In this study, embryonic mouse retinal cells are transplanted into normal C57B1/6J adult mouse eyes and into retinitis pigmentosa model C57BL/6J-Pebrd1 le mouse eyes In exemplary methods, about eighty mice are used. Twenty pregnant C57BL/6J females provide one hundred E16 embryos. Two hundred retinas from these embryos provide $10^8$ healthy cells for transplantation into 120 recipient eyes at $8\times10^5$ cells per eye. Three sets of recipient mice are used: Twenty C57BL/6J mice with normal retinas, twenty C57BL/6J-Pebrd1le retinitis pigmentosa model mice receive retinal stem cells and twenty receive hematopoietic stem cells. In order to determine the time-course of cell implantation and differentiation, each set of mice are divided into four groups of five each and the mice of each group is taken for microscopic analysis of the retinal cell implants one week, two weeks, three weeks and six weeks, respectively, after transplantation.

Exemplary Flow Chart of the Time-Course:

Week 1: Inject embryonic retinal cells into 10 eyes of 5 C57BL/6J mice. After one week sacrifice the mice, remove the eyes and prepare the retinas for microscopy.

Week 2: Inject embryonic retinal cells into 10 eyes of 5 C57BL/6J mice. After two weeks sacrifice the mice, remove the eyes and prepare the retinas for microscopy.

Week 3: Inject embryonic retinal cells into 10 eyes of 5 C57BL/6J mice. After three weeks sacrifice the mice, remove the eyes and prepare the retinas for microscopy.

Week 4: Inject embryonic retinal cells into 10 eyes of 5 C57BL/6J mice. After six weeks sacrifice the mice, remove the eyes and prepare the retinas for microscopy.

Week 10: Inject embryonic retinal cells into 10 eyes of 5 C57BL/6J-Peb$^{rd1}$ le mice. After one week sacrifice the mice, remove the eyes and prepare the retinas for microscopy.

Week 11: Inject embryonic retinal cells into 10 eyes of 5 C57BL/6J-Peb$^{rd1}$ le mice. After two weeks sacrifice the mice, remove the eyes and prepare the retinas for microscopy.

Week 12: Inject embryonic retinal cells into 10 eyes of 5 C57BL/6J-Peb$^{rd1}$ le mice. After three weeks sacrifice the mice, remove the eyes and prepare the retinas for microscopy.

Week 13: Inject embryonic retinal cells into 10 eyes of 5 C57BL/6J-Peb$^{rd1}$ le mice. After six weeks sacrifice the mice, remove the eyes and prepare the retinas for microscopy.

Week 20: Inject hematopoietic stem cells into 10 eyes of 5 C57BL/6J-Peb$^{rd1}$ le mice. After one week sacrifice the mice, remove the eyes and prepare the retinas for microscopy.

Week 21: Inject hematopoietic stem cells into 10 eyes of 5 C57BL/6J-Peb$^{rd1}$ le mice. After two weeks sacrifice the mice, remove the eyes and prepare the retinas for microscopy.

Week 22: Inject hematopoietic stem cells into 10 eyes of 5 C57BL/6J-Peb$^{rd1}$ le mice. After three weeks sacrifice the mice, remove the eyes and prepare the retinas for microscopy.

Week 23: Inject hematopoietic stem cells into 10 eyes of 5 C57BL/6J-Peb$^{rd1}$ le mice. After six weeks sacrifice the mice, remove the eyes and prepare the retinas for microscopy.

Pregnant C57BL/6J mice with E16 embryos are euthanized with $CO_2$ from a compressed $CO_2$ chamber and death is verified by cervical dislocation. Embryonic eyes are removed, the retinas dissected and retinal cells for transplantation are harvested by enzymatic dissociation. The retinal cells are labeled by Cell Tracker Orange, a fluorescent vital cytoplasmic dye that remains contained in the labeled cells for more than two months. The labeled embryonic retinal cells then are transplanted into recipient retinas of adult mice by intraocular injection. In each set of injections both eyes of 5 mice are injected. The adult mice are anesthetized with Avertin. A fresh working solution of 2.5% Avertin is made every two weeks. A dose of 0.017 ml/g or 0.34 ml/20 g mouse will be injected intraperitoneally. After five minutes, $8 \times 10^5$ labeled retinal cells in 10 ul PBS will be injected by single injection into each eye with a 30 Ga needle. After intraocular injection, the mice will receive, subcutaneously, the analgesic, buprenorphine at 0.1 ng/g body weight every 12 hours for 48 hours. At the end of each implantation period; 1, 2, 3 and 6 weeks, the mice are sacrificed with $CO_2$ in a closed chamber, their eyes removed and the retinas processed for fluorescence microscopy.

Example 12

Adult CD34+ Bone Marrow Cell Transplantation into Adult Mammalian Brain

I. Normal Mouse and MPTP-Treated Mouse Model of Parkinson's Disease

In order to determine if adult haematopoietic stem cells are able to implant in the brain, migrate and differentiate into neurons, glia and oligodendrocytes to form proper circuits for cell replacement after neuropathy, adult CNS tissue in the intact animal is required to simulate human patient therapy. Cell penetration, cell migration, cell integration and cell differentiation in organotypic cultures do not completely reiterate these processes in the intact brain. Mice are used because more than several strains of mice are models of neurodegenerative diseases. In this study, adult mouse bone marrow stem cells are transplanted into normal C57B1/6J and MPTP-treated C57B1/6J adult mouse hippocampus and striatum. Differences in cell implantation and the ratio of differentiation into neurons, glia and oligodendrocytes is compared in hippocampus and striatum in normal drain and in MPTP-treated brain. In MPTP-treated brain, differences between these ratios in the MPTP affected nigra/striatum and the unaffected hippocampus is determined. C57B1/6J mice are used because they are the strain most susceptible to MPTP.

In specific embodiments, about forty mice are used. Twenty normal adult female C57BL/6J mice are injected stereotactically into hippocampus and striatum with CD34+ bone marrow stem cells. Twenty adult female C57BL/6J mice are used as MPTP models of Parkinson's disease. In order to determine the time-course of cell implantation and differentiation, and the longevity of these cells in brain, each set of mice are divided into four groups of five each and the mice of each group are taken for microscopic analysis of the bone marrow stem cell implants six weeks, three months, six months and one year, respectively, after transplantation. Forty mice will allow an "n" of 5 for significant differences between groups in a Student's T test.

Flow Chart of Time Course:

Week 1 minus 12 days: Five daily injections of 20 adult C57B1/6J mice with MPTP as above.

Week 1: Inject 20 normal and 20 MPTP-treated adult C57B1/6J mice with CD34+ bone marrow cells as above.

Week 6: Sacrifice 5 normal and 5 MPTP-treated mice and prepare brains for immunohistochemistry.

Week 12: Sacrifice 5 normal and 5 MPTP-treated mice and prepare brains for immunohistochemistry.

Week 26: Sacrifice 5 normal and 5 MPTP-treated mice and prepare brains for immunohistochemistry.

Week 52: Sacrifice 5 normal and 5 MPTP-treated mice and prepare brains for immunohistochemistry.

Twenty normal adult female C57BL/6J mice are injected stereotactically into hippocampus and striatum with CD34+ cells. Twenty adult female C57BL/6J mice are used as MPTP models of Parkinson's disease for transplantation of neural stem cells and haematopoietic stem cells for therapeutic cell replacement pilot studies. MPTP (1-methyl-4-phenyl-1,2,3,6-tetrahydropyridine) (Research Biochemicals, Natick, Mass.) will be administered in 0.1 ml of PBS at a dose of 30 mg/kg intraperitoneally at 24-hr intervals for five doses. Seven days after the last MPTP injection C57B1/6J mouse CD34+ haematopoietic stem cells from in vitro culture will be injected stereotactically into the striatum and hippocampus, and the mice are maintained 6, 12, 26 and 52 weeks after stem injection and processed as previously stated in this protocol.

Effects of MPTP on Mouse Behavior

"The C57B1/6 mouse strain is the most sensitive and most common MPTP rodent model used . . . . The behavioral effects of MPTP lesioning in mice are less marked than those seen in nonhuman primates" (Tolwani, et al., 1999, Lab. Animal Sci. 49: 363-371). No effect of MPTP was found on eating and drinking. And "Not at any time did the body weight differ significantly" (Sundström, et al., 1990, Brain Res. 528: 181-188) between MPTP treated mice and vehicle treated mice. MPTP-treated "mice may develop initial short-term toxic effects, including hypersalivation, piloerection, and seizures. Mice usually recover quickly and manifest normal spontaneous behavior within 24 hr. Some short-term behavioral deficits, including hypokinesia and decreased activity have been reported" (Tolwani, et al., 1999, Lab. Animal Sci. 49: 363-371). "A decrease in locomotor activity and impairment of limb movements scored by pole and traction tests are clearly seem after MPTP withdrawal." (Arai, et al., Brain Res. 515: 57-63).

Mouse Monitoring

During MPTP treatment, mice are monitored daily for eating and drinking behavior and after treatment they are monitored biweekly for weight change. Food pellets are placed on the floor of the cage during MPTP treatment. If it appears that the mice are becoming dehydrated through decreased drinking, the mice are given fluids intravenously or subcutaneously. During the first day of MPTP treatment, the mice are monitored carefully by the veterinarian and animal care staff to check the severity of convulsions, if any, of the mice.

MPTP Handling

MPTP is weighed using gloves and mask by the investigator and MPTP is dissolved in Dulbecco's phosphate buffered saline in a chemical fume hood. MPTP is injected ip. into the mice with a 25 Ga needle.

Stem Cell Source for Implant

Primary C57B1/6J mouse (Charles River) bone marrow cells from the femur are cultured in vitro in defined serum-free medium by continuous passage of suspension cells for 4 to 8 weeks to generate a pure population of CD34+ haematopoietic stem cells for injection. Sterilely cultured cells ($10^4$) are injected into adult C57B1/6J mice (Charles River) in 1 µl Dulbecco's phosphate buffered saline into the striatum and $10^4$ cells/1 µl are injected into the hippocampus of the same hemisphere as the striatal injection. The cells have not been passaged through mice.

Stereotactic Injection of Stem Cells

Adult mice undergo stereotactic injection of stem cells into the brain striatum and hippocampus. For anesthesia of the mice, isoflurane is administered by inhalation of isoflurane in air from 100% isoflurane in a Labconco Fume Adsorber scavenger hood. The mouse then is injected intraperitoneally with 0.1 ml/20 gm mouse weight of 50 mg/ml pentobarbital (Nebutal Sodium Solution) diluted 1:1 in sterile distilled water. The mouse head is scrubbed with betadine followed by a 70% ethanol wash before surgery. Then, the skin over the skull is soaked in 70% ethanol and an incision of the skin is cut over the lateral skull. Two 2 mm holes are drilled in the skull over the striatum and the hippocampus with a hand-held hobbyist drill sterilized drill bit. Cells then are injected as described below with a 30 Ga needle held by a David Kopf stereotactic devise. The needle is removed, and after the two injections, the skin is sutured with thread. Lidocane (4% lidocane cream) is applied topically at the suture site once after suturing and the mice are monitored for discomfort and reapplication every 12 hrs for 48 hrs. The mouse is returned to its cage to recover. A heat lamp is not used during recovery from anesthesia because the mice wake up rapidly from isoflurane treatment. All surgery is performed under aseptic conditions (USPHS guidelines). Infection rate is <1% in previous studies.

II. Shiverer Mouse Model of Multiple Sclerosis

Thirty normal one month old female C3H mice and 30 one month old female C3H Shiverer mice are utilized for the study. In earlier work the inventors found that cultured CD34+ bone marrow stem cells differentiate morphologically into oligodendrocytes and express oligodendrocyte molecular markers when implanted into normal adult mouse brain. In an embodiment of the present invention, a dysmyelination model mouse, Shiverer, is used as a model for therapeutic cell replacement in multiple sclerosis.

In order to determine if adult haematopoietic stem cells are able to implant in the brain, migrate and differentiate into neurons, glia and oligodendrocytes that produce myelin and form myelin sheaths around CNS axons, CNS tissue in the intact animal is required to simulate cell replacement after dysmyelination in human patient therapy. Cell penetration, cell migration, cell integration and cell differentiation in organotypic cultures do not completely reiterate these processes in the intact brain. Mice are used because more than several strains of mice are models of neurodegenerative diseases including models of multiple sclerosis: Shiverer, Jimpy, Quakey, Twitcher and mld. In this study, adult mouse bone marrow stem cells are transplanted into normal C3H and C3H Shiverer mouse hippocampus and cerebellum. Differences in cell implantation and the ratio of differentiation into neurons, glia and oligodendrocytes are compared in hippocampus and cerebellum in normal brain and in Shiverer brain. In Shiverer brain, differences between these ratios in the hippocampus and cerebellum.

In specific embodiments, about forty-five mice are used. Fifteen one month old adult female C3H mice and thirty C3H Shiverer mice will be injected stereotactically into hippocampus and cerebellum with CD34+ bone marrow stem cells. In order to determine the time-course of cell implantation and differentiation, and the longevity of these cells in brain, each set of mice are divided into three groups of five each and the mice of each group are taken for microscopic analysis of the bone marrow stem cell implants one month, three months, six months, respectively, after transplantation. Because the life-expectancy of Shiverer mice is short young mice are implanted and additional mice are injected so there is a better chance to have 5 surviving mice at the three and six month time points. Forty mice allows an "n" of 5 for significant differences between groups in a Student's T test.

Flow Chart of Time Course

Week 1: Inject 15 normal C3H mice and 30 Shiverer mice with CD34+ bone marrow cells.

Week 4: Process 5 normal and 5 Shiverer mice for immunohistochemistry.

Week 12: Process 5 normal and 10 Shiverer mice for immunohistochemistry.

Week 26: Process 5 normal and 15 Shiverer mice for immunohistochemistry.

Exemplary General Methods

Bone Marrow Cell Collection

Bone marrow cells are collected sterilely from adult mice by first sacrificing the mouse by asphyxiation in $CO_2$ from a compressed $CO_2$ cylinder and death is assured by cervical dislocation. The mouse then is soaked in 70% ethanol. Skin is removed from the thigh with sterile forceps and scissors. Then muscle is removed from the femur with a second set of sterile instruments. Finally, the ends of the femur are removed with a third set of sterile instruments and marrow is extruded by injecting sterile DPBS from a 20 Ga needle into one end of the femur.

Adult Mouse Bone Marrow Culture

Pure CD34+ haematopoietic stem cell cultures are grown in serum-free and serum containing media in conditions as described herein. Briefly, bone marrow cells from adult femur are grown in continuous culture in the presence of IL-3, IL-6, SCF and β-mercaptoethanol at 37° C. in 10% $CO_2$. CD34+ cells will be cultured from C3H mouse bone marrow.

CD34+ Cell Labeling

CD34+ cells are labeled by fluorescent dye 5-(and 6)-(((4-chloromethyl)benzoyl)amino)tetramethylrhodamine (Cell Tracker Orange CMTMR) (Molecular Probes) as follows. CD34+ cells ($2 \times 10^8$) are incubated in a final concentration of 25 μM Cell Tracker Orange in DMEM10 from a 400× stock of 10 mM dye in dimethylsulfoxide (DMSO). Cells are incubated in 5 ml dye containing $DMEM_{10}$ at 37° C. for 15 min, pelleted by centrifugation, washed in 15 ml $DMEM_{10}$, incubated 30 min. at 37° C., pelleted, washed again in 15 ml $DMEM_{10}$ and resuspended in 0.5 ml $DMEM^{10}$. The labeled cells are suspended at $10^4$/μl of serum-free medium for stereotactic injection into adult mouse brain.

Stereotactic Injection of Dye Labeled CD34+ Cells into Brain

One month old C3H Shiverer mice are stereotactically injected into the cerebrum and cerebellum with $1 \times 10^4$ labeled C3H CD34+ stem cells/μl PBS. Injected mice are allowed to develop one, two and three months before the animals are sacrificed, the brains removed and prepared for immunohistochemistry and fluorescence confocal microscopy.

Antibody Characterization of Implanted Stem-Cells

Glial marker: glial fibrillary acidic protein (GFAP) (Chemicon, Sigma); oligodendrocyte marker: 2'3'-cyclic nucleotide 3'-phosphohydrolase (CNPase) (Chemicon); neuronal markers: neurofilament (Chemicon, Steinberger Monoclonal), neural cell adhesion molecule (NCAM) (Chemicon) and NeuN (Chemicon). Fluorescein labeled secondary antibodies (Kirkegaard & Perry) are used to detect binding of the primary antibody to brain sections and secondary antibody alone was used as a control. Immunohistochemistry was analyzed by laser confocal microscopy and photographed.

Preparation of Implanted Brains for Fluorescence Laser Confocal Microscopy

Injected brains are removed from the mouse after asphyxiation by $CO_2$. Then they are suspended in 4% paraformaldehyde in DPBS at 4° C. for 24 hr. Subsequently, the fixative is decanted from the brains and exchanged in DPBS at 4° C. for 24 hr. They then are equilibrated in 30% sucrose at 4° C. for 24 hr. Equilibrated brains are frozen and mounted on a cryostat specimen platform with cryo-embedding compound oriented to cut cross-sections of the brains. Serial cross-sections 30 μm thick are cut at −39° C. with a Microm cryostat. Brain sections are taken up on microscope slides and dried. Brain sections are treated with antibodies for immunohistochemistry by standard methods and then stained with 25 ng/ml 4',-diamidino-2-phenylindole (DAPI) cell nuclear dye, covered with microscope slide coverglass and sealed with fingernail polish. Implanted CD34+ cells are observed and photographed by fluorescence laser confocal microscopy with rhodamine, fluorescein and DAPI optics. Implanted CD34+ cells are scored for cell morphology and antibody detection of neural antigens and photographed.

Exemplary Specific Methods

Stem Cell Source for Implant

Primary C3H mouse (Charles River) bone marrow cells from the femur are cultured in vitro in defined serum-free medium by continuous passage of suspension cells for 4 to 8 weeks to generate a pure population of CD34+ haematopoietic stem cells for injection. Sterilely cultured cells ($10^4$) are injected into one month old C3H normal and Shiverer mice (Charles River) in 1 μl Dulbecco's phosphate buffered saline into the cerebellum and $10^4$ cells/1 μl are injected into the hippocampus of the same hemisphere as the cerebellar injection. The cells have not been passaged through mice. Because the life expectancy for Shiverer mice is short, thirty mice are injected and processed in three groups: the survivors of 5 at one month post-injection; the survivors of 10 at 3 months; and the survivors of 15 at 6 months.

Stereotactic Injection of Stem Cells

One month old mice undergo stereotactic injection of stem cells into the brain cerebellum and hippocampus. For anesthesia of the mice, isoflurane is administered by inhalation of isoflurane in air from 100% isoflurane in a Labconco Fume Adsorber scavenger hood. The mouse then is injected intraperitoneally with 0.1 ml/20 gm mouse weight of 50 mg/ml pentobarbital (Nebutal Sodium Solution) diluted 1:1 in sterile distilled water. The mouse head is scrubbed with betadine followed by a 70% ethanol wash before surgery. Then the skin over the skull is soaked in 70% ethanol and an incision of the skin is cut over the lateral skull. Two 2 mm holes are drilled in the skull over the striatum and the hippocampus with a hand-held hobbyist drill sterilized drill bit. Cells then are injected as described below with a 30 Ga needle held by a David Kopf stereotactic devise. The needle is removed, and after the two injections, the skin is sutured with thread. Lidocane (4% lidocane cream) are applied topically at the suture site once after suturing and the mice are monitored for discomfort and reapplication every 12 hrs for 48 hrs. The mouse is returned to its cage to recover. A heat lamp is not used during recovery from anesthesia because the mice will wake-up rapidly from isoflurane treatment.

Preparation of Animals for Immunohistochemistry

Animals are processed and brains are prepared as above for immunohistochemistry and fluorescence microscopy.

III. Transplantation of Human Bone Marrow Cells in Nude Mouse Brain

A nude mouse model was utilized for adult human bone marrow stem cell transplantation into brain employing methods of the present invention. In particular embodiments, an abundant number of homogeneous stem cells is generated from adult human bone marrow. As described elsewhere herein, stem cells grown from adult mouse bone marrow express the markers and morphologies of neurons, astroglia and oligodendroglia when transplanted into adult mouse brain. The human cells are characterized for their ability to generate neural cells when transplanted into adult Nude mouse brain. Based on the invention, an application includes growing stem cells from the bone marrow of an individual for therapeutic cell replacement for the neurodegenerative disorder of the patient, e.g., Parkinson's Disease, Multiple Sclerosis, Alzheimer's Disease, Huntington's Disease, ALS, etc.

Although one specific method is described for use of the model herein, a skilled artisan recognizes that particular parameters may be routinely optimized and still encompass the present invention. In specific embodiments, about thirty two month old female Nude mice are employed in the study. Given that the inventors demonstrated that cultured CD34+ mouse bone marrow stem cells differentiate morphologically into neurons, astrocytes and oligodendrocytes and express appropriate molecular markers when implanted into normal adult mouse brain, the human bone marrow stem cells in Nude mouse brain are analogously utilized as a model for stem cell differentiation into neural cells and therapeutic cell replacement.

The model is utilized in order to determine that adult human haematopoietic stem cells are able to implant in the brain, migrate and differentiate into neurons, glia and oligodendrocytes that produce myelin and form myelin sheaths around CNS axons. Cell penetration, cell migration, cell integration and cell differentiation in organotypic cultures do not completely reiterate these processes in the intact brain. Nude mice are used to avoid immune rejection of implanted human cells. In particular, adult human bone marrow stem cells are transplanted into Nude mouse neurogenic region of brain, the hippocampus and a non-neurogenic region of brain, the striatum, as has been done with mouse bone marrow stem cells. Differences in cell implantation and the ratio of differentiation into neurons, glia and oligodendrocytes are compared in hippocampus and striatum in normal brain.

In particular, thirty two month old adult female Nude mice are injected stereotactically into hippocampus and striatum with CD34+ bone marrow stem cells. In order to determine the time-course of cell implantation and differentiation, and the longevity of these cells in brain, the mice are divided into three groups of ten each and the mice of each group are taken for microscopic analysis of the bone marrow stem cell implants one month, three months, and six months, respectively, after transplantation. Thirty mice will allow an "n" of 10 for significant differences between groups in a Student's T test. The following exemplary protocol illustrates determination of the capacity of human bone marrow stem cells to differentiate into neural cells and the influence of site of implant on cell differentiation.

Flow Chart

| Experiment 1 (Mice (n = 30)) | | |
| --- | --- | --- |
| Experimental 1 (n = 10) | Experimental 2 (n – 10) | Experimental 3 (n = 10) |
| Inject human BMSCs | Inject human BMSCs | Inject human BMSCs |
| Monitor for 1 month | Monitor for 3 months | Monitor for 6 months |
| Euthanize and harvest brains | Euthanize and harvest brains | Euthanize and harvest brain |
| Histological studies | Histological studies | Histological studies |

Flow Chart of Time Course:
Week 0: Inject 30 Nude mice with human CD34+ bone marrow cells.
Week 4: Process 10 mice for brain immunohistochemistry.
Week 12: Process 10 mice for brain immunohistochemistry.
Week 24: Process 10 mice for brain immunohistochemistry.

General Exemplary Methods
Human Bone Marrow Cell Collection
Normal human bone marrow is obtained, such as commercially from StemCo Biomedical. In alternative methods, the bone marrow is not obtained commercially but is collected by conventional methods, such as from the patient.

Adult Human Bone Marrow Culture
Pure CD34+ haematopoietic stem cell cultures are grown in serum-free and serum containing media in conditions as described herein. Briefly, bone marrow cells are grown in continuous culture in the presence of human IL-3, IL-6, SCF and β-mercaptoethanol at 37° C. in 10% $CO_2$.

CD34+ Cell Labeling.
CD34+ cells are labeled by fluorescent dye 5-(and 6)-(((4-chloromethyl)benzoyl)amino)tetramethylrhodamine (Cell Tracker Orange CMTMR) (Molecular Probes) as follows. CD34+ cells ($2\times10^8$) are incubated in a final concentration of 25 μM Cell Tracker Orange in $DMEM_{10}$ from a 400× stock of 10 mM dye in dimethylsulfoxide (DMSO). Cells are incubated in 5 ml dye containing $DMEM_{10}$ at 37° C. for 15 min., pelleted by centrifugation, washed in 15 ml $DMEM_{10}$, incubated 30 min at 37° C., pelleted, washed again in 15 ml $DMEM_{10}$ and resuspended in 0.5 ml $DMEM_{10}$. The labeled cells are suspended at $10^4/\mu l$ of serum-free medium for stereotactic injection into adult mouse brain.

Stereotactic Injection of Dye Labeled CD34+ Cells Into Brain
Two month old Nude mice are stereotactically injected into the hippocampus and striatum with $1\times10^6$ labeled C3H CD34+ stem cells/μl PBS. Injected mice are allowed to develop one, two and three months before the animals are sacrificed, the brains removed and prepared for immunohistochemistry and fluorescence confocal microscopy.

Antibody Characterization of Implanted Stem-Cells
Glial marker: glial fibrillary acidic protein (GFAP) (Chemicon, Sigma); oligodendrocyte marker: 2'3'-cyclic nucleotide 3'-phosphohydrolase (CNPase) (Chemicon); neuronal markers: neurofilament (Chemicon, Steinberger Monoclonal), neural cell adhesion molecule (NCAM) (Chemicon) and NeuN (Chemicon). Fluorescein labeled secondary antibodies (Kirkegaard & Perry) are used to detect binding of the primary antibody to brain sections and secondary antibody alone was used as a control. Immunohistochemistry was analyzed by laser confocal microscopy and photographed.

Preparation of Implanted Brains for Fluorescence Laser Confocal Microscopy
Injected brains are removed from the mouse after asphyxiation by $CO_2$. Then they are suspended in 4% paraformaldehyde in DPBS at 4° C. for 24 hr. Subsequently, the fixative is decanted from the brains and exchanged in DPBS at 4° C. for 24 hr. They then are equilibrated in 30% sucrose at 4° C. for 24 hr. Equilibrated brains are frozen and mounted on a cryostat specimen platform with cryo-embedding compound oriented to cut cross-sections of the brains. Serial cross-sections 30 μm thick are cut at −39° C. with a Microm cryostat. Brain sections are taken up on microscope slides and dried. Brain sections are treated with antibodies for immunohistochemistry by standard methods and then stained with 25 ng/ml 4',-diamidino-2-phenylindole (DAPI) cell nuclear dye, covered with microscope slide coverglass and sealed with fingernail polish. Implanted CD34+ cells are observed and photographed by fluorescence laser confocal microscopy with rhodamine, fluorescein and DAPI optics. Implanted CD34+ cells are scored for cell morphology and antibody detection of neural antigens and photographed.

Specific Exemplary Methods
Stem Cell Source for Implant
Human adult bone marrow, obtained from StemCo Biomedical, are cultured in vitro in defined serum-free medium by continuous passage of suspension cells for about 4 to 8 weeks to generate a pure population of CD34+ haematopoietic stem cells for injection. Sterilely cultured cells ($10^6$) are injected into two month old Nude mice (Jackson) in 1 μl Dulbecco's phosphate buffered saline into the hippocampus and $10^6$ cells/1 μl are injected into the striatum of the same hemisphere as the hippocampal injection. The cells have not been passaged through mice. Because the life expectancy for Nude mice is short, thirty mice are injected and they are processed in three groups: the survivors of 10 at one month post-injection; the survivors of 10 at 3 months; and the survivors of 10 at 6 months.

Stereotactic Injection of Stem Cells
One month old mice undergo stereotactic injection of stem cells into the brain hippocampus and striatum. For anesthesia, the mice are injected intraperitoneally with 0.1 ml/20 gm mouse weight of 50 mg/ml pentobarbital (Nebutal Sodium Solution) diluted 1:1 in sterile distilled water. The mouse head is scrubbed with betadine followed by a 70% ethanol wash before surgery. Then, the skin over the skull is soaked in 70% ethanol, and an incision of the skin is cut over the lateral skull. Two 2 mm holes are drilled in the skull over the hippocampus and the striatum with a hand-held hobbyist drill sterilized drill bit. Cells then are injected as described below with a 30 Ga needle held by a David Kopf stereotactic devise. The needle is removed, and after the two injections, the skin is sutured with thread. Lidocane (4% lidocane cream) is applied topically at the suture site once after suturing and the mice are monitored for discomfort and reapplication every 12 hrs for 48 hrs. If the lidocane does not control the pain, other painkiller, such as Buprenorphine at 0.01-0.03 mg/kg BW, may be administered. The mouse is returned to its cage to recover. A heat lamp is not used during recovery from anesthesia because the mice wake-up rapidly from the treatment. All surgery is performed under aseptic conditions (USPHS guidelines), and the infection rate is <1% in previous studies. Mice are monitored daily post-operatively for behavior changes and if problems of movement, drinking or eating are observed the mouse is prepared for Immunohistochemistry. Preparation of Animals for Immunohistochemistry Animals are processed and brains are prepared as above for immunohistochemistry and fluorescence microscopy.

Example 13

Exemplary Cell Markers and Cell Characteristics of Some Stem Cells of the Invention Table 6 below regards flow cytometry-sorted ALDH+ bright cells from adult human bone marrow that were grown in serum-free medium containing IL-3, IL-6 and SCF (3 Factors) of IL-3, IL-6, Flk-2 and Tpo (5 Factors). The cultured cells were assayed by immunocytochemistry for markers of haematopoietic stem cells and neural stem cells after 18, 25 and 66 days in culture. The population of stem cells were found to be homogeneous at each time-point for CD34, CD45, cKit and Pax-6 expression.

TABLE 6

Human ALDHbr BMSCs

| Marker | Intensity | Positive/Total Cells | Percent |
|---|---|---|---|
| Cultured 18 Days | | | |
| Serum-free/3 Factors | | | |
| CD34 | (−) | 500/505 | 100 |
| CD45 | (−/lo) | 499/500 | 100 |
| cKit | (+) | 389/395 | 100 |
| Pax-6 | (+/lo) | 311/500 | 100 |
| Cultured 25 Days | | | |
| Serum-free/3 Factors | | | |
| CD34 | (−) | 498/500 | 100 |
| CD45 | (−/lo) | 495/508 | 100 |
| cKit | (+) | 399/409 | 100 |
| Pax-6 | (+/lo) | 310/320 | 100 |
| Serum-free/5 Factors | | | |
| CD34 | (−) | 350/350 | 100 |
| CD45 | (−/lo) | 345/350 | 100 |
| cKit | (+) | 489/500 | 100 |

TABLE 6-continued

Human ALDHbr BMSCs

| Marker | Intensity | Positive/Total Cells | Percent |
|---|---|---|---|
| Cultured 66 Days | | | |
| Serum-free/3 Factors | | | |
| CD34 | (−) | 490/505 | 100 |
| CD45 | (−/lo) | 494/500 | 100 |
| Pax-6 | (+/lo) | 497/500 | 100 |
| Serum-free/5 Factors | | | |
| CD34 | (−) | 350/355 | 100 |
| CD45 | (−/lo) | 345/350 | 100 |
| Pax-6 | (+/lo) | 489/500 | 100 |

In Table 7, adult human whole bone marrow cells were removed, fixed and CD34+ cells in the bone marrow were assayed for mitosis (Ki67) and apoptosis (Caspase3 and TUNEL) by immunocytochemistry. CD34+ cells were found to be 93% mitotic and 5% apoptotic in bone marrow.

TABLE 7

| Normal Human ex vivo CD34+ Stem Cells | |
|---|---|
| Ki67+ | 93.4 ± 1.15 |
| Ki67− | 6.56 ± 0.77 |
| Caspase3+ | 5.66 ± 0.58 |
| Caspase3− | 94.33 ± 1.98 |
| TUNEL+ | 5.4 ± 0.47 |
| TUNEL− | 94.5 ± 1.75 |

Example 14

Apoptosis in Hematopoietic Stem Cells in a Mature Model of Down Syndrome

Human trisomy 21 is essentially characterized by severe abnormalities in the nervous system. In addition, deficiencies of hematopoietic cells are very frequent in these patients and their risk of developing hematological and immune disorders is drastically increased. Mouse models of human trisomy 21 have been produced with mouse chromosome 16, which is most homologous to human chromosome 21. Indeed, in trisomic 16 mouse increased apoptosis has been reported in progenitor cells in the nervous system and thymus during fetal development. Herein, bone marrow stem/progenitor CD34+ cells from adult segmental trisomic mouse, Ts65Dn, have a dramatic reduction in proliferative capacity as compared to their diploid littermates. Indeed the vast majority of trisomic CD34+ stem/progenitor cells ex vivo are apoptotic. In addition, the in vitro proliferative capacity of Ts65Dn CD34+ cells was drastically reduced. This is the result of a reduced mitotic rate and a high proportion of apoptotic cells. Nevertheless, the phenotypic traits that were examined are comparable in trisomic and diploid cells. These results from nervous system, thymus, and hematopoietic system indicate that a common mechanism is at work in stem/progenitor cells in trisomic mice affecting cell proliferation and survival.

Human trisomy 21, Down syndrome (DS) is essentially characterized by severe abnormalities in the nervous system that result in mental retardation. In addition, cardiac, gastrointestinal, endocrine, dermatological problems, and skeletal malformations are life-long concerns in DS. Deficiencies of hematopoietic system such as decreased numbers of B and T cells (Cossarizza et al., 1990) are very frequent in these patients as well as a hypoplastic thymus (Levin and Cobian, 1999) and their risk of developing myeloproliferative diseases as well as leukemias is drastically increased ( ). Indeed, blasts may be detected in the blood of up to ten percent in neonates with Down Syndrome (DS)1 (Hasle, 2001). To investigate the pathogenic mechanisms in DS, mouse models have been produced since the distal third of their chromosome 16 is syntenic to the distal end of human chromosome 21. Mouse fetuses with trisomy 16 exhibit abnormalities in the hematopoietic and immune systems such as a hypoplastic thymus and decreased numbers of hematopoietic precursor cells in the liver2 (Epstein et al., 1985) However, trisomy for all of chromosome 16 is incompatible with postnatal survival. Therefore, mice that are trisomic for only the segment of mouse chromosome 16 that is conserved in human chromosome 21 have been developed (Reeves et al., 1995). These Ts65Dn mice survive to adulthood and exhibit phenotypic abnormalities that resemble those of DS patients including increased apoptosis in the thymus (Paz-Miguel et al., 1999).

The present inventors have recently reported long-term cultures of adult bone marrow stem cells explanted from various strains of mice including those parental for Ts65Dn mice (Goolsby et al., 2003). After a few weeks, cultures are made up only of CD34+ cells that express a phenotype compatible with that of hematopoietic progenitor/stem cells. These cells grow very vigorously over at least thirty generations, since $10^{16}$ CD34+ bone marrow cells were generated from $10^6$ whole bone marrow cells, comprised of at most $10^5$ CD34+ cells.

In this Example the present inventors have investigated the in vitro proliferative capacity of bone marrow stem cells from Ts65Dn mice in comparison with that of their diploid littermates. The most striking result is a dramatic decrease in the cumulative number of CD34+ bone marrow cells from the Ts65Dn mice compared to their diploid controls. The main reason for the drastically decreased growth of CD34+ cells from Ts65Dn bone marrow, in a specific embodiment, is (a reduced mitotic rate and) a high proportion of apoptotic cells in these cultures. This is consistent with the fact that the vast majority of ex vivo BMSC from Ts65Dn are apoptotic. Exemplary methods are described elsewhere herein.

Figure 17:
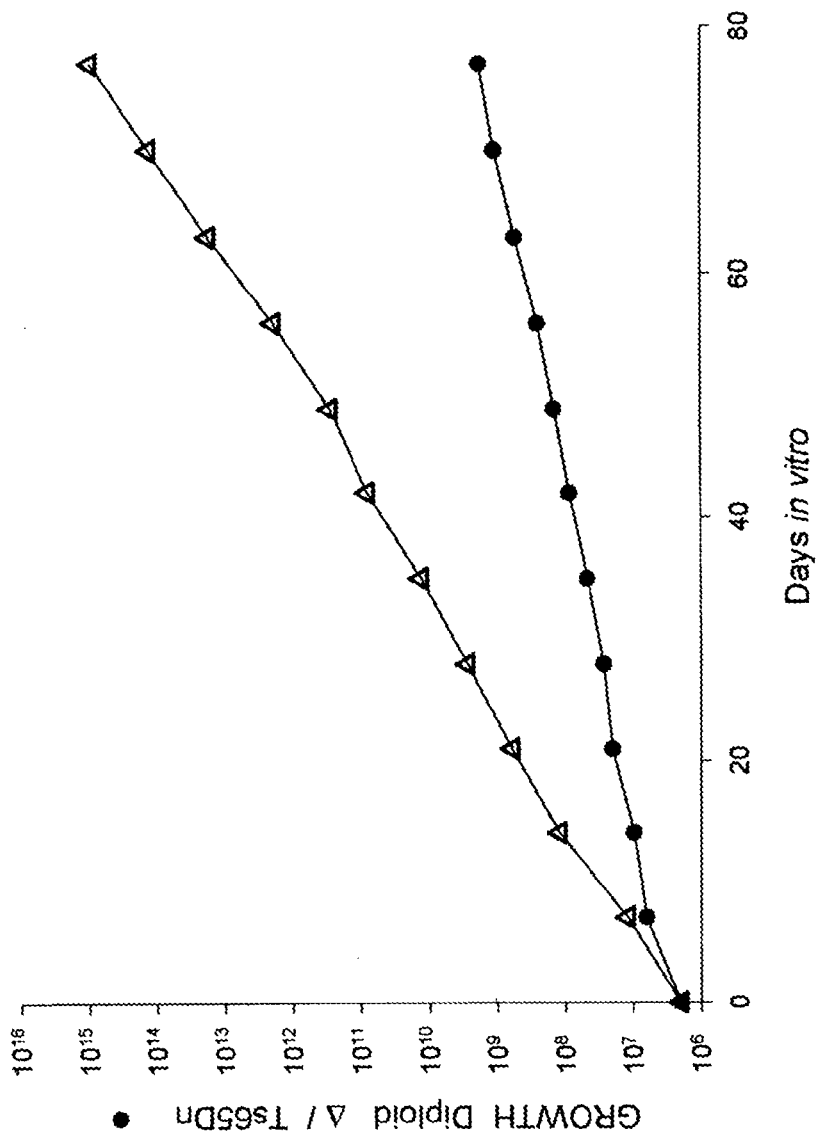
FIG. 17 shows growth curve of cells from adult hematopoietic bone marrow from normal (Δ) and Ts65Dn (•) mice.

I. The Growth Capacity of Hematopoietic Progenitors from Ts65Dn Mice is Drastically Reduced Bone marrow was harvested from adult Ts65Dn mice and their diploid littermates and cultured in liquid medium containing Interleukin-3 (IL-3), Interleukin-6 (IL-6), Stem Cell Factor (SCF), and 2-mercaptoethanol as previously described (Goolsby et al., 2003). The floating cells were subcultured continuously and after four weeks all cells were CD34+ in cultures from both types of mice. However, even after a few days a major difference in their growth rate was observed (FIG. 17). Indeed, the proliferative capacity of the CD34+ bone marrow cells from Ts65Dn mice is drastically reduced as compared to that of the diploid littermates. Starting from the same number of bone marrow cells in diploid and Ts65Dn ($2 \times 10^6$ cells). The cell density of cultures were maintained at comparable levels during the growth curve measurements. After eighty days in culture, the cumulative number of CD34+ cells from Ts65Dn bone marrow is about $10^9$, while at the same time point, the number of cells from diploid littermates reaches $10^{15}$. Under these conditions, the doubling time was 2.5 d for diploid and 11 d for Ts65Dn. The number of generations at 80 d in culture is 8 in Ts65Dn and 33 generations for diploid. These data were highly reproducible with mice from distinct litters (n=8 for each genotype from 2 litters).

II. Decreased Mitosis in Trisomic Hematopoietic Stem Cells

Figure 18:
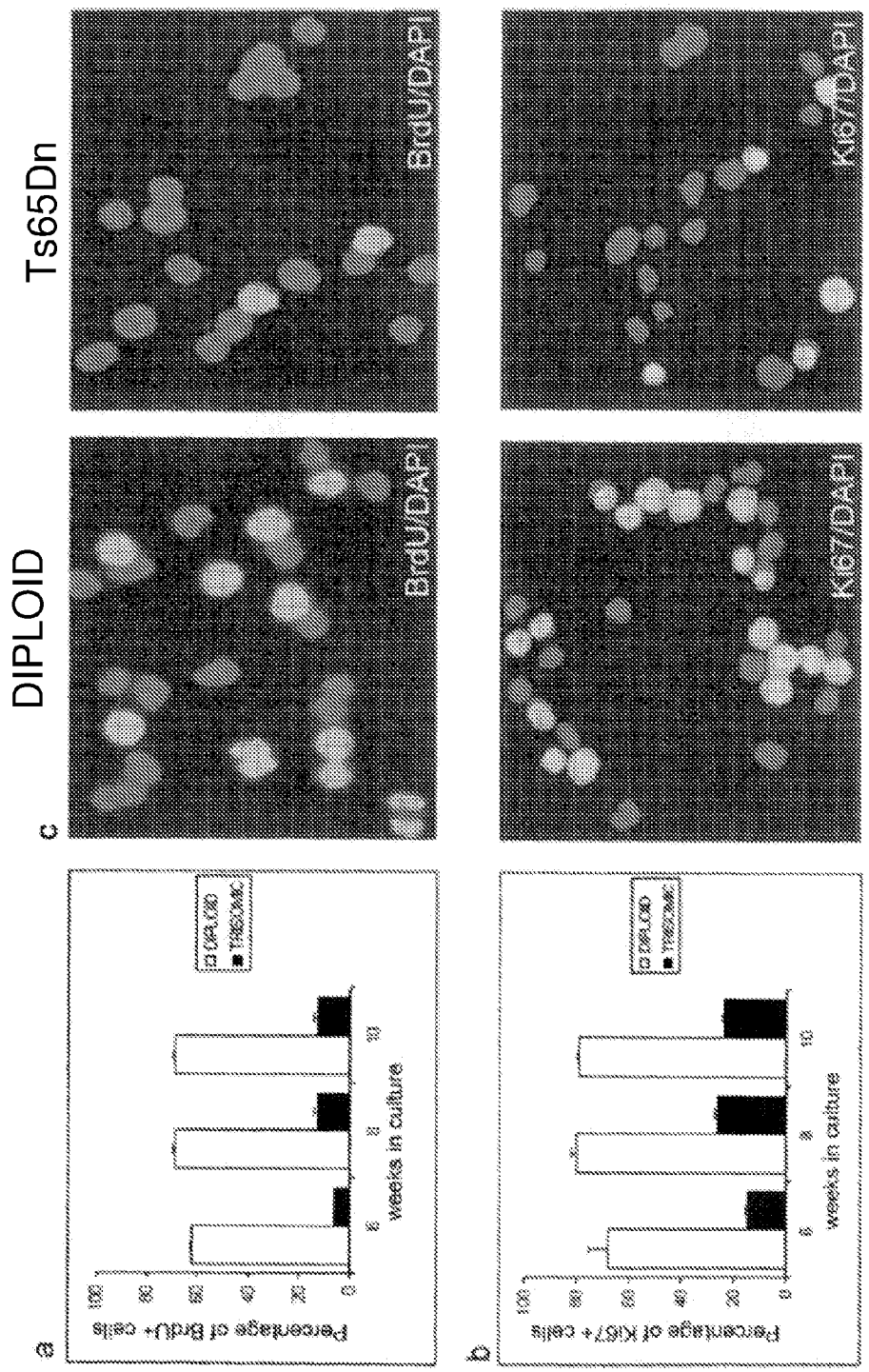
FIGS. 18A and 18B show proliferation of CD34+ in vitro hematopoietic bone marrow cells. Graphs represent the percentage of BrdU (FIG. 18a) and Ki67 (FIG. 18b) immunopositive cells in culture of HSC. The values represent MEAN±SEM. In diploid the number of proliferating cells is 6-7 fold greater thani n Ts65Dn.
In FIG. 18c, the images showed immunostaining for anti-BrdU and anti-Ki67 in diploid and trisomic 8 weeks old cultures of HSC.
Figure 19:
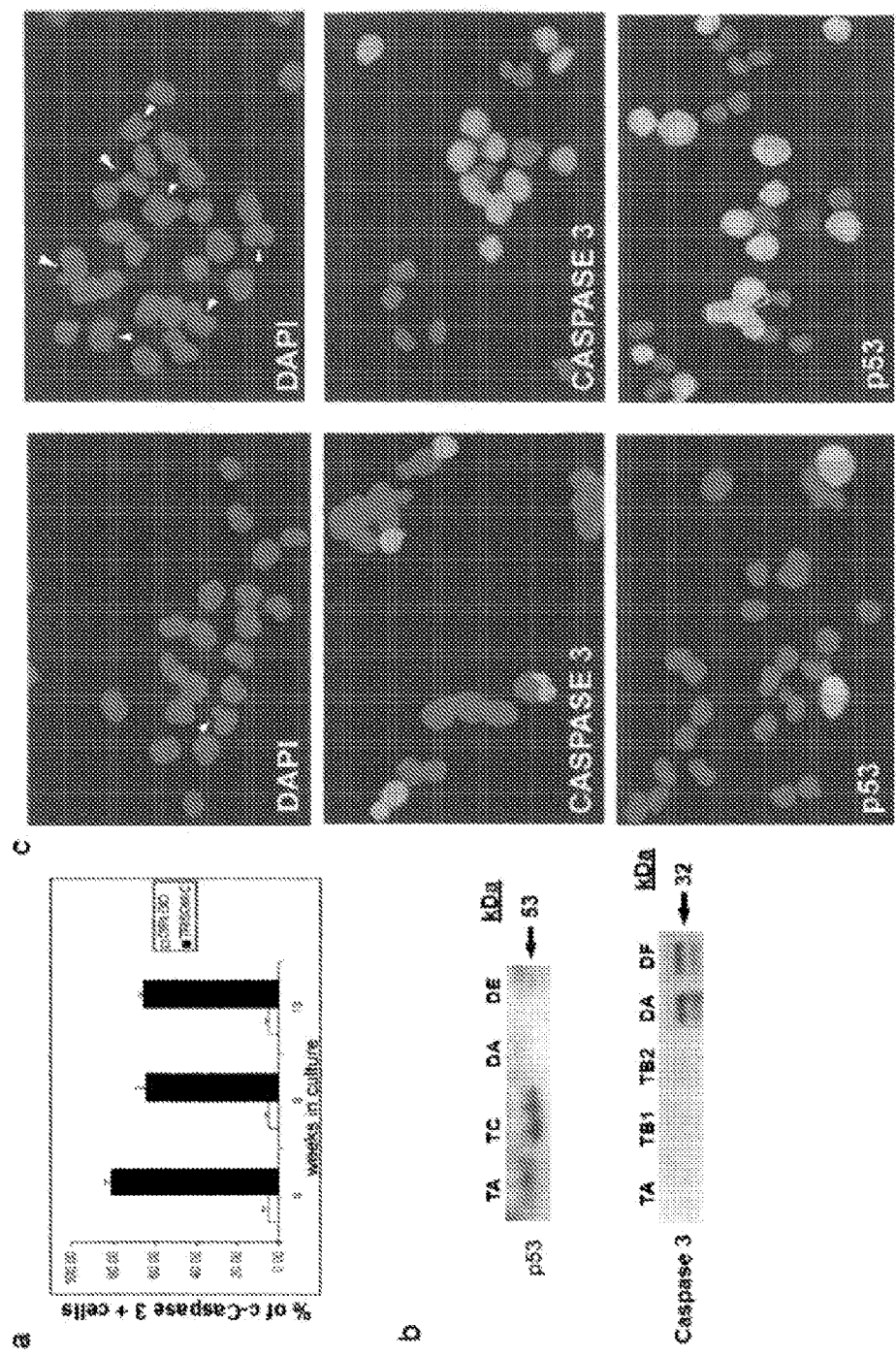
FIGS. 19A-19C show apoptosis in CD34+ in vitro hematopoietic bone marrow cells.

Two main, non-mutually exclusive, mechanisms could account for the very low rate of multiplication of trisomy CD34+ cells: a decreased cell growth rate or a high proportion of apoptotic cells. Cell growth was measured as the percent of cells incorporating BrdU after a five hour exposure and the percent of cells expressing the Ki67 protein after six, eight and ten weeks in culture. To confirm an abnormal mitotic rate, 5 h pulse labeling with BrdU, a thymidine analog, was examined. The pure Ts65Dn CD34+ cultures showed a 7-fold less BrdU labeling than diploid (FIG. 18). FIG. 18a shows incorporation of BrdU was 70% for each time point for diploid but only at 6-10% for trisomic. The difference in mitotic rate between Ts65 and diploid was the same at each time point. In FIG. 18b, the percentage of trisomic and diploid cells that were immunopositive for Ki67, a marker for cell proliferation, were measured. As with the BrdU labeling, over 70% of diploids stained while only 10-20% of trisomics were immunopositive for Ki67 over a 10 wk of the culture.

III. Increased Apoptosis in Trisomic Hematopoietic Stem Cells

In parallel, the proportion of CD34+ cells exhibiting an apoptotic phenotype was examined. At all time points less than 10% of diploid but 65-90% trisomic were diagnosed as apoptotic based upon immunofluorescence to cleaved caspase 3, in the cascade of apoptosis (FIG. 18a)—consistent with nuclear morphology and TUNEL. In addition, Western blots showed that trisomic cultures showed increased caspase (cleaved) expression over diploid (see Mike for gels). Western blots of 10 wk old cultures demonstrated the cleaved 17 kDa band of caspase 3 in Trisomic cultures (FIG. 18b). In addition, most cells in trisomy demonstrated an apoptotic nuclear morphology (FIG. 18b). TUNEL staining showed 10% diploid but 50% trisomic cells at 6 wk in culture. Thus caspase 3 expression is a predictor of apoptosis, further confirming the death pattern of the two genotypes.

A number of mechanisms have been proposed to be involved in apoptosis. An appealing mechanism is one that involves a gene product present on syntenic region of MMU16/HSA21, Ets-2. Ets-2 is known to bind p53 in the apoptotic process and regulation of p53 levels has been correlated with the level of apoptosis (Wolvetang et al., 2003). Therefore, the expression in normal diploid and trisomic CD34+ cells by Western blot and immunocytochemistry was examined. It was found that p53 was not detected by either immunocytochemistry or Western blot analysis of cultured diploid CD34+ cells but is expressed in trisomic CD34+ cells (20% at 6 wk).

Figure 20:
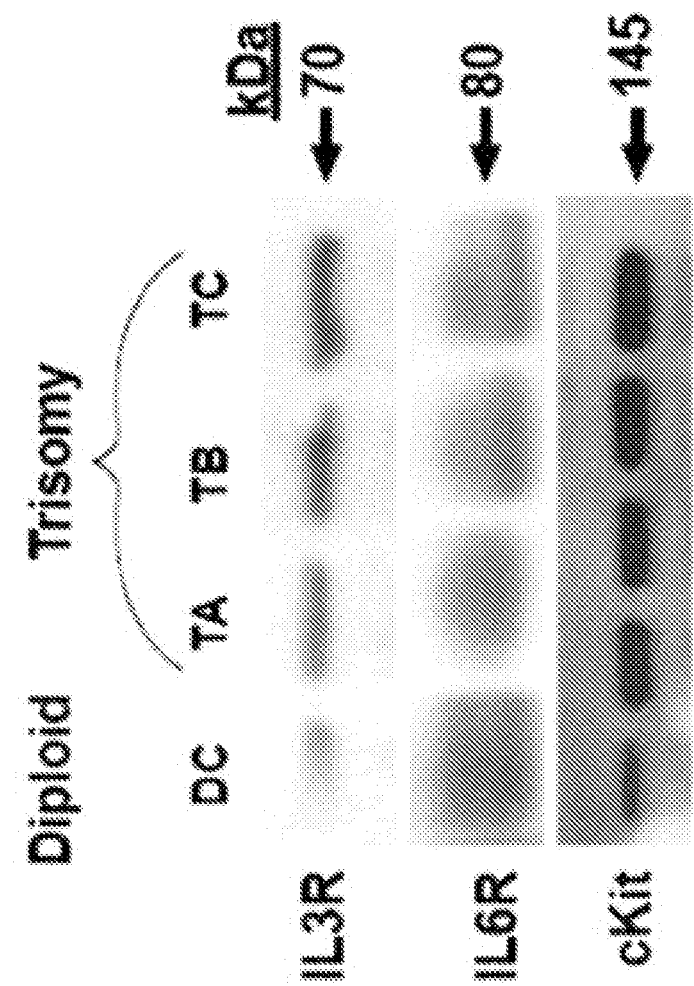
FIG. 20 illustrates western blot analysis showing that both trisomy and diploid mice express the IL-3 receptor, IL-6 receptor and cKit, the SCF receptor.

Taken together, these data show that the low growth rate of CD34+ cells from Ts65Dn bone marrow is the result of a decreased mitotic rate and of increased apoptosis. An obvious explanation would be the lack of receptors for the growth factors used in these experiments. Therefore, Western blot experiments were carried out to determine whether Ts65Dn cells express the growth factor receptors. As shown in FIG. 20, both diploid and trisomic CD34+ cells express IL3-R, IL6-R and c-Kit (SCF receptor) in comparable levels. These results in Ts65Dn cultures are seen either when comparing littermates or when comparing populations of diploid or trisomic animals.

IV. Mitotic and Apoptotic Markers in Ex Vivo Ts65Dn Bone Marrow Cells

However, it could be argued that the low mitotic and high apoptotic rates of trisomic CD34+ cells is the absence in the culture medium of growth factors that would be required for survival by the intrinsic CD34+ cells present in vivo. Therefore, the proportion of ex vivo CD34+ cells from trisomic and diploid mice expressing mitotic and apoptotic markers was investigated. FIG. 21 shows that the percent of CD34+ cells in the trisomic bone marrow is 5% while the percent in diploid bone marrow is 7%. Quite interestingly, a majority of these were assayed at different time points in culture as compared to their controls. The clearest result is that the phenotype of the trisomic CD34+ cells does not differ from that of the diploid littermates (Table 9).

TABLE 9

Gene Expression by Cultured Bone Marrow Stem Cells

|  |  |  |  | Percent Expressing Marker | | | | |
|---|---|---|---|---|---|---|---|---|
|  | Secondary |  |  | Normal | | Trisomy | | |
| Antibody | (Dilution) | Species | Fluorochrome | NormA | NormC | TriA | TriB | TriC |
| Hematopoietic Precursor | | | | | | | | |
| CD45 | (1:200) | Rat monoclonal | Rhodamine | 100 | 100 | 100 | 100 | 100 |
| CD34 | (1:200) | Rat monoclonal | Rhodamine | 100 | 100 | 100 | 100 | 200 |
| cKit | (1:200) | Rat monoclonal | Rhodamine | 100 | 100 | 100 | 100 | 100 |
| Sca-1 (4-20)* | (1:200) | Rat monoclonal | Rhodamine | 100 | 100 | 30 | 19 | 45 |
| Sca-1 (5-3)* | (1:200) | Rat monoclonal | Rhodamine | 85 | 100 | 86 | 82 | 87 |
| Embryonic and Natural Stem Cell | | | | | | | | |
| 4-Oct | (1:200) | Rabbit polyclonal | FITC | 100 | 100 | 100 | 100 | 100 |
| Pax 6 | (1:200) | Rabbit polyclonal | FITC | — | 100 | 100 | 100 | 100 |
| Nestin | (1:200) | Mouse monoclonal | FITC | — | 100 | 100 | 100 | 100 |
| AA4.1 | (1:200) | Rat monoclonal | Rhodamine | 100 | 100 | 100 | 100 | 100 |
| Thy 1.1 | | | FITC | 100 | 100 | 100# | 100 | 100# |
| Neural Markers | | | | | | | | |
| HuC/HuD | (1:200) | Mouse monoclonal | FITC | 100 | 100 | 100 | 100 | 100 |
| Neurofilament H | (1:200) | Mouse monoclonal | FITC | 100 | 100 | 100 | 100 | 100 |
| NeuN | (1:200) | Mouse monoclonal | FITC | 100 | 100 | 100 | 100 | 100 |
| Gad 65 | (1:200) | Rabbit polyclonal | FITC | 100 | 100 | 100 | 100 | 100 |
| TH\ | (1:200) | Rabbit polyclonal | FITC | 0 | 0 | 0 | 0 | 0** |
| M2 (AChR) | (1:200) | Rabbit polyclonal | FITC | 0 | 0 | 0 | 0 | 0 |
| DCX | (1:200) | Guinea Pig | FITC | 100 | 100 | 100 | 100 | 100 |
| MAP2 (AB) | (1:200) | Mouse monoclonal | FITC | 100 | 100 | 100 | 100 | 100 |
| Astroglia | | | | | | | | |
| GFAP | (1:200) | Rabbit polyclonal | FITC | 0 | 0 | 0 | 0 | 0** |
| Oligodendroglia | | | | | | | | |
| CNPase | (1:200) | Mouse monoclonal | FITC | 100 | 100 | 100 | 100 | 100 |
| MOSP | (1:200) | Mouse monoclonal | FITC | 100 | 100 | 100 | 100 | 100 |
| PLP | (1:200) | Mouse monoclonal | FITC | 100 | 100 | 100 | 100 | 100 |
| MAG | (1:200) | Mouse monoclonal | FITC | 100 | 100 | 100 | 100 | 100 |
| NG2 | (1:200) | Mouse monoclonal | FITC | 100 | 100 | 100 | 100 | 100 |
| 04 | (1:200) | | FITC | 100 | 100 | 100 | 100 | 100 |
| GalC | (1:200) | | FITC | 0 | 0 | 0 | 0 | 0 |

*Note date
**Non-specific binding
Tri > Norm

CD34+ cells from Ts65Dn express the apoptotic markers, while only a minority appear to be mitotic. In contrast in CD34+ diploid cells, a majority of the cells are mitotic and a minority appear to be apoptotic. These results clearly show that the in vitro data are not a culture artifact, but only amplify the in vivo situation.

V. Phenotypic Markers of CD34+ Cells

However, it was important to determine whether the slow growing population of CD34+ cells from trisomic mice exhibited the same phenotype as that of CD34+ cells of their normal littermates or whether they derive from a subset of CD34+ cells. Therefore, CD34+ cells from trisomic mice Thus, both trisomy CD34+ cells as well as diploid CD34+ cells express hematopoietic stem cell markers as well as embryonic stem cell markers. In addition, they express markers for neural stem cells as well as for differentiated neurons and oligodendrocytes, but fail to express lineage specific hematopoietic markers. Thus, the slowly growing CD34+ cells from trisomic mice appear to be a homogeneous population comparable to that of normal mice.

VI. Significance of the Present Example

A general feature of Down Syndrome (DS) development is the presence of apoptosis in the brain and thymus (Sawa et al., 1999; Levin et al., 1979) both in vivo and in culture. Indeed Busseglio and Yankner (1995) have shown that cultured cortical neurons from DS fetal brain display an increased rate of apoptosis and intracellular levels of ROS were elevated 3-4 fold. In the DS thymus, Levin et al. found them to be smaller with lymphocyte depletions resembling thymic involution. In addition, children with DS have both diminished numbers of T cells as well as functional deficiency of these cells. Also, newborns with DS have abnormalities in CD34+ cell numbers (Tamiolakis, et al., 2001) and a transient myeloproliferative disorder (Hassle, 2001).

Similarly, in animal models of DS there is apoptosis in the nervous system (hippocampus, and cortical neurons) thymus, and germ cells (Bambrick et al., 2000; German group; Epstein et al., 1985; Paz-Miguel et al., 1999; Gjertson et al., 1999; Leffler et al., 1999). There is diminished proliferation capacity and premature death of cells. Indeed, during the development of the neocortex of the trisomic 16 mouse, as compared to controls, a smaller proportion of progenitors exit the cell cycle, the cell cycle duration longer, the growth fraction reduced as well as an increase in apoptosis (Haydar et al., 2000).

Figure 16:
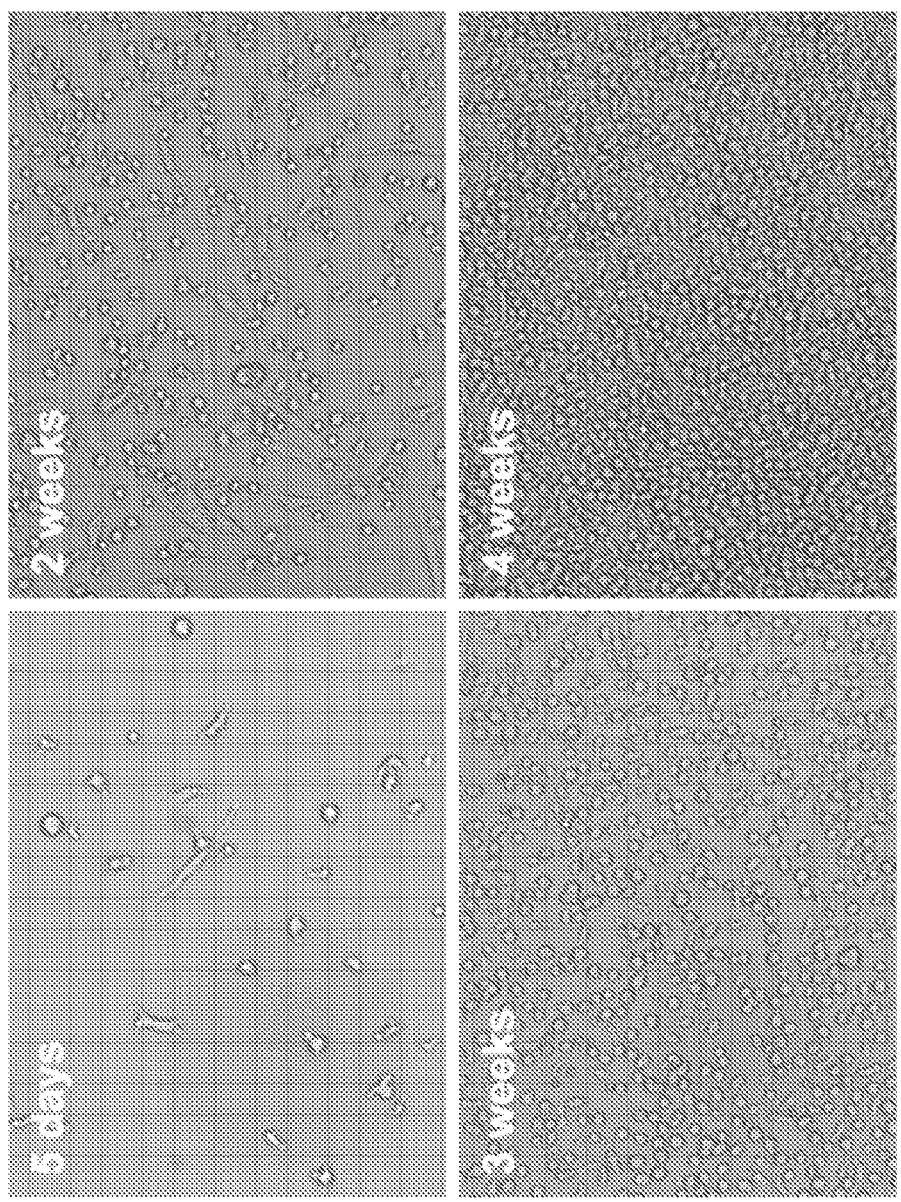
FIG. 16 shows phase contrast photomicrographs of adult human bone marrow stem cells in culture five days, two weeks, three weeks and four weeks. Early cultures contain both cells in suspension in the growth medium and cells attached to the flask.

It therefore appeared of interest to investigate apoptosis of hemopoietic cells in the bone marrow of adult trisomic mice as compared to diploid littermates. A major finding of this study is that a majority of bone marrow hematopoietic stem/progenitor cells from Ts65Dn mice are apoptotic ex vivo. The elevated apoptosis in bone marrow is restricted to the CD34+ stem/progenitor cells. To investigate the functional significance of this observation, we established bone marrow stem cell cultures. With time in culture, cells became homogeneous for proliferating CD34+ cells (FIG. 16). Trisomic CD34+ cells showed a dramatically lower growth rate as compared to diploid littermates. In parallel there was reduced proliferation (FIG. 17), reduced mitosis (BrdU incorporation and Ki67 immunoreactivity) and increased apoptosis (caspase 3, TUNEL, DAPI, FIGS. 18 and 21). In this context, the finding that the phenotype of CD34+ cells from trisomic mice was indistinguishable from that of CD34+ cells cultured from their diploid littermates indicates that these cells do not result from a selection process of a subset of CD34+ cells but rather that they are the consequence of a dramatically decreased growth rate of the whole population of CD34+ cells.

Among the triplicated genes present in Ts65Dn mice, and syntenic to human chromosome 21, many recent reports have proposed a major role for the transcription factor, Ets-2, on the increased rate of apoptosis of neurons as well as of cells from the hemopoietic and immune systems (Wolfstand et al., 2003). A possible target for the Ets-2 protein could be p53, a proapoptotic, cancer-suppressing protein. In this context, the presence of the p53 protein in the slowly growing apoptotic CD34+ cell cultures of Ts65Dn mice, but not in diploid CD34+ cells, is of major interest. However, other genes present as trisomic in Ts65Dn might also be involved in CD34+ increased apoptosis. Indeed, recent observations have indicated that the Runx genes may play a role in hemopoietic cell differentiation. Also, the Dyrk 1A gene expression present on chromosome 16 has been linked to proteins involved in regulation of the cell cycle. In addition, an altered anti-oxidant balance with increased expression of SODI (on chromosomes mouse 16 and human 21) has been proposed to account for certain aspects of the Down Syndrome.

Earlier results of elevated apoptosis in the nervous system, thymus and germ cells, along with these results from the hemopoietic system, suggest that a common mechanism may be at work in stem/progenitor cells of trisomic mice affecting cell proliferation and survival. Down Syndrome may be a general stem cell deficiency.

Example 15

CD34+ Stem Cells Expressing Insulin and Uses Thereof

The present inventors have demonstrated that the CD34+ stem cells express the mRNA for insulin by Reverse Transcriptase—Polymerase Chain Reaction (RT-PCR) using a forward primer for insulin, 5'-AACCCACCCAG-GCTTTTGTC-3' (SEQ ID NO:21) and the reverse primer is 5'-TCCACAATGCCACGCTTCTG-3' (SEQ ID NO:22). They have also shown that the cells translate this mRNA into insulin protein by metabolically labeling the cells with radioactive $^{35}$-sulphur labeled ($^{35}$S)-cysteine. Insulin contains 6 cysteines in its 51 amino acids. After labeling the cells with $^{35}$S-cyteine both cell lysate and the culture medium the cells were growing were run over an anti-insulin antibody column to immunoprecipitate any insulin the might be in the lysate and culture medium. The eluates from the column were separated by molecular weight by polyacrylamide electrophoresis and exposed to autoradiography to demonstrate the presence of metabolically synthesized insulin in the CD34+ cells. Furthermore, the cells were secreting the synthesized insulin, because 95% of the $^{35}$S counts were in the medium and not in the cell lysate. This secretion is important considering that the cells are used in cell replacement therapy in diabetics. It is determined whether the CD34+ cells are able to regulate the amount of insulin they synthesize as a result of the amount of glucose in the culture medium as normal insulin-making pancreatic islet cells do. The CD34+ cells are grown in culture medium containing high and low levels of glucose. In the embodiment wherein they regulate insulin synthesis, they should express more insulin in high glucose medium than in low glucose. The cells are expressing insulin mRNA, and they make and secrete insulin protein. In some embodiments, if the cells do not regulate insulin synthesis, they would regulate insulin synthesis after in vivo differentiation into pancreatic islet Beta-cells, and/or they could be genetically engineered to regulate expression.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents and Patent Applications

WO 94/02593
U.S. Pat. No. 5,830,651
EP0455482

Publications

Azizi, S. A., Stokes, D., Augelli, B. J., DiGirolamo, C. & Prockop, D. J. (1998) Proc. Natl. Acad. Sci. USA 95, 3908-3913.
Bhattacharya, B., Miura, T., Brandenberger, R., Mejido, J., Luo, Y., Yang, A. X., Joshi, B. H., Ginis, I., Thies, R. S., Amit, M., Lyons, I., Condie, B. G., Istkovits-Eldor, J., Rao, M. S., and Puri, R. K. (2004) Blood 103(8), 2956-2964.
Bonilla, S., Alaroon, P., Villaverdi, R. Aparicio, P., Silva, A. & Martinez, S. (2002) Europ. J. Neurosci. 15, 575-582.
Brazelton, T. R., Rossi, F. M. V., Keshet, G. I. & Blau, H. M. (2000) Science 290, 1775-1779.
Burns, C. E., Zon, L. I. (2002) Dev. Cell. 3, 612-613.
Cai, J., Weiss, M. L., Rao, M. S. (2004) Exp. Hematology 32, 585-598.
Castro, R. F., Jackson, K. A., Goodell, M. A., Robertson, C. S., Liu, H. & Shine, H. D. (2002) Science 297, 1299.
Cossarizza, et al. (1990) Am. J. Med Genet Suppl. 7: 213-8.
Epstein, C J., et al. (1985) J. Exp. Med. 162:695-712.
Fischer, A. J., McGuire, C. R., Dierks, B. D. & Rey, T. A. (2002) J. Neurosci. 22, 9387-9398.
Fischer, A. J. & Rey, T. A. (2001) Nature Neurosci. 4, 247-252.
Goolsby et al. (2003) PNAS 100: 14926-14931.
Hasle, H., 2001, Lancel Oncol 2: 429-36.
Hess, D. C., Hill, W. D., Martin-Studdard, A., Carroll, J., Brailer, J. & Carothers, J. (2002) Stroke 33, 1362-1368.
Jiang, Y., et al. (2002) Nature 418, 41-9.
Kabos, P., Ehtesham, M., Kabosova, A., Black. K. L. & Yu, J. S. (2002) Exp. Neurol. 178, 288-293.
Kopen, G. C., Prockop, D. J. & Phinney, D. G. (1999) Proc. Natl. Acad. Sci. USA 96, 10711-10716.
Laywell, E. D., Rakic, P., Kukekov, V. G., Holland, E. C. & Steindler, D. A. (2000) Proc. Natl. Acad. Sci. USA 97, 13883-13888.
Lin, H., Schagat, T. (1997) Trends Genet. 13, 33-39.
Makar, T. K., Wilt, S., Dong, Z., Fishman, P., Mouradian, M. M. & Dhib-Jalbut, S. (2002) J. Interferon & Cytokine Res. 22, 783-791.
Malatesta, P., Hack, M. A., Hartfuss, E., Kettenmann, H., Klinkert, W., Kirchhoff, F. & Gotz, M. (2003) Neuron 37, 751-764.
Marty, M. C., Alliot, F., Rutin, J., Fritz, R., Trisler, D. & Pessac, B. (2002) Proc. Natl. Acad. Sci. USA 99, 8856-8861.
Mezey, E., Chandross, K. J., Harta, G., Maki, R. A. & McKercher, S. R. (2000) Science 290, 1779-1782.
Morrison, S. J., Shah, N. M., Anderson, D. J. (1997) Cell 88, 287-298.
Paz-Miguel, J E. et al. (1999) J. Immunol 163:5399-5410.
Reeves, R. H., et al. (1995) Nat. Genet. 11: 109-11.
Wolfstang, E. J. et al. (2003) Neurobiol. Disease, 14:349-356.
Woodbury, D., Schwarz, E. J., Prockop, D. J., & Black, I. B. (2000) J. Neurosci. Res. 61, 364-370.

What is claimed is:

1. A method of isolating CD34+ stem cells from a plurality of bone marrow cells, comprising the steps of:
   culturing bone marrow cells in a first liquid cell culture medium that lacks serum, but that comprises interleukin-3, interleukin-6, stem cell factor, and beta-mercaptoethanol;
   successively passaging cells in suspension from the first medium to a subsequent liquid cell culture medium that lacks serum, but that comprises interleukin-3, interleukin-6, stem cell factor, and beta-mercaptoethanol, wherein the passaging occurs about once a week or more than once a week and the successive passaging steps occur over the course of three to four weeks; and
   isolating the cells in suspension from the final medium.

2. The method of claim 1, wherein the first liquid cell culture medium lacks matrix and feeder cells.

3. The method of claim 1, wherein the subsequent liquid cell culture medium lacks matrix and feeder cells.

4. The method of claim 1, wherein the passaging occurs about once a week.

5. The method of claim 1, wherein the passaging occurs more than once a week.

6. The method of claim 1, wherein the first liquid cell culture medium further comprises Flt-3/Flk-2, Tpo, Shh, Wnt-3a, Kirre, or a mixture thereof.

7. The method of claim 1, wherein the isolated cells express Oct4, Neurofilament H, Sca-1, AA4.1, cKit, CD45, HMBP, Pax-6, HuC/HuD, NeuN, GAD65, CNPase, MOSP, MBP2, galactocerebroside, NG2, or a combination thereof.

8. The method of claim 1, further comprising the step of delivering one or more of the stem cells to an individual.

* * * * *